United States Patent
Dai

(10) Patent No.: US 12,180,182 B2
(45) Date of Patent: Dec. 31, 2024

(54) (DI)AMINATION OF ACTIVATED ALLENE COMPOUNDS, DERIVATIVES THEREOF, AND METHODS FOR SYNTHESIS OF THE SAME

(71) Applicant: Purdue Research Foundation, West Lafayette, IN (US)

(72) Inventor: Mingji Dai, Alpharetta, GA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 18/060,922

(22) Filed: Dec. 1, 2022

(65) Prior Publication Data

US 2023/0174506 A1    Jun. 8, 2023

Related U.S. Application Data

(60) Provisional application No. 63/284,843, filed on Dec. 1, 2021.

(51) Int. Cl.

| | | |
|---|---|---|
| *C07D 401/06* | (2006.01) | |
| *C07C 229/34* | (2006.01) | |
| *C07D 209/50* | (2006.01) | |
| *C07D 211/14* | (2006.01) | |
| *C07D 211/62* | (2006.01) | |
| *C07D 263/56* | (2006.01) | |
| *C07D 295/145* | (2006.01) | |
| *C07D 311/16* | (2006.01) | |
| *C07D 333/34* | (2006.01) | |
| *C07D 401/14* | (2006.01) | |
| *C07D 403/06* | (2006.01) | |
| *C07D 405/14* | (2006.01) | |
| *C07D 409/12* | (2006.01) | |
| *C07D 409/14* | (2006.01) | |
| *C07D 413/14* | (2006.01) | |
| *C07D 491/107* | (2006.01) | |
| *C07J 43/00* | (2006.01) | |

(52) U.S. Cl.
CPC .......... *C07D 401/06* (2013.01); *C07C 229/34* (2013.01); *C07D 209/50* (2013.01); *C07D 211/14* (2013.01); *C07D 211/62* (2013.01); *C07D 263/56* (2013.01); *C07D 295/145* (2013.01); *C07D 311/16* (2013.01); *C07D 333/34* (2013.01); *C07D 401/14* (2013.01); *C07D 403/06* (2013.01); *C07D 405/14* (2013.01); *C07D 409/12* (2013.01); *C07D 409/14* (2013.01); *C07D 413/14* (2013.01); *C07D 491/107* (2013.01); *C07J 43/003* (2013.01); *C07B 2200/05* (2013.01)

(58) Field of Classification Search
CPC ... C07D 401/06; C07D 211/14; C07D 403/06
See application file for complete search history.

(56) References Cited

U.S. PATENT DOCUMENTS

2009/0176807 A1*  7/2009  Regan ...................... A61P 3/00
                                                          544/333

* cited by examiner

*Primary Examiner* — Kamal A Saeed
(74) *Attorney, Agent, or Firm* — Reichel Stohry Dean LLP; Natalie J. Dean

(57) ABSTRACT

One-pot synthesis methods for producing amines from activated allenes and derivatives thereof are provided, as well as the compounds produced thereby.

13 Claims, 11 Drawing Sheets

- ⓝ amide, sulfonamide, cabamate, urea, N-alkoxy amide, etc. (A)
- ⓝ sulfonamide, urea, azide, etc. (B)
- ▷ transition metal reagents/catalysts: Os, Co, Cu, Fe, Pd, Rh, etc.
- ▷ special, expensive, and/or explosive reagents: azide, iodine(III), peroxide, diaziridinone, etc.
- ▷ activation, protection, deprotection, and/or further functionalization
- ▷ undifferentiated "N" and "N"
     (A)     (B)

(DI)AMINATION OF ACTIVATED ALLENE COMPOUNDS, DERIVATIVES THEREOF, AND METHODS FOR SYNTHESIS OF THE SAME

REFERENCE TO RELATED APPLICATIONS

This application is related to and claims the priority benefit of U.S. Provisional Application No. 63/284,843, filed Dec. 1, 2021. The content of the aforementioned application is hereby incorporated by reference herein in its entirety.

STATEMENT OF GOVERNMENT INTEREST

This invention was made with government support under Award No. R35 GM128570 awarded by the National Institutes of Health (NIH). The government has certain rights in the invention.

TECHNICAL FIELD

The present disclosure relates to methods for one-pot synthesis of activated allenes and derivatives thereof, and to the compounds made by such methods.

BACKGROUND OF THE INVENTION

This section introduces aspects that may help facilitate a better understanding of the disclosure. Accordingly, these statements are to be read in this light and are not admissions about what is or is not prior art.

The 1,2-diamine (vicinal diamine) motif is present in a number of natural products with interesting biological activity and in many chiral molecular catalysts. Vicinal diamines are important scaffolds frequently used in pharmaceutical development, pharmaceuticals, agrochemicals, and natural products. They are also often used as catalysts or ligands for transition metal catalysis.

The direct diamination of unsaturated carbon-carbon bonds, particularly carbon-carbon double bonds, presents a straightforward strategy to prepare vicinal diamines. "Diamination" is a reaction that results in the formation of a diamine, which is a compound containing two amino functional groups. While various intramolecular and intermolecular olefin diamination reactions have been developed (FIG. 1A), the efficient and stereocontrolled synthesis of vicinal diamines remains a challenge for multiple reasons. For most of the reported olefin diaminations, a tether between the olefin and one or both of the amino groups (eq. A-1 of FIG. 1A) or a linker between the two amino groups (eq. A-2 of FIG. 1A) is required to ensure the occurrence of the corresponding C—N bond formation. One or both amino groups need to be activated and/or protected in the forms of amide, sulfonamide, carbamate, urea, N-alkoxy amide, strained diaziridinones, or other forms in to enable the diamination reactions; thus, in conventional methods, additional steps are necessary to convert the initial amination products to their desired form. The use of alkyl amines in olefin diamination reactions has remained a daunting challenge.

Additionally, precious transition metal complexes are often required as catalysts or even reagents to promote the diamination, which creates potential cost, sustainability, and purification issues. For most of the intermolecular diaminations (including, for example, diazidations) symmetric diamino reagents or two identical amino reagents are required to avoid regioselectivity, which can create problems in differentiating the two amino groups or azides for further modification.

Three-component diamination reactions with two different nitrogen groups ("N"s) are still rare. Notable examples can include Pd-catalyzed diamination and Cu-catalyzed aminoazidations. However, the use of unique amination reagents, explosive azides, or expensive azido-iodine reagents creates a significant barrier to their broad application, especially when scale-up is considered. Furthermore, these reactions do not provide flexibility as the positions of the two different amino groups cannot be switched in these three-component diamination reactions.

Allenes are cumulated dienes with two perpendicular π-systems sharing an sp-hybridized carbon that possess unique reactivity. Diamination of allenes is very rare. In 2009, a gold-catalyzed intramolecular dihydroamination of allenes to synthesize bicyclic products with an imidazolidin-2-one moiety was reported (FIG. 1B, eq. B-1). See Li and Widenhoefer, Gold(I)-Catalyzed Intramolecular Dihydroamination of Allenes with N,N'-Disubstituted Ureas To Form Bicyclic Imidazolidin-2-ones, *Org. Lett.* 11: 2671-2674 (2009). In 2012, an elegant Rh-catalyzed intramolecular allene aziridination followed by nucleophilic aziridine ring opening with an aniline or amine to synthesize cyclic sulfamates has also been developed (FIG. 1B, eq. B-2). See Adams et al., Modular Functionalization of Allenes to Aminated Stereotriads, *J American Chem. Soc.* 134: 10807-10810 (2012).

In 2018, a process for transition-metal-free intermolecular amphoteric diamination of electron deficient allenes with 1,2-, 1,3- or 1,4-diamine derivatives to synthesize saturated 1,4-diazo heterocycles including piperazines, 1,4-diazepanes, and 1,4-diazocanes was also developed (FIG. 1B, eq. B-3). See Ye et al., Expedient Syntheses of N-Heterocycles via Intermolecular Amphoteric Diamination of Allenes, *Nature Communications* 9: 721 (2018). There, unsymmetrical 1,2-, 1,3-, or 1,4-diamines were used to provide orthogonally functionalized or protected 1,4-diazo heterocycles.

As shown in FIG. 1B, equation B-3, the reaction initiates with mixing the diamine derivative A with N-iodosuccinimide (NIS) or N-chlorosuccinimide (NCS). The electron rich alkyl amine of A is selectively halogenated in the presence of an intramolecularly tethered electron-deficient sulfonamide to form an iodoamine or chloroamine (D). Allene B is then added to the reaction mixture, along with $Cs_2CO_3$ or a combination of $Cs_2CO_3$ and KI (for NCS conditions). The iodoamine or chloroamine (with KI) then reacts with allene B via a formal iodoamination process to provide allylic iodide E, which spontaneously undergoes a ring closing substitution with the tethered sulfonamide to afford intermediate F. While intermediate F is not stable for column purification, it can potentially be further elaborated via a subsequent one-pot reduction or functionalization (e.g., trifluoromethylation) to deliver end product C.

While this method can be efficient to make the aforementioned 1,4-diazo heterocycles, it is limited to a ring formation and the use of tethered diamine derivatives. Furthermore, one or both amino groups must be activated and/or protected (e.g., in the form of sulfonamide, carbamate, etc.), thus, the method does not provide a large degree of flexibility.

Novel synthetic methods to prepare novel acyclic compounds and their derivatives are therefore needed.

SUMMARY OF THE INVENTION

The present disclosure relates to novel one-pot synthetic methods with activated allenes and derivatives thereof, and to the compounds made by the novel synthetic methods.

In one embodiment, a method is provided for synthesizing a compound of formula II from a compound of formula I as follows:

$$\underset{I}{\overset{H}{\underset{H}{>}}C=C\overset{R^2}{\underset{R^1}{<}}} \xrightarrow[\text{3. reduction reaction}]{\text{1. amination reaction}} \underset{II}{R^5\overset{H}{\underset{\underset{R^3\diagdown N\diagdown R^4}{|}}{\overset{R^2}{\underset{H}{\overset{|}{C}}}-\overset{H}{\underset{H}{\overset{|}{C}}}-R^1}}}$$

wherein:
- $R^1$ is H or F;
- $R^2$ is an electron-withdrawing group (EWG);
- $R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, wherein $R^2$ and $R^3$ can join together to form an optionally substituted heterocyclic ring;
- $R^5$ is —$NR^6R^7$ or —$XR^8$, wherein:
  - $R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl,
  - $R^6$ and $R^7$ can join together to form an optionally substituted hetero cyclic ring, and
  - X is O or S.

In certain embodiments, the method of synthesizing a compound of formula II from a compound of formula I comprises: providing a solution comprising a secondary amine $R^3R^4NH$ and an amine halogenating reagent; adding a compound of formula I to said solution to carry out a first electrophilic amination reaction; adding a nucleophilic reagent $HNR^6R^7$ or $HXR^8$, and a base to a reaction mixture of the first electrophilic amination reaction to carry out a second nucleophilic reaction; and adding a reducing reagent to a reaction mixture of the second nucleophilic reaction to carry out a third enamine reduction reaction to provide the compound of formula II.

Methods of synthesizing amines from activated allene compounds or derivatives thereof in a one-pot reaction are also provided. In certain embodiments, the method comprises: providing a solution comprising an electrophilic amine or an allene and an amine halogenating reagent and adding a first compound to the solution to carry out a first animation reaction, wherein the first compound comprises an EWG; adding a nucleophilic reagent and a base to a reaction mixture of the animation reaction to carry out a second nucleophilic reaction; and adding a reducing reagent to a reaction mixture of the nucleophilic reaction to carry out a third enamine reduction reaction and synthesize an amine product from an activated allene compound or derivative thereof.

In certain embodiments, the amine halogenating reagent comprises one or more of t-BuOCl, tetra-n-butylammonium iodide (TBAI), N-bromosuccinimide (NBS), N-Iodosuccinimide (NIS), N-Chlorosuccinimide (NCS), KI, and NaI. In certain embodiments of the method, the amine halogenating reagent comprises a mixture of t-BuOCl and TBAI.

The electrophilic amine can be a cyclic aliphatic amine or an acyclic aliphatic amine. In certain embodiments, the electrophilic amine has a structure of the formula $R^3R^4NH$, wherein $R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl. Additionally, the first compound can have a structure of Formula I:

$$\underset{H}{\overset{H}{>}}C=C\overset{R^2}{\underset{R^1}{<}} \qquad \text{I}$$

wherein:
- $R^1$ is H or F;
- $R^2$ is the EWG; and
- in the product, the $R^2$ of Formula II and the $R^3$ of Formula I are joined together to form an optionally substituted heterocyclic ring.

The nucleophilic reagent can be a cyclic amine, an acyclic amine, an amide, a carbamate, an imide, or a sulfonamide. In certain embodiments, the nucleophilic reagent has a structure of the formula $HNR^6R^7$ or $HXR^8$, wherein X is O or S; and $R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl.

In certain embodiments, $R^6$ and $R^7$ of the nucleophilic reagent are (or can be) joined together to form an optionally substituted heterocyclic ring.

In certain embodiments of the method, the base is ceasium carbonate ($Cs_2CO_3$), potassium carbonate ($K_2CO_3$) or tetrahydrofuran (THF).

The reducing agent can comprise or be $NaBH_3CN$. In certain embodiments, the method comprises adding a cosolvent of MeOH/AcOH to a reaction mixture of the reduction reaction.

In certain embodiments, the method further comprises drying and purifying the activated allene compound or derivative thereof.

A method of synthesizing a compound of formula II is also provided. In certain embodiments, the method of synthesizing a compound of formula II from a compound of formula I as follows:

$$\underset{I}{\overset{H}{\underset{H}{>}}C=C\overset{R^2}{\underset{R^1}{<}}} \longrightarrow \underset{II}{R^5\overset{H}{\underset{\underset{R^3\diagdown N\diagdown R^4}{|}}{\overset{R^2}{\underset{H}{\overset{|}{C}}}-\overset{H}{\underset{H}{\overset{|}{C}}}-R^1}}}$$

wherein:
- $R^1$ is H or F;
- $R^2$ is an electron-withdrawing group (EWG);
- $R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, wherein $R^2$ and $R^3$ can join together to form an optionally substituted hetero cyclic ring;

$R^5$ is —$NR^6R^7$ or —$XR^8$, wherein $R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, wherein $R^6$ and $R^7$ can join together to form an optionally substituted hetero cyclic ring, and X is O or S.

The method can further comprise: providing a solution comprising a secondary amine $R^3R^4NH$ and an amine halogenating reagent; adding a compound of formula I to said solution to carry out a first electrophilic amination reaction; adding a nucleophilic reagent $HNR^6R^7$ or $HXR^1$, and a base to reaction mixture of the first electrophilic amination reaction to carry out a second nucleophilic reaction; and adding a reducing reagent to reaction mixture of said second nucleophilic reaction to carry out a third enamine reduction reaction to provide the compound of formula II.

The method can be a one-pot reaction.

The amine halogenating reagent can be t-BuOCl, TBAI, NBS, NIS, NCS, KI, NaI, or any combination of two or more of the foregoing. The EWG comprises an aldehyde group, ketone group, carboxylic acid group, acyl group, ester group, amide group, trihalide group, cyano group, isocyano, sulfonyl group, nitro group, F, or Cl.

Compounds are also provided. In certain embodiments, a compound is provided that is prepared by any of the methods described. In certain embodiments, the compound has a structure of Formula (III):

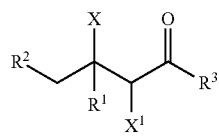

Formula (III)

or is a pharmaceutically acceptable salt thereof, wherein
$R^1$ is D or absent;
$R^2$ is

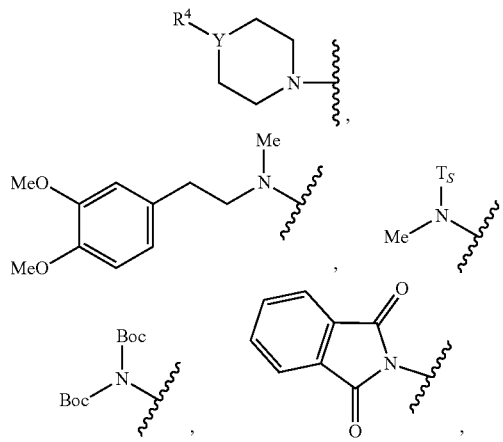

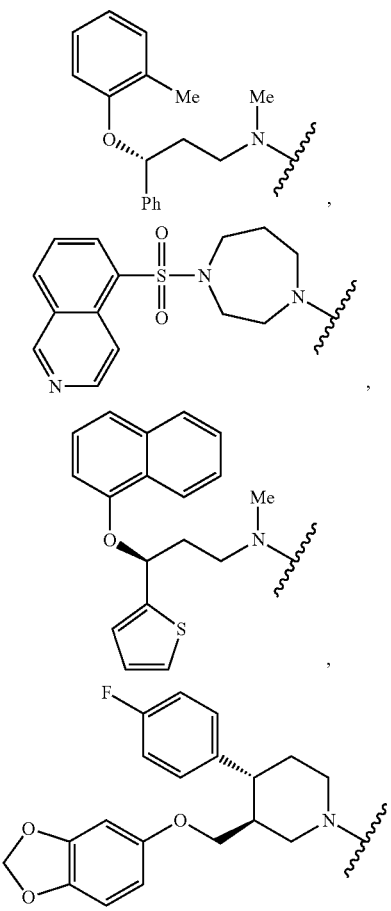

wherein
Y is N, S, C, or O, and
$R^4$ is Ph,

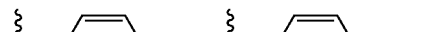
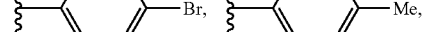
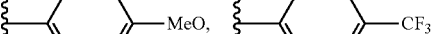
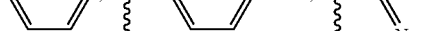
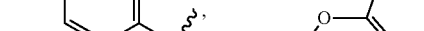

or absent; and

R³ is OBn, OEt

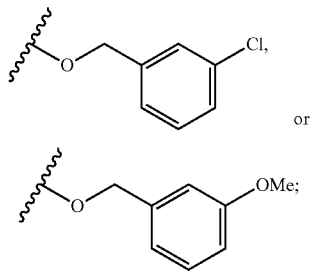

X is

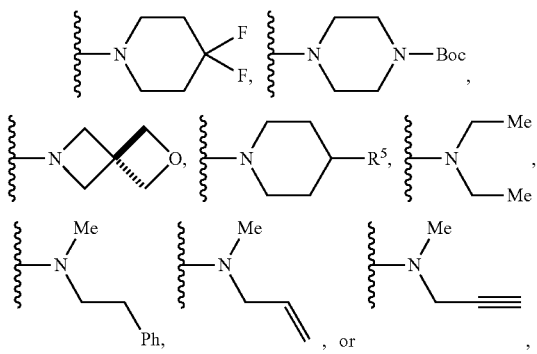

wherein R⁵ is Ph or COOMe; and

X¹ is absent or F.

In certain embodiments, a compound is provided that is prepared by a method described herein, wherein the compound has a structure of Formula (IV):

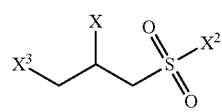
Formula (IV)

or is a pharmaceutically acceptable salt thereof, wherein:

X is

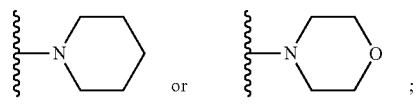

X² is Ph,

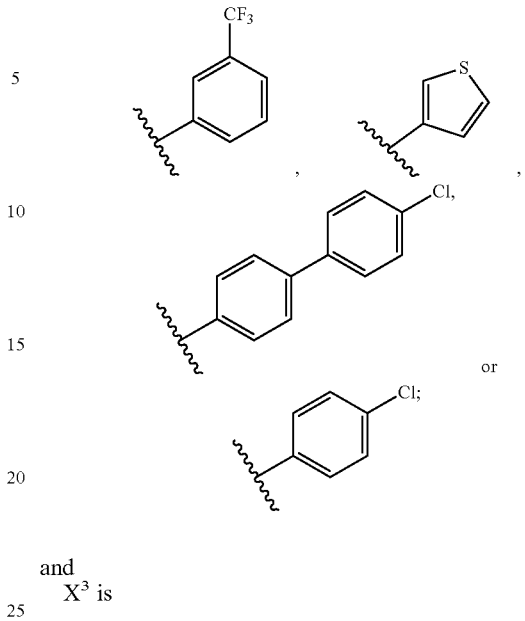

and

X³ is

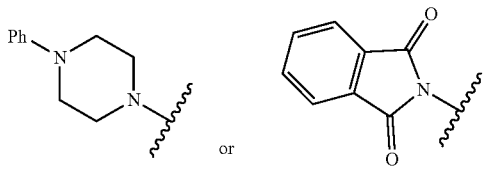

In certain embodiments, a compound is provided that is prepared by a method hereof and has a structure of Formula (V):

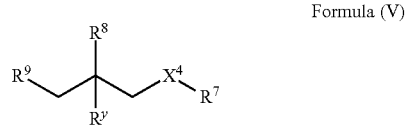
Formula (V)

or is a pharmaceutically acceptable salt thereof, wherein:

X is O or S;

R⁷ is

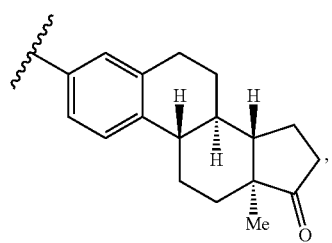

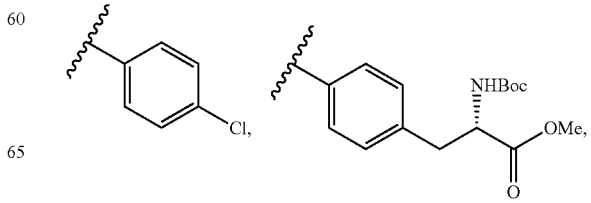

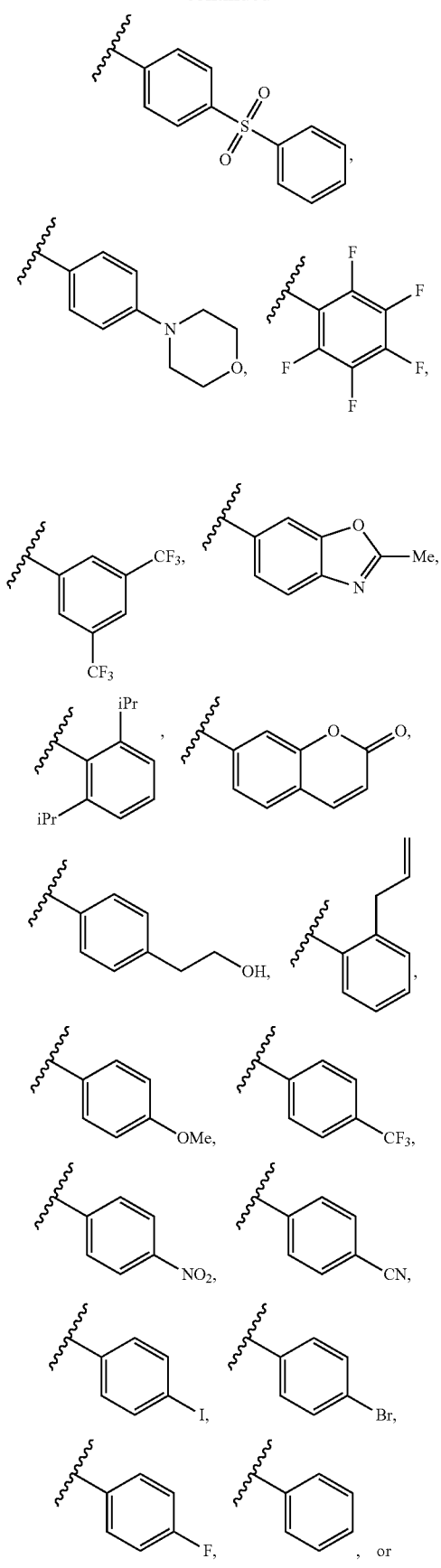

$R^8$ is, $R^9$ is and
$R^y$ is absent or D.

BRIEF DESCRIPTION OF DRAWINGS

The detailed description will be better understood when taken in conjunction with the accompanying drawings, wherein.

DETAILED DESCRIPTION

Figure 1A:
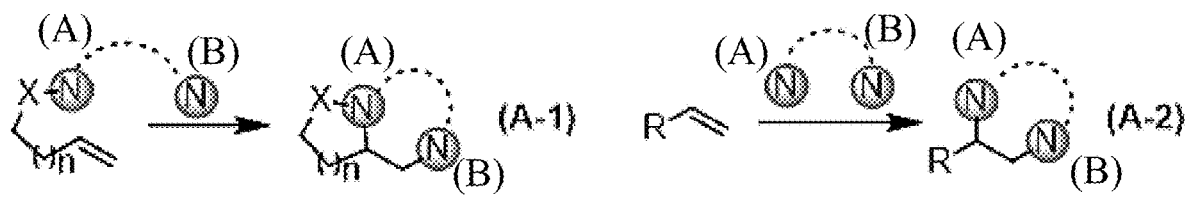
FIG. 1A shows prior art inter- and intra-molecular deamination of olefins.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1B:
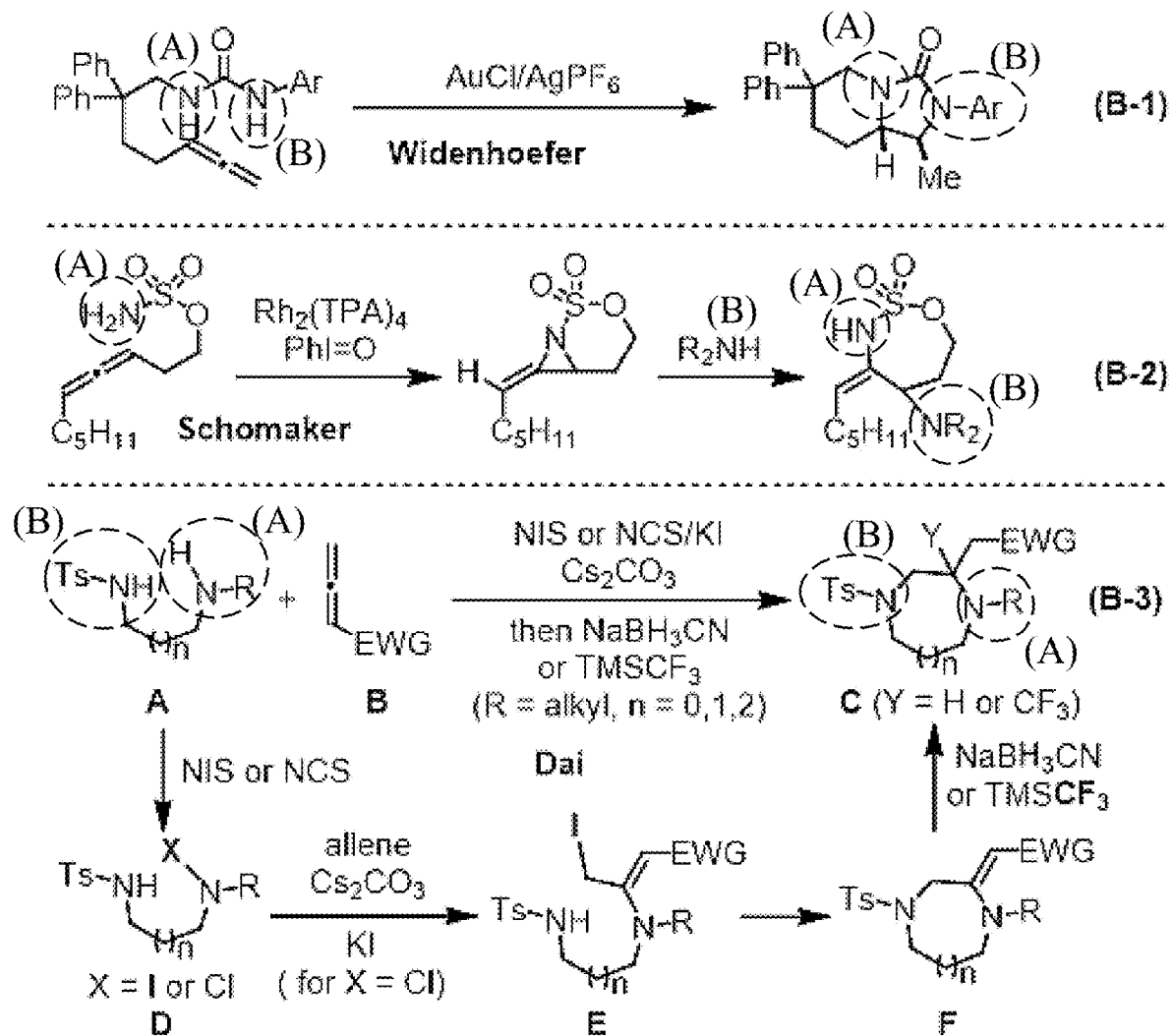
FIG. 1B shows prior art diaminative cyclization of allenes, with a first amine group labeled (A) and a second amine group labeled (B).
Figure 1C:
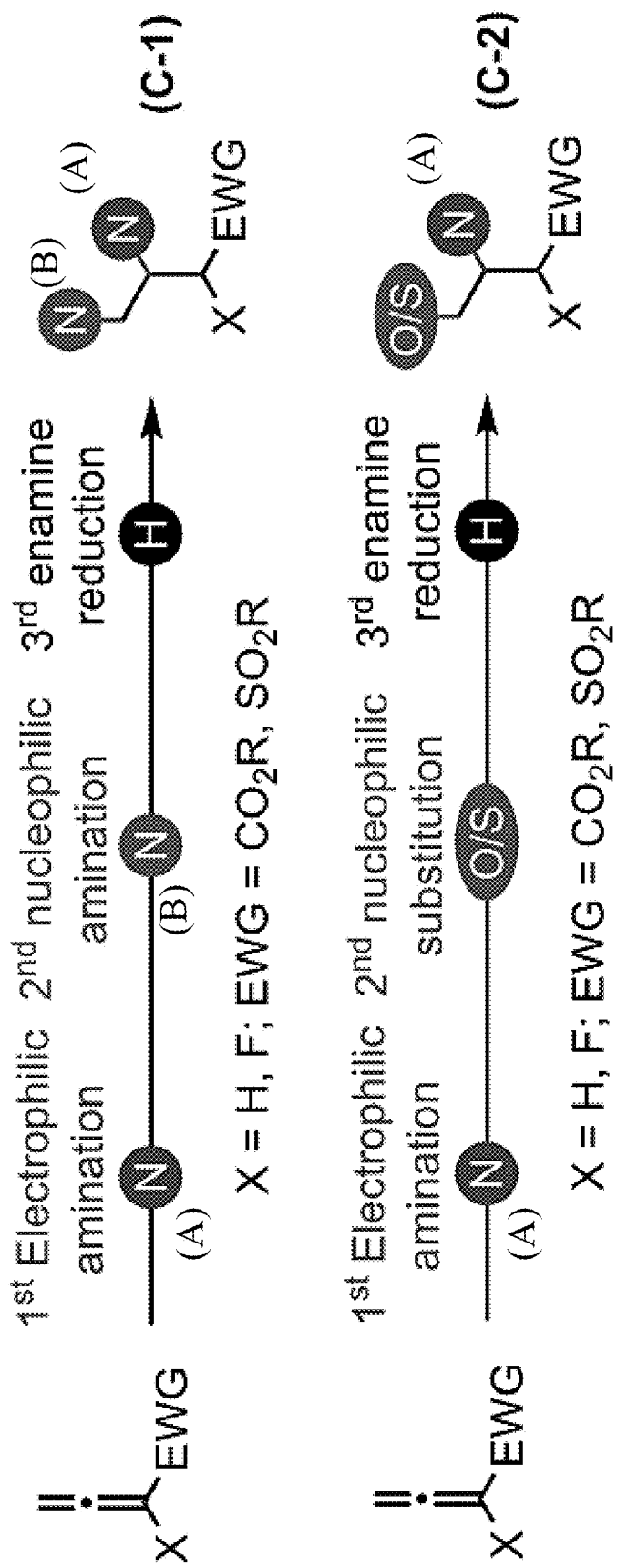
FIG. 1C shows a schematic representation of the intermolecular three-component diamination of allenes pursuant to the method for the deamination of allenes hereof, with an amine group from the first electrophilic amination labeled (A) and an amine group from the second nucleophilic amination labeled (B).

A modular and three-component method is provided for the intermolecular diamination of allenoates to synthesize β,γ-diamino acid derivatives, which are important building blocks and possess great potential in medicine and biology (FIG. 1, C, eq. C-1). The methods utilize the sequential addition of the amines, which allows for the use of two amines such that one serves as the electrophilic amine via an iodo/chloroamine formation and the other acts as the nucleophilic amine for a substitution reaction. The amines can be the same or different, as desired. In certain embodiments, one or both of the amines are aliphatic amines.

The method's unique design allows for flexibility in the product design as the identity of the amines and/or the addition order thereof (e.g., to affect their position in the final product) can be adjusted at will to achieve a specific end product. Accordingly, the methods provide flexibility in product synthesis that has heretofore been unavailable. Further, the method features mild reaction conditions, can use readily available reagents, and exhibits excellent functional group tolerability. The method also does not require the addition of any transition metal catalyst.

Unlike conventional methodologies, the novel deamination reaction that results from the methods hereof need not be limited to sulfonamides, amides, or carbamates. Both acyclic and cyclic alkylamines can be used. Given the importance of saturated N-heterocycles in drug discovery, their direct incorporation represents a salient feature of the methods. Additionally, the reagents of the method are typically cheap and readily available, and the reaction facilitated by the method features high regioselectivity and, in certain embodiments, does not require any transition metal catalyst.

As noted above, the two aliphatic amines can be switched to allow quick generation of analogs for structure-activity relationship study.

In certain embodiments, a method of synthesizing activated allene compounds or derivatives thereof is provided. The method can comprise facilitating a first amination reaction, a second nucleophilic reaction, and a third reduction reaction in a one-pot synthesis. As used herein, the terms "one-pot reaction" and "one-pot synthesis" are used interchangeably and mean a strategy where a reactant is subjected to successive chemical reactions in just one reactor. A one-pot reaction can avoid a work-up or separation process, purification (e.g., of intermediate chemical compounds), and/or isolation (e.g., of an intermediate chemical compound), and increase chemical yield. In certain embodiments, one-pot synthesis can be sequential one-pot synthesis, meaning reagents are added to a reactor one at a time. In certain embodiments, one-pot synthesis does not require work-up. As used herein "work-up" refers to a series of manipulations required to isolate and purify a product(s) of a chemical reaction. In certain embodiments, the one-pot synthesis is sequential and without work-up (e.g., a telescoping synthesis). One-pot reactions can be extremely beneficial—especially in a commercial context—as they can generate complex targets and significantly shorten the number of steps required overall.

The first animation reaction can comprise providing a solution comprising an electrophilic amine and an amine halogenating reagent and adding a compound to the solution to carry out a first electrophilic amination reaction (e.g., to result in a reaction solution of the electrophilic reaction). In certain embodiments, the first animation reaction is performed in part under argon atmosphere.

As used herein, "amine halogenating reagent" means any appropriate reagent that can provide a halogen to the nitrogen of an amine group. The non-limiting amine halogenating reagent can be, but is not limited to, t-BuOCl, tetra-n-butylammonium iodide (TBAI), N-bromosuccinimide (NBS), N-Iodosuccinimide (NIS), N-Chlorosuccinimide (NCS), KI, NaI, or any combination of two or more of the foregoing. In certain embodiments, the amine halogenating reagent comprises a mixture of t-BuOCl and TBAI.

The electrophilic amine can be a cyclic or acyclic aliphatic amine. In certain embodiments, the electrophilic amine is a cyclic amine such as, without limitation, a saturated N-heterocycle such as pyrrolidine, piperidine, piperazine, azepane, morpholine, or azetidine. In certain embodiments, the electrophilic amine is a diethyl amine, N-methyl-2-phenylethan-1-amine, an allylic amine, or a propargylic amine. In certain embodiments, the electrophilic amine is an amine shown in Table 1 (below).

In certain embodiments, the electrophilic amine comprises a secondary amine having the formula $R^3R^4NH$, wherein $R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, and $R^2$ and $R^3$ can join together to form an optionally substituted heterocyclic ring. The term "optionally substituted" or "optional substituents" means that the groups in question are either unsubstituted or substituted with one or more of the substituents specified. When the groups in question are substituted with more than one substituent, the substituents can be the same or different. The terms "independently," "independently are," and "independently selected from" mean that the groups in question can be the same or different; each group's identity is independent of any other group.

The compound added to the solution to carry out a first electrophilic amination reaction can be a compound of formula I:

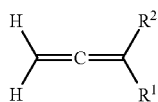

I wherein, $R^1$ is H or F; and
$R^2$ is an electron-withdrawing group (EWG).

As used herein, the term "electron withdrawing group" or "EWG" can be any functional group that removes electron density from a π system, such as the conjugated carbon-carbon double bond system, making the π system more electrophilic. In certain embodiments, an EWG is an aldehyde group, ketone group, carboxylic acid group, acyl group, ester group, amide group, trihalide group, cyano group, isocyano, sulfonyl group, nitro group, F, or Cl.

A nucleophilic reagent and a base are then added to the reaction mixture from the electrophilic reaction to facilitate a nucleophilic reaction (e.g., to result in a reaction mixture of the nucleophilic reaction).

The nucleophilic reagent can be a cyclic or acyclic amine. In addition, an amide, imide, or sulfonamide can be used as the nucleophilic partner. In certain embodiments, the nucleophilic reagent has the formula $HNR^6R^7$ or $HXR^8$, wherein X is O or S; and $R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl. In certain embodiments, $R^6$ and $R^7$ can join together to form an optionally substituted hetero cyclic ring.

The base can be any base capable of facilitating the nucleophilic reaction with the nucleophilic reagent and the reaction mixture from the electrophilic reaction. In certain embodiments, the base is ceasium carbonate ($Cs_2CO_3$), or potassium carbonate ($K_2CO_3$).

A reducing reagent is then added to the reaction mixture of the nucleophilic reaction to facilitate a third enamine reduction reaction. The reducing agent can comprise $NaBH_3CN$. The reducing agent can comprise $NaBH_3CN$ and a co-solvent of MeOH/AcOH.

In certain embodiments, the third enamine reduction reaction provides a compound of formula II:

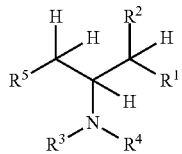

II wherein:
$R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, and $R^2$ and $R^3$ can join together to form an optionally substituted heterocyclic ring;

$R^5$ is $-NR^6R^7$ or $-XR^8$, wherein:
$R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl,
$R^6$ and $R^7$ can join together to form an optionally substituted hetero cyclic ring, and
X is O or S.

In certain embodiments, the method comprises providing a solution comprising a secondary amine $R^3R^4NH$ (e.g., wherein $R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, and $R^2$ and $R^3$ can join together to form an optionally substituted heterocyclic ring) and an amine halogenating reagent; adding a compound of formula I to said solution to carry out a first electrophilic amination reaction; adding a nucleophilic reagent $HNR^6R^7$ or $HXR^8$ (e.g., where $R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, and, in certain embodiments, $R^6$ and $R^7$ can join together to form an optionally substituted hetero cyclic ring), and a base to reaction mixture of the first electrophilic amination reaction to carry out a second nucleophilic reaction; and adding a reducing reagent to reaction mixture of said second nucleophilic reaction to carry out a third enamine reduction reaction to provide the compound of formula II.

In certain embodiments, a method of deamination comprises reacting benzyl allenoate and two amines with at least one oxidizing reagent in a one-pot reaction. The oxidizing reagent can comprise any of the amine halogenating reagents described herein. In certain embodiments, the oxidizing reagent comprises NIS and/or NCS. In certain embodiments, the oxidizing reagent(s) comprises t-BuOCl. In certain embodiments, the oxidizing reagent(s) comprises t-BuOCl and an iodide salt. In certain embodiments, the iodide salt is TBAI. Any iodide salt can be used in conjunction with t-BuOCl.

In certain embodiments, the method comprises a method of synthesizing a compound of formula II from a compound of formula I. Such method can be represented by the following:

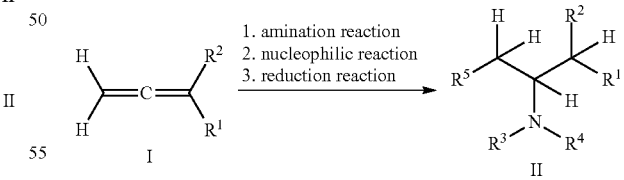

wherein:
$R^1$ is H or F;
$R^2$ is an electron-withdrawing group (EWG);
$R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, and $R^2$ and $R^3$ can join together to form an optionally substituted heterocyclic ring;

$R^5$ is —$NR^6R^7$ or —$XR^8$, wherein:
$R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl,
$R^6$ and $R^7$ can join together to form an optionally substituted hetero cyclic ring, and
X is O or S.

The method can further comprise providing a solution comprising a secondary amine $R^3R^4NH$ (e.g., wherein $R^3$ and $R^4$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, and $R^2$ and $R^3$ can join together to form an optionally substituted heterocyclic ring) and an amine halogenating reagent; adding a compound of formula I to said solution to carry out a first electrophilic amination reaction; adding a nucleophilic reagent $HNR^6R^7$ or $HXR^1$ (e.g., where $R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl, and, in certain embodiments, $R^6$ and $R^7$ can join together to form an optionally substituted hetero cyclic ring), and a base to reaction mixture of the first electrophilic amination reaction to carry out a second nucleophilic reaction; and adding a reducing reagent to reaction mixture of said second nucleophilic reaction to carry out a third enamine reduction reaction to provide the compound of formula II.

The methods hereof can be used to produce a broad range of carbon-substituted piperazine products and/or β-, γ-amino acid derivatives. Functional groups including (without limitation) bromide, CF3, NO2, free alcohol, Boc-carbamate, olefin, cyclopropyl group, and heteroaromatics (e.g., quinonine, pyridine, furan, pyrrole, indole, and thiophene) are all well tolerated under the mild reaction conditions of such methods. Further, a tosyl group can be switched to other sulfonamide groups, including the readily removable nosyl group. In addition to other allenyl esters, allenyl ketone, nitrile, sulfone, phosphine oxide, and phosphanate can be used as the unsaturated R-system for the amphoteric deamination cyclization to afford piperazines with a diverse substituent on C2. Additionally, the introduction of sulfone, phosphine oxide, and phosphanate into the piperazine products can provide opportunities for further structural diversifications via various olefination reactions.

The methods hereof can produce piperazines with more than one carbon-substitution. For example, and without limitation, for the case of 2,6-disubstituted piperazines, after the one-pot reduction step (e.g., using NaBH$_3$CN), instead of producing the 2,6-cis products with two equatorial substituents, which are often produced as the predominant products especially with nitrogen-unprotected cases, the more challenging 2,6-trans substituted products can be obtained as the major products.

The trans-selectivity can be achieved using the methods hereof (associated, in particular, with the reduction step presumably due to an axial hydride attack on the iminium ion intermediate formed under acidic conditions). For example, an iminium ion conformer can be favored because it does not suffer from strong steric interaction between the C-Me and N-Me groups.

For the case of 2,5-substituted piperazines, instead of getting the 2,5-trans substitution patterns where the two substituents are equatorially oriented, 2,5-cis substituted products can be obtained using the methods hereof. Further, the methods hereof enable ready access of 2,6-trans or 2,5-cis substituted piperazines, which are otherwise challenging to synthesize.

Further, the methods hereof can be used to produce bicyclic piperazine products, for example, having a 2,6-cis and/or 2,5-trans stereochemical relationship. In these cases, the bicyclic ring systems can lock the conformation and the major product can be achieved through an axial hydride attack.

Compounds produced from the methods hereof are also provided. In certain embodiments, a compound of formula II made by any method of synthesizing a compound of formula II from a compound of formula I is provided. In certain embodiments, the compounds produced from the deamination methods hereof can possess one or more of the following activities: antibacterial, antifungal, antiviral, anticancer, and antiparasitic activity.

In certain embodiments, a compound produced from the methods hereof comprises a structure of Formula (III):

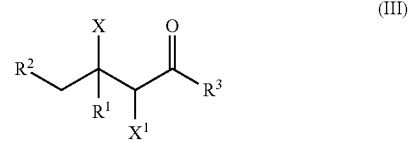

or is a pharmaceutically acceptable salt thereof, wherein
$R^1$ is D or absent;
$R^2$ is

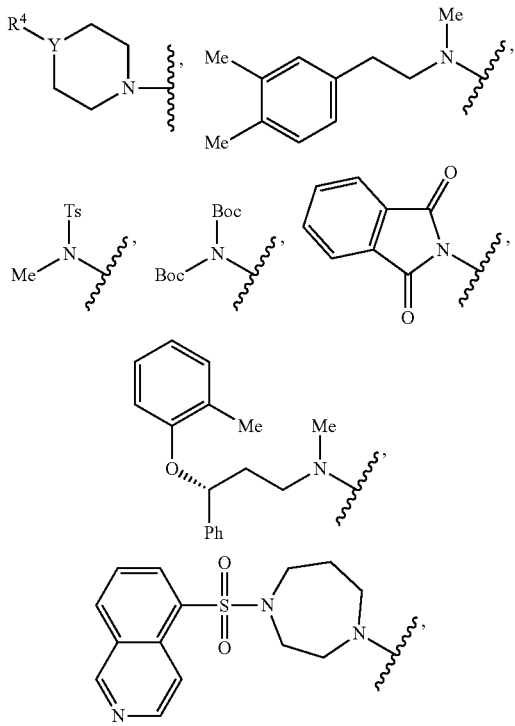

-continued
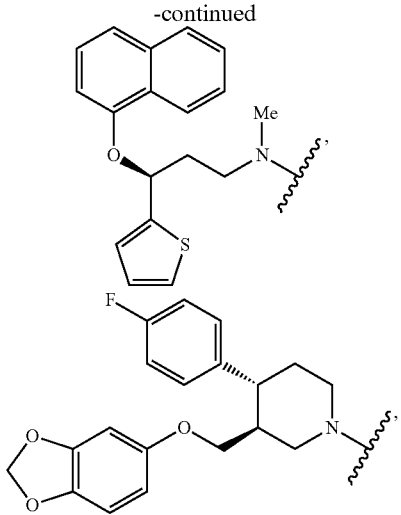
wherein:
Y is N, S, C, or O, and
R⁴ is Ph,
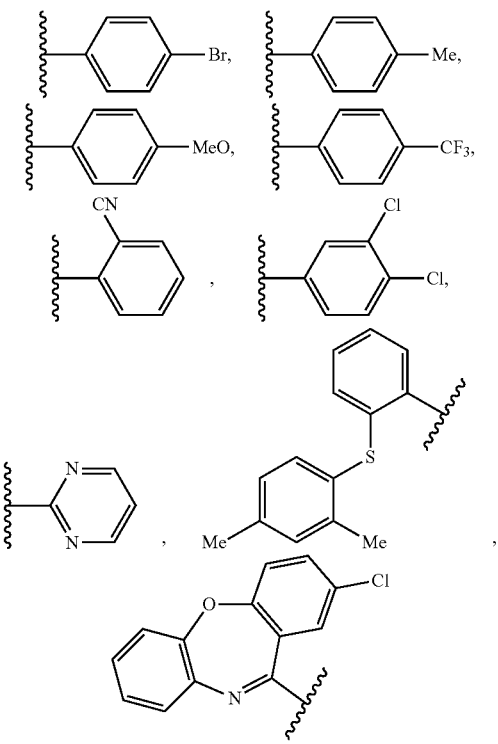
or
absent;
R³ is OBn, OEt,
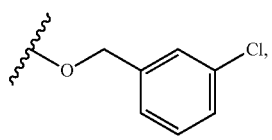
-continued
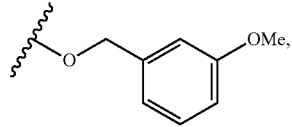
X is
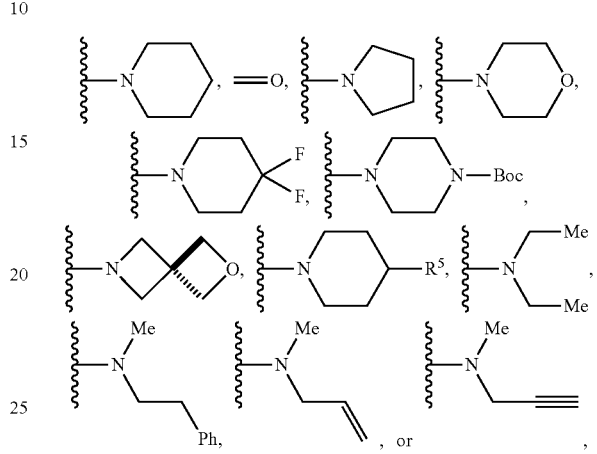
wherein
R⁵ is Ph or COOMe; and
X¹ is absent or F.
In certain embodiments, a compound produced from the methods hereof comprises a structure of Formula (IV):
$$\text{(IV)}$$
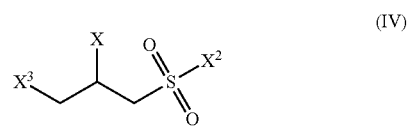
or is a pharmaceutically acceptable salt thereof, wherein
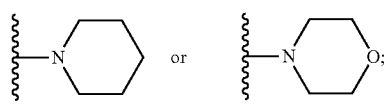
X is Ph,
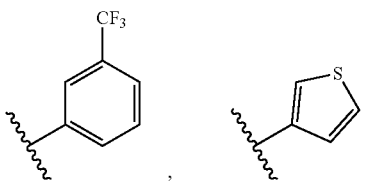
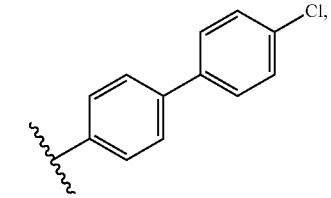
or -continued
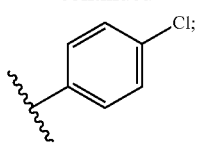
and
X³ is
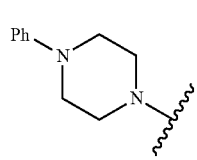 or 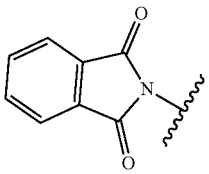.
In certain embodiments, a compound produced from the methods hereof comprises a structure of Formula (V):
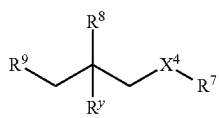  (V)
or is a pharmaceutically acceptable salt thereof, wherein:
X is O or S;
R⁷ is
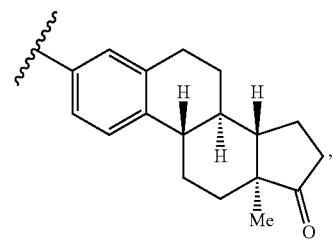,
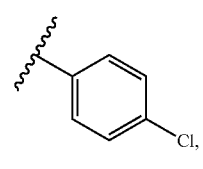, 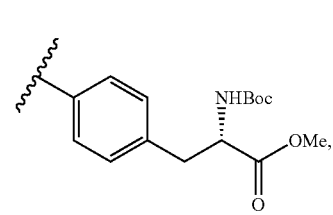,
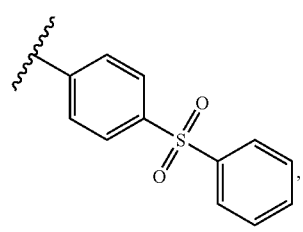,
-continued
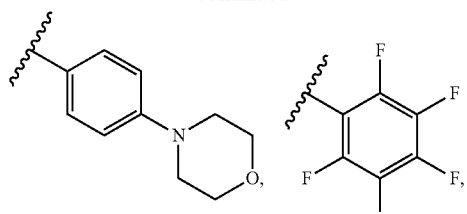
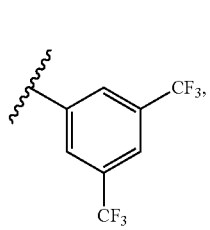 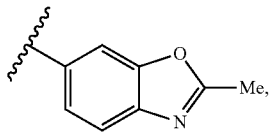
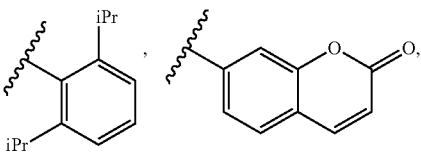
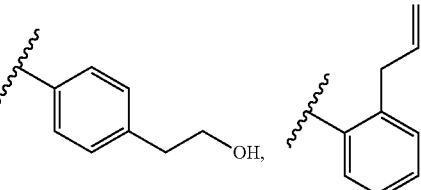
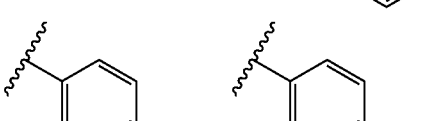
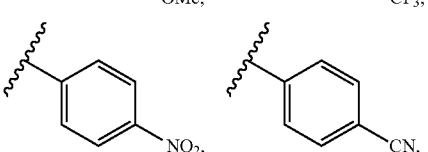
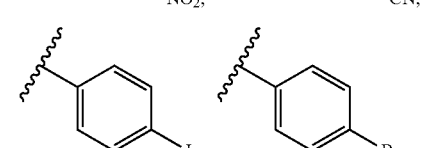
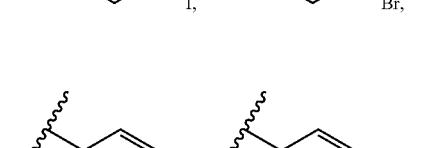
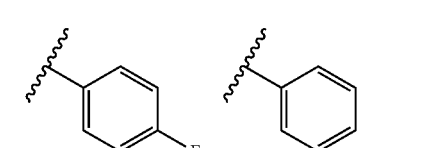
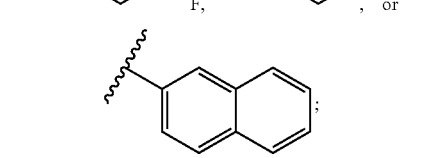

$R^8$ is

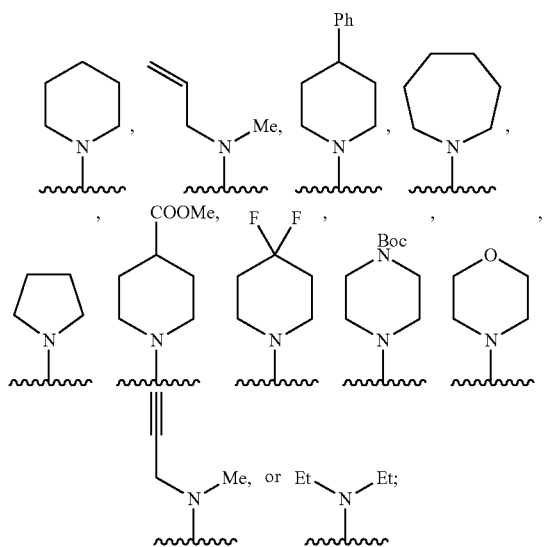

$R^9$ is

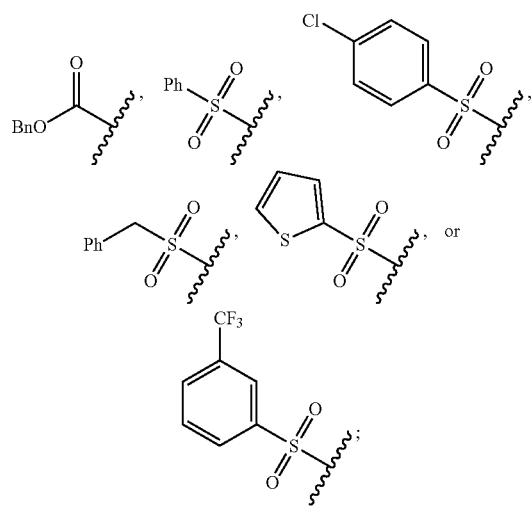

and $R^y$ is absent or D.

Specific exemplary methods and compounds hereof are described in additional detail below.

EXAMPLES

Example 1

Reagents and Preparation of Starting Materials

Reagents

All reagents were used as received from commercial sources unless specified otherwise or prepared as described in the literature. Anhydrous tetrahydrofuran (THF) and toluene were distilled over sodium and diphenylketone under Argon. Anhydrous $CH_2Cl_2$ and $CH_3CN$ were distilled over calcium hydride under Argon. Analytical thin layer chromatography (TLC) was done on pre-coated silica gel plates. Organic solutions were concentrated under reduced pressure on a Büchi rotary evaporator. Oil bath was used for reaction heating. Product purification was performed by flash column chromatography with silica gel (200-300 mesh). $^1H$, $^{13}C$, $^{19}F$ NMR spectra were recorded on a 500 MHz instrument. Data are reported in the following format: chemical shift in ppm, multiplicity (s=singlet, d=doublet, t=triplet, q=quartet, bs=broad singlet, m=multiplet, dd=doublet of doublets, etc.), coupling constant J in Hz, and integration. $CDCl_3$ was used as received. NMR chemical shifts are reported in ppm relative to $CDCl_3$ (7.26 ppm $^1H$ and 77.2 ppm $^{13}C$). Partial ionizing radiation (IR) spectra were reported. Gas chromatography-mass spectrometry (GC-MS) analyses were performed on a GC-MS with an electron ionization (EI) mode. High-resolution mass spectrometry (HRMS) were obtained using electrospray ionization (ESI) on a time of flight (TOF) mass spectrometer.

Preparation of Starting Materials

Various starting materials are shown in Table 1 below.

TABLE 1

| Starting Material Compounds | |
|---|---|
| ![acrylate OBn] | 2 |
| ![acrylate OEt] | A1 |
| ![3-chlorobenzyl acrylate] | A2 |
| ![3-methoxybenzyl acrylate] | A3 |
| ![2-fluoro ethyl acrylate] | A4 |
| ![vinyl sulfone Ph] | A5 |
| ![vinyl sulfone 3-CF3-Ph] | A6 |
| ![vinyl sulfone thienyl] | A7 |

TABLE 1-continued

Starting Material Compounds

A8: [vinyl sulfonyl biphenyl chloride structure]

A9: [vinyl sulfonyl phenyl chloride structure]

[Three N-chloroamine structures: N-chloropiperidine, N-chloromorpholine, N-chloro-4-phenylpiperidine]

N-chloroamines

Allenoates 2, A1, A2, A3 of Table 1 were each synthesized according to literature procedures. See Rout and Harned, Chem. Eur. J. 15: 12926-12928 (2009); Huang et al., Org. Lett. 19: 3524-3527 (2017). N-chloroamines were synthesized according to literature procedure. See Monaco et al., Org. Lett. 13: 4546-4549 (2011).

Allenoate A4 was synthesized according to the following procedure. In a 20.0 mL flame dried vial, ethyl 2-bromo-2-fluoroacetate (1.8 g, 9.7 mmol) and PPh$_3$ (2.81 g, 10.7 mmol) were dissolved in 7.0 mL anhydrous dichloromethane (DCM). The vial was capped and sealed by parafilm and wrapped by aluminum foil. The reaction was stirred for 5 days and diluted with 30.0 mL anhydrous DCM. At 0° C., Et$_3$N was added and the reaction was stirred for 2 hours at room temperature. The reaction was cooled to −40° C., AcCl (917 mg, 11.7 mmol) was added drop-wise, and the reaction was stirred at −40° C. for 12 hours. The solution was directly passed through a silica gel plug and washed down by 10% Et$_2$O in pentane. Then, the crude solution was concentrated under vacuum in an ice bath and purified by flash column (1-2% Et$_2$O in pentane). $^1$H NMR (500 MHz, CDCl$_3$) δ 5.91 (s, 2H), 4.30 (q, J=7.1 Hz, 2H), 1.32 (t, J=7.1 Hz, 3H); $^{13}$C NMR (126 MHz, CDCl$_3$) δ 201.6 (d, J=22.8 Hz), 161.6 (d, J=38.5 Hz), 131.7 (d, J=238.3 Hz), 96.0 (d, J=8.6 Hz), 62.2, 14.3; $^{19}$F NMR (471 MHz, CDCl$_3$) δ −157.61; GCMS (EI) m/z 130 [M]$^+$; FTIR (neat) ν$_{max}$ 2985, 2919, 1768, 1723, 1372, 1312, 1180, 1094, 1017, 945, 771 cm$^{-1}$. While different ionization and detection methods were attempted, the HRMS of allenoate A4 was not obtained.

Example 2

Diamination Reaction

General Procedure A for Diamination: To an oven-dried 10 mL vial wrapped with aluminum foil and equipped with a stir bar was added the indicated amine (0.11 mmol, 1.1 equiv), t-BuOCl (14.0 µL, 0.12 mmol, 1.2 equiv), and CH$_3$CN (2.0 mL) under argon atmosphere. The reaction mixture was stirred for 1 hour at room temperature. Then, tetrabutylammonium iodide (TBAI, 55.4 mg, 0.15 mmol, 1.5 equiv), allenoate (0.1 mmol, 1.0 equiv) was added and the reaction mixture was stirred for 4-8 hours (the conversion of allenoate was monitored by TLC). After the indicated time, Cs$_2$CO$_3$ (48.9 mg, 0.15 mmol, 1.5 equiv) and the indicated amine (0.15 mmol, 1.5 equiv) was added. The reaction mixture was stirred for 24 hours at room temperature. Subsequently, NaBH$_3$CN (0.2 mmol) and a co-solvent of MeOH/AcOH (pH=4, 1.0 mL) were added to the reaction mixture. After 1.5 hours at room temperature (rt), the reaction was quenched with a saturated aqueous solution of NaHCO$_3$, extracted with CH$_2$Cl$_2$ for three times. The combined organic extracts were dried over Na$_2$SO$_4$, filtered, and concentrated under reduced pressure. The resulting crude mixture was purified by flash column chromatography on silica gel (hexanes/EtOAc/Et$_3$N) to afford the desired compound.

General Procedure B for Diamination: To an oven-dried 10 mL vial wrapped with aluminum foil and equipped with a stir bar was added allenoate (0.1 mmol, 1.0 equiv), N-chloroamine (0.11 mmol, 1.1 equiv), tetrabutylammonium iodide (TBAI, 55.4 mg, 0.15 mmol, 1.5 equiv) and CH$_3$CN (2.0 mL) under argon atmosphere. The reaction mixture was stirred for 4-8 hours at room temperature (the conversion of allenoate was monitor by TLC). After the indicated time, Cs$_2$CO$_3$ (48.9 mg, 0.15 mmol, 1.5 equiv) and the indicated amine was added. The reaction mixture was then stirred for 24 hours at rt. Subsequently (X=H), NaBH$_3$CN (0.2 mmol) and a co-solvent of MeOH/AcOH (pH=4, 1.0 mL) were added to the reaction mixture. After 1.5 hour at rt, the reaction was quenched with a saturated aqueous solution of NaHCO$_3$, extracted with CH$_2$Cl$_2$ for three times. Or, subsequently (X=F), the reaction mixture was cooled to −20° C. before NaBH$_3$CN (0.2 mmol) and a co-solvent of EtOH/AcOH (pH=4, 1.0 mL) were added to the reaction mixture. After 1.5 hours at −20° C., the reaction was quenched with a saturated aqueous solution of NaHCO$_3$, extracted with CH$_2$Cl$_2$ for three times. The combined organic extracts were dried over Na$_2$SO$_4$, filtered, and concentrated under reduced pressure. The resulting crude mixture was purified by flash column chromatography on silica gel (hexanes/EtOAc/Et$_3$N) to afford the desired compound.

Example 3

Optimization of Deamination Reaction

Figure 2A:
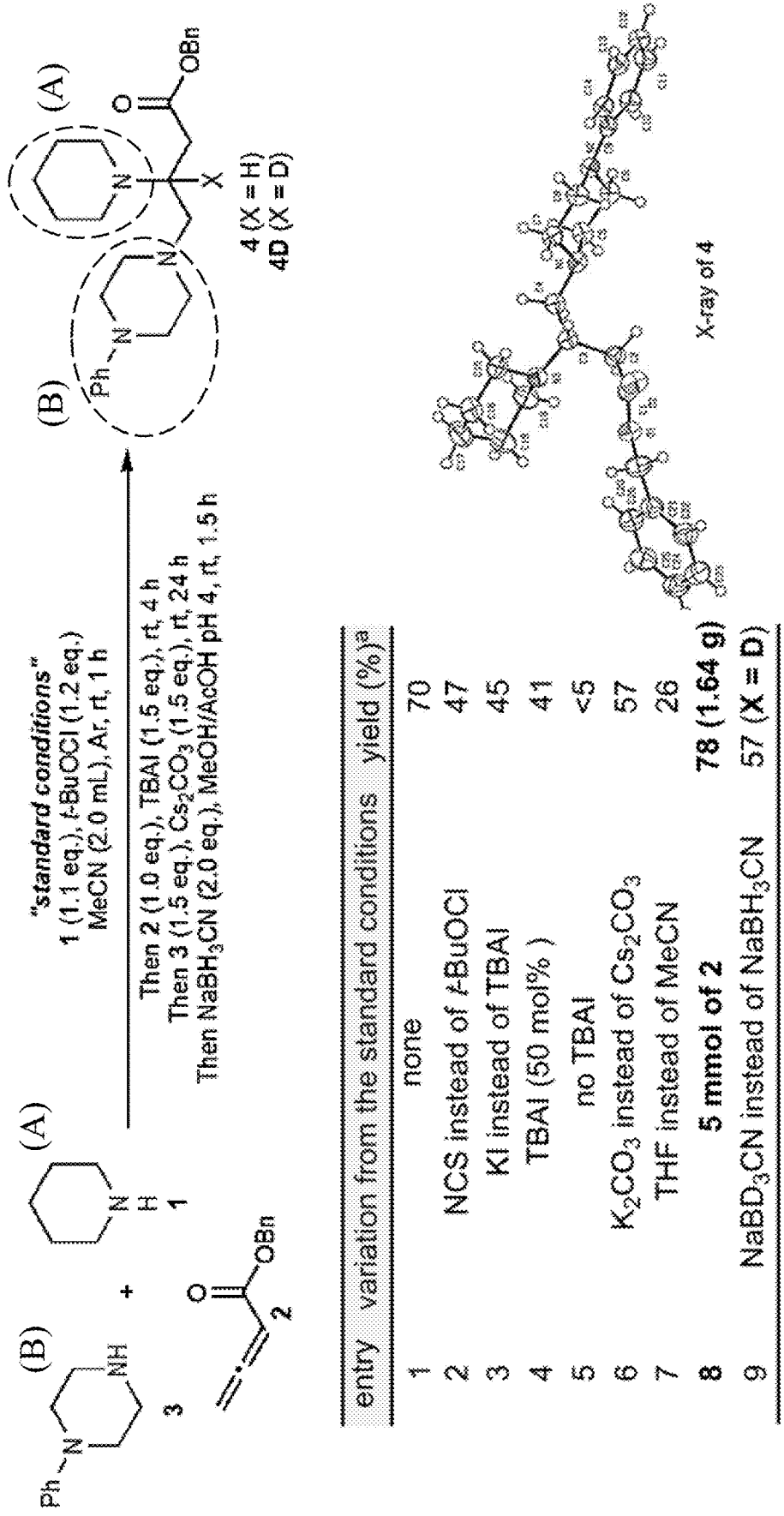
FIG. 2A illustrates an optimization of key one-pot reaction parameters and/or conditions of the present methods.

Studies were performed to optimize the reaction. As shown in FIG. 2A, the deamination method began with benzyl allenoate 2 and two different cyclic amines: piperidine 1 and 1-phenylpiperazine 3. Initially, one-pot 1,4-diazo heterocycle synthesis protocols were employed using NCS and NIS and, while the formation of desired product 4 was detected after a one-pot reduction, the reaction was quite messy. Namely, the succinimide derived from NIS/NCS further complicated the reaction by competing with amine 3 for the substitution process.

To address this, NIS and NCS were replaced as the oxidizing reagents to generate the corresponding electrophilic iodo/chloroamines. Primarily, NIS/NCS was replaced with t-BuOCl, which is an effective reagent to convert alkylamines to chloramines, and the byproduct is tert-butanol (t-BuOH), a bulky and relatively inert alcohol for nucleophilic substitution reactions. The use of t-BuOCl was accompanied by the use of TBAI in combination therewith. TBAI can be more effective than an inorganic iodide source including KI (entry 3 in FIG. 2A), presumably due to its better solubility in acetonitrile. The data supported that replacing NIS and NCS with t-BuOCl resulted in a much cleaner reaction.

Perhaps more specifically, allenes A6, A7, A8 and A9 (as shown in Table 1) were synthesized according to the following three-component deamination procedure.

The corresponding thiophenol (1.0 equiv.) and acetic acid (1.0 equiv.) were mixed in an 8 mL vial with stir bar and the solution was cooled to −40° C. Sulfuryl chloride (2.0 equiv.) was added dropwise at this temperature to the frozen mixture. After completing addition, the reaction mixture was stirred at −40° C. for 30 minutes and slowly increased to room temperature and then stirred for another 3 hours.

The solution was concentrated to give a crude product, which was dissolved in THF and cooled to −78° C. Propargylic alcohol (1.0 equiv.) was added followed by diisopropylethylamine (1.2 equiv.). The reaction was stirred at −78° C. for 2 hours and quenched with water. The organic layer was extracted by EtOAc and dried over $Na_2SO_4$. After filtration, the organic layer was concentrated and purified by column chromatography to afford the corresponding sulfinic ester as colorless oil, which was dissolved in anhydrous DCM and catalytic amount of $AgSbF_6$ (2 mol %) was added. The reaction was monitored by TLC. After reaction was completed, solvent was removed, and the crude product was purified by column chromatography to afford allenyl sulfone A6-A9 as white solid. After a one-pot reduction, product 4 was produced (e.g., in 70% yield with the combination of t-BuOCl and TBAI (entry 1 in FIG. 2A)).

Notably, without TBAI, the yield was lower than 5% (entry 5 in FIG. 2A) and when its amount was reduced from 1.5 equiv. to 0.5 equiv., the yield dropped to 41% (entry 4 in FIG. 2A). Similar to 1,4-diazo heterocycle synthesis, $Cs_2CO_3$ was superior to other bases including $K_2CO_3$ (entry 6 in FIG. 2A) and THF was less effective than acetonitrile as solvent (entry 7 in FIG. 2A). Furthermore, when the reaction was conducted at 5 mmol scale, product 4 was obtained in even higher yield (78%, 1.64 gram). Additionally, when $NaBD_3CN$ was used as the reducing reagent, a deuterium atom can be introduced at the β-position of 4 directly (entry 9 in FIG. 2A).

Example 4

Identification of Key Intermediates

Figure 2B:
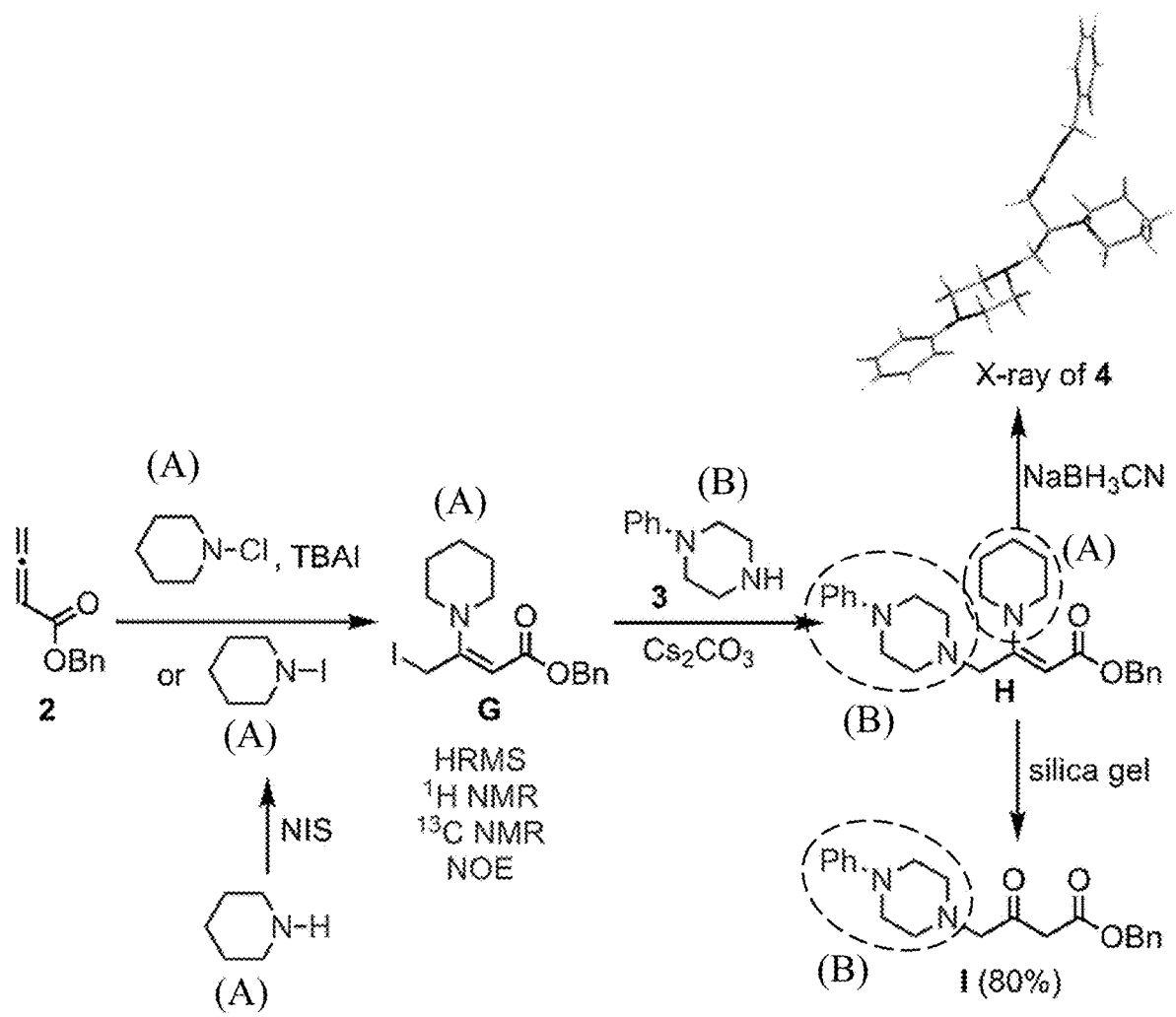
FIG. 2B identifies key intermediates of the present methods.

To probe the reaction mechanism of the method, investigations were conducted to identify and characterize key intermediates involved in the reaction process (FIG. 2B). N-chloropiperidine was prepared and purified, then reacted with allenoate 2 in the presence of TBAI. More specifically, allenoate 2 (17.4 mg, 0.1 mmol, 1.0 equiv), N-chloropiperidine (13.1 mg, 0.11 mmol, 1.1 equiv), tetrabutylammonium iodide (TBAI, 55.4 mg, 0.15 mmol, 1.5 equiv) and $CH_3CN$ (2.0 mL) were added under argon atmosphere to an oven-dried 10 mL vial wrapped with aluminum foil and equipped with a stir bar. The reaction mixture was stirred for 4 hours at room temperature before passing through a celite plug to remove solid. The solvent was removed under vacuum and the crude product was dissolved in 0.5 mL $CD_3CN$ for NMR studies. The identity of allylic iodide G was confirmed by NMR, HMQC, NOESY and HRMS analyses of the crude mixture. (Note: The same allylic iodide was obtained when 2 was treated with N-iodopiperidine generated in situ from piperidine and NIS). HRMS spectrum of G (ESI/[M+H]$^+$) calcd. for $C_{16}H_{21}INO_2^+$: 386.0611, found [M+H]$^+$: 386.0612.

The formation of an unstable allylic iodide E was observed and characterized using high-resolution mass spectrometry (HRMS) and nuclear magnetic resonance (NMR). The same allylic iodide was obtained when 2 was treated with N-iodopiperidine generated in situ from piperidine and NIS.

For the preparation of intermediate H, allenoate 2 (17.4 mg, 0.1 mmol, 1.0 equiv), N-chloropiperidine (13.1 mg, 0.11 mmol, 1.1 equiv), tetrabutylammonium iodide (TBAI, 55.4 mg, 0.15 mmol, 1.5 equiv) and $CH_3CN$ (2.0 mL) were added under argon atmosphere to an oven-dried 10 mL vial wrapped with aluminum foil and equipped with a stir bar. The reaction mixture was stirred for 4 hours at rt. $Cs_2CO_3$ (48.9 mg, 0.15 mmol, 1.5 equiv) and 1-phenylpiperazine 3 (24.3 mg, 0.15 mmol, 1.5 equiv) was added. The reaction mixture was then stirred for 24 hours at room temperature. The reaction mixture was passed through a celite plug to remove the solid. The solvent was removed under vacuum to give a crude product. The crude product was passed through a column of neutral $Al_2O_3$ to provide crude intermediate H.

The identity of product H was confirmed by NMR and HRMS analyses. (Note: Because the intermediate H can be hydrolyzed to generate I by silica gel column purification, $Al_2O_3$ column chromatography was used to isolate H; however, the intermediate H was very unstable during the NMR analysis process and underwent hydrolysis during silica gel column purification to produce γ-amino-O-ketoester I.). HRMS spectrum of H (ESI/[M+H]$^+$) calcd. for $C_{26}H_{34}N_3O_2^+$: 420.2646, found [M+H]$^+$: 420.2645. Therefore, the aforementioned one-pot reduction using $NaBH_3CN$ was carried out to produce β,γ-diamino acid derivative 4. The structure of 4 was unambiguously established by X-ray crystallographic analysis (CCDC 2004609).

Example 5

Scope of Substrates of Deamination

Figure 3:
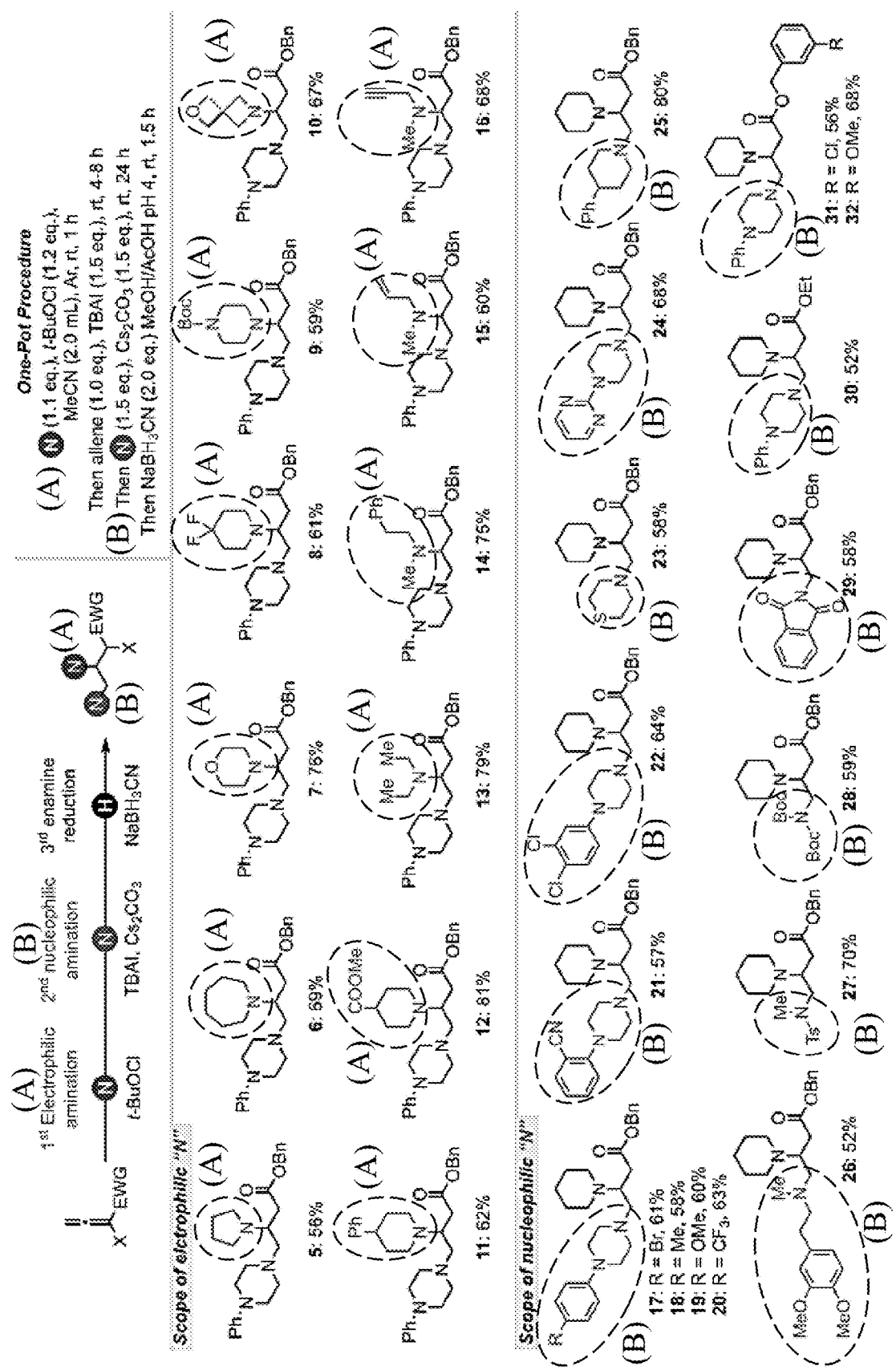
FIG. 3 illustrates substrates that can be produced using the present methods, with $^a$indicating $NaBH_3CN$ (2.0 eq.), EtOH/AcOH, pH 4, −20° C. for 1.5 hours; $^b$indicating a ratio was determined by $^{19}F$ nuclear magnetic resonance (NMR) of the crude reaction mixture; $^b$indicating purified N-chloroamine was used; $^d$indicating $NaBD_3CN$ (2.0 eq.), EtOH/AcOH, pH 4, −20° C. for 1.5 hours; and $^e$indicating a ratio was determined by $^1H$ NMR of the crude reaction mixture; and with an amine group from the first electrophilic amination labeled (A) and an amine group from the second nucleophilic amination labeled (B).
Figure 3:
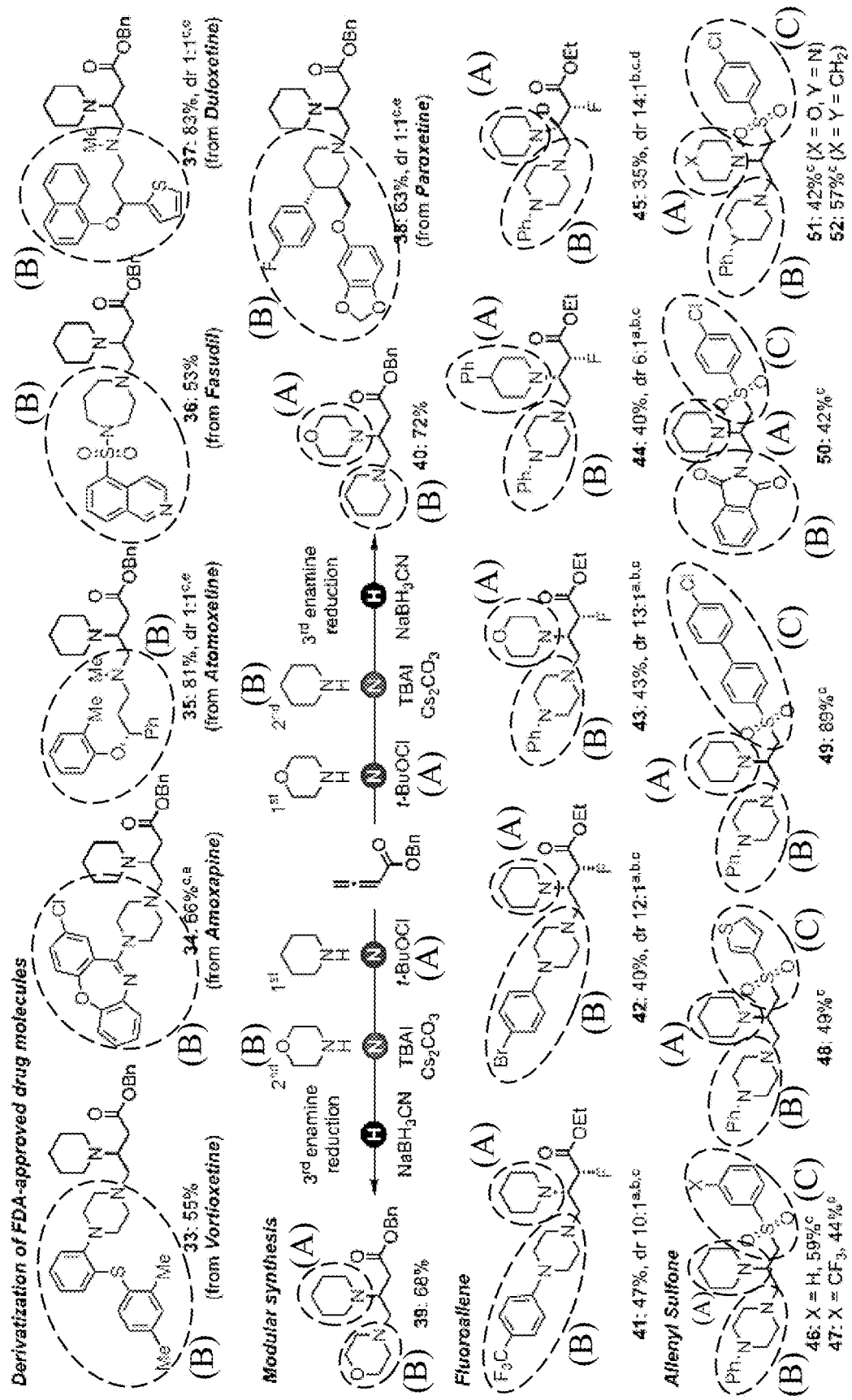

With a better understanding of the reaction process, the scope of substrates that can be produced using the method was investigated (FIG. 3). Both cyclic and acyclic aliphatic amines can be used as the electrophilic amines. The effective cyclic amines include, for example, a wide range of saturated N-heterocycles such as pyrrolidine, piperidine, piperazine, azepane, morpholine, and azetidine, which are often found in U.S FDA-approved drug molecules. The acyclic are represented by diethyl amine, N-methyl-2-phenylethan-1-amine, an allylic amine, and a propargylic amine and others.

The survival of a terminal olefin and a terminal alkyne testifies the mildness of the reaction conditions.

The scope of the nucleophilic amine is even broader. In addition to cyclic and acyclic aliphatic amines, sulfonamide, carbamate, and imide worked smoothly as well. The reaction resulting from the methods hereof features excellent functional group tolerability. For example, Boc-carbamate, ester, olefin, alkyne, nitrile, sulfide, and pyrimidine are all compatible with the mild reaction conditions.

Currently, the allenoate scope is relatively limited. While different alkyl groups were tolerated on the carboxylate, the reaction was sensitive to substituents on the α-carbon and γ-carbon of the allenoates. To date, only small fluorine atom were tolerated at the α-position of the allenoates, which led to the formation of α-fluoro-β,γ-diamino acid derivatives with modest reaction yield and excellent diastereoselectivity. For these cases, the use of the corresponding purified chloroamines gave better reaction results than the in-situ generation of the chloroamines.

Further, conducting the NaBH₃CN reduction at a lower temperature (−20° C.) in a mixture of EtOH and AcOH obtained high diastereoselectivity. The relative stereochemistry of 44 was determined by X-ray crystallographic analysis (CCDC 2004611). The stereochemistry of the reduction step could be explained by the polar Felkin-Anh model. When NaBD₃CN was used as the reducing reagent, a remarkably functionalized α-fluoro-β-deutero-β,γ-diamino carboxylate was produced in just one step (compound 45). The successful use of α-fluoroallenoates provides an efficient method to prepare fluorine-containing molecules, which are important in drug discovery.

Notably, complex U.S. FDA-approved secondary amine-containing drugs such as vortioxetine, amoxapine, atomoxetine, fasudil, duloxetine, and paroxetine can be used as the nucleophilic partners, which provides an efficient way to incorporate these lifesaving drug molecules into more complex structures to tune or repurpose their function. More importantly, the position of the amines in the final product can be switched by simply alternating the addition order of the two amines. For example, both compounds 39 and 40 could be prepared in good yield by changing the addition order of piperidine and morpholine. This modular feature would enable rapid synthesis of analogs without inventing another synthetic approach and is believed to be useful for structure-activity relationship studies.

Example 6

Characterization Data for Compounds from FIGS. 2 and 3

Benzyl 4-(4-phenylpiperazin-1-yl)-3-(piperidin-1-yl)butanoate (compound 4)

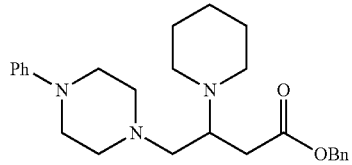 [SMILES: O=C(CC(CN1CCN(c2ccccc2)CC1)N1CCCCC1)OCc1ccccc1]

Compound 4 was prepared using the general procedure A (see Example 2 supra), using allenoate 2 (17.4 mg, 0.1 mmol, 1.0 equiv), piperidine (11.0 µL, 0.11 mmol, 1.1 equiv) and 1-phenylpiperazine (24.3 mg, 0.15 mmol, 1.5 equiv). The reaction time of the electrophilic amination step was 4 hours. The product was isolated by silica gel chromatography as a colorless oil (0.1 mmol scale 29.5 mg, 70% yield; 5 mmol scale 1.64 g, 78%).

¹H NMR (500 MHz, CDCl₃) δ 7.38-7.22 (m, 7H), 6.94-6.87 (m, 2H), 6.84 (t, J=7.3 Hz, 1H), 5.17-5.04 (m, 2H), 3.36-3.26 (m, 1H), 3.17-3.04 (m, 4H), 2.76-2.69 (m, 2H), 2.62-2.35 (m, 10H), 1.57-1.46 (m, 4H), 1.44-1.36 (m, 2H); ¹³C NMR (126 MHz, CDCl₃) δ 173.1, 151.5, 136.3, 129.2, 128.6, 128.3, 128.2, 119.6, 116.1, 66.2, 60.0, 59.4, 53.8, 50.2, 49.3, 35.4, 26.6, 24.9; HRMS (ESI/[M+H]⁺) calcd. for C₂₆H₃₆N₃O₂⁺: 422.2802, found [M+H]⁺: 422.2802; FTIR (neat) $v_{max}$ 2933, 2810, 1733, 1599, 1495, 1453, 1233, 1010, 757, 695 cm⁻¹.

Benzyl 4-(4-phenylpiperazin-1-yl)-3-(piperidin-1-yl)butanoate-3-d (compound 4D)

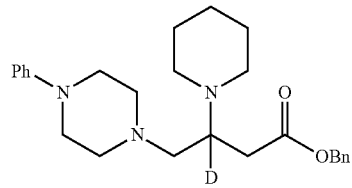 [SMILES: [2H]C(CC(=O)OCc1ccccc1)(CN1CCN(c2ccccc2)CC1)N1CCCCC1]

Compound 4D was prepared following the general procedure A (see Example 2 supra) using allenoate 2 (17.4 mg, 0.1 mmol, 1.0 equiv), piperidine (11.0 µL, 0.11 mmol, 1.1 equiv) and 1-phenylpiperazine (24.3 mg, 0.15 mmol, 1.5 equiv). The reaction time of the electrophilic amination step was 4 hours. NaBD₃CN was used instead of NaBH₃CN. Compound 4D was isolated by silica gel chromatography as a colorless oil (24.2 mg, 57% yield).

¹H NMR (500 MHz, CDCl₃) δ 7.40-7.29 (m, 5H), 7.28-7.23 (m, 2H), 6.90 (d, J=7.9 Hz, 2H), 6.84 (t, J=7.3 Hz, 1H), 5.16-5.06 (m, 2H), 3.16-3.03 (m, 4H), 2.78-2.67 (m, 2H), 2.61-2.33 (m, 10H), 1.55-1.48 (m, 4H), 1.43-1.37 (m, 2H); ¹³C NMR (126 MHz, CDCl₃) δ 173.1, 151.5, 136.3, 129.2, 128.6, 128.3, 128.2, 119.7, 116.1, 66.3, 59.9, 53.8, 50.1, 49.3, 35.3, 26.6, 24.9. The quaternary carbon connected with deuterium was omitted. HRMS (ESI/[M+H]⁺) calcd. for C₂₆H₃₅DN₃O₂⁺: 423.2865, found [M+H]⁺: 423.2864; FTIR (neat) $v_{max}$ 2934, 2817, 1730, 1599, 1497, 1454, 1233, 1007, 753 cm⁻¹.

Benzyl 3-oxo-4-(4-phenylpiperazin-1-yl)butanoate (intermediate I)

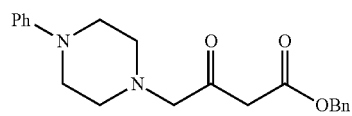 [SMILES: O=C(CC(=O)OCc1ccccc1)CN1CCN(c2ccccc2)CC1]

To an oven-dried 10 mL vial wrapped with aluminum foil and equipped with a stir bar was added allenoate 2 (17.4 mg, 0.1 mmol, 1.0 equiv), N-chloropiperidine (13.1 mg, 0.11 mmol, 1.1 equiv), tetrabutylammonium iodide (TBAI, 55.4 mg, 0.15 mmol, 1.5 equiv) and CH₃CN (2.0 mL) under argon atmosphere. The reaction mixture was stirred for 4 hours at room temperature. After this time, Cs₂CO₃ (48.9 mg, 0.15 mmol, 1.5 equiv) and 1-phenylpiperazine (24.3 mg, 0.15 mmol, 1.5 equiv) was added. The reaction mixture was then stirred for 24 hours at rt. The product was obtained by flash column chromatography on silica gel as a colorless oil (24.2 mg, 80% yield).

¹H NMR (500 MHz, CDCl₃) δ 7.42-7.29 (m, 5H), 7.31-7.22 (m, 2H), 7.06-6.81 (m, 3H), 5.18 (s, 2H), 3.58 (s, 2H), 3.30 (s, 2H), 3.23-3.10 (m, 4H), 2.67-2.56 (m, 4H); ¹³C NMR (126 MHz, CDCl₃) δ 201.9, 167.3, 151.2, 135.4, 129.3, 128.8, 128.7, 128.6, 120.1, 116.3, 67.6, 67.3, 53.5, 49.2, 47.0; HRMS (ESI/[M+H]⁺) calcd. for C₂₁H₂₅N₂O₃⁺: 353.1860, found [M+H]⁺: 353.1861; FTIR (neat) $v_{max}$ 2931, 2823, 1744, 1720, 1599, 1497, 1453, 1383, 1307, 1231, 753, 696 cm⁻¹.

Benzyl 4-(4-phenylpiperazin-1-yl)-3-(pyrrolidin-1-yl)butanoate (compound 5)

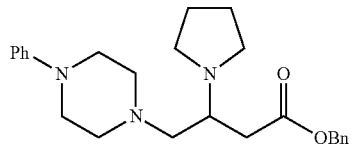 [SMILES: O=C(CC(CN1CCN(c2ccccc2)CC1)N1CCCC1)OCc1ccccc1]

Compound 5 was prepared following the general procedure A (see Example 2 supra) using allenoate 2 (17.4 mg, 0.1 mmol, 1.0 equiv), pyrrolidine (9.0 μL, 0.11 mmol, 1.1 equiv) and 1-phenylpiperazine (24.3 mg, 0.15 mmol, 1.5 equiv). The reaction time of the electrophilic amination step was 4 h. The product was isolated by silica gel chromatography as a colorless oil (22.8 mg, 56% yield).

$^1$H NMR (500 MHz, CDCl$_3$) δ 7.38-7.22 (m, 7H), 6.90 (d, J=8.1 Hz, 2H), 6.85 (t, J=7.3 Hz, 1H), 5.18-5.05 (m, 2H), 3.29-3.19 (m, 1H), 3.16-3.06 (m, 4H), 2.75-2.69 (m, 2H), 2.67-2.56 (m, 7H), 2.55-2.47 (m, 1H), 2.43 (dd, J=12.3, 9.8 Hz, 1H), 1.74 (bs, 4H); $^{13}$C NMR (126 MHz, CDCl$_3$) δ 173.0, 151.5, 136.2, 129.2, 128.6, 128.32, 128.25, 119.6, 116.1, 66.3, 61.8, 57.0, 53.9, 50.3, 49.3, 36.8, 23.5; HRMS (ESI/[M+H]$^+$) calcd. for C$_{25}$H$_{34}$N$_3$O$_2$$^+$: 408.2646, found [M+H]$^+$: 408.2635; FTIR (neat) ν$_{max}$ 2959, 2817, 1731, 1599, 1500, 1454, 1232, 1135, 1009, 756, 691 cm$^{-1}$.

Benzyl 3-(azepan-1-yl)-4-(4-phenylpiperazin-1-yl)butanoate (compound 6)

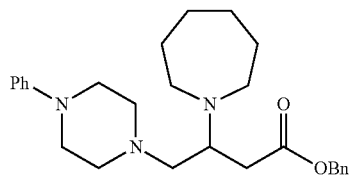 [SMILES: O=C(CC(CN1CCN(c2ccccc2)CC1)N1CCCCCC1)OCc1ccccc1]

Compound 6 was prepared following the general procedure A (see Example 2 supra) using allenoate 2 (17.4 mg, 0.1 mmol, 1.0 equiv), azepane (12.0 μL, 0.11 mmol, 1.1 equiv) and 1-phenylpiperazine (24.3 mg, 0.15 mmol, 1.5 equiv). The reaction time of the electrophilic amination step was 7 hours. The product was isolated by silica gel chromatography as a colorless oil (30.1 mg, 69% yield).

$^1$H NMR (500 MHz, CDCl$_3$) δ 7.41-7.30 (m, 5H), 7.29-7.24 (m, 2H), 6.94-6.90 (m, 1H), 6.88-6.83 (m, 1H), 5.18-5.07 (m, 2H), 3.44-3.35 (m, 1H), 3.20-3.06 (m, 4H), 2.77-2.66 (m, 4H), 2.66-2.59 (m, 2H), 2.57-2.46 (m, 4H), 2.40-2.28 (m, 1H), 1.66-1.46 (m, 8H); $^{13}$C NMR (126 MHz, CDCl$_3$) δ 173.1, 151.5, 136.3, 129.2, 128.6, 128.4, 128.2, 119.6, 116.0, 66.3, 60.4, 59.8, 53.8, 51.6, 49.3, 36.7, 30.0, 27.0; HRMS (ESI/[M+H]$^+$) calcd. for C$_{27}$H$_{38}$N$_3$O$_2$$^+$: 436.2959, found [M+H]$^+$: 436.2950; FTIR (neat) ν$_{max}$ 2924, 2818, 1731, 1599, 1500, 1453, 1231, 1135, 1008, 756, 694 cm$^{-1}$.

Benzyl 3-morpholino-4-(4-phenylpiperazin-1-yl)butanoate (compound 7)

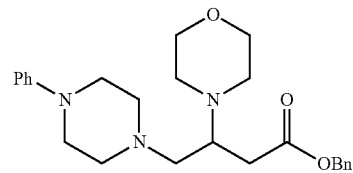 [SMILES: O=C(CC(CN1CCN(c2ccccc2)CC1)N1CCOCC1)OCc1ccccc1]

Compound 7 was prepared following the general procedure A (see Example 2 supra) using allenoate 2 (17.4 mg, 0.1 mmol, 1.0 equiv), morpholine (10.0 μL, 0.11 mmol, 1.1 equiv) and 1-phenylpiperazine (24.3 mg, 0.15 mmol, 1.5 equiv). The reaction time of the electrophilic amination step was 7 hours. The product was isolated by silica gel chromatography as a colorless oil (32.2 mg, 76% yield).

$^1$H NMR (500 MHz, CDCl$_3$) δ 7.39-7.29 (m, 5H), 7.29-7.23 (m, 2H), 6.93-6.89 (m, 2H), 6.85 (t, J=7.3 Hz, 1H), 5.22-5.06 (m, 2H), 3.62 (t, J=4.6 Hz, 4H), 3.35-3.23 (m, 1H), 3.19-3.08 (m, 4H), 2.76-2.62 (m, 4H), 2.61-2.48 (m, 7H), 2.41-2.31 (m, 1H); $^{13}$C NMR (126 MHz, CDCl$_3$) δ 172.7, 151.4, 136.2, 129.2, 128.7, 128.4, 128.3, 119.7, 116.1, 67.5, 66.4, 59.3, 58.9, 53.7, 49.3, 35.7, 29.8; HRMS (ESI/[M+H]$^+$) calcd. for C$_{25}$H$_{34}$N$_3$O$_3$$^+$: 424.2595, found [M+H]$^+$: 424.2596; FTIR (neat) ν$_{max}$ 2949, 2818, 1731, 1599, 1500, 1497, 1454, 1308, 1232, 1135, 1115, 1009, 756, 695 cm$^{-1}$.

Benzyl 3-(4,4-difluoropiperidin-1-yl)-4-(4-phenylpiperazin-1-yl)butanoate (compound 8)

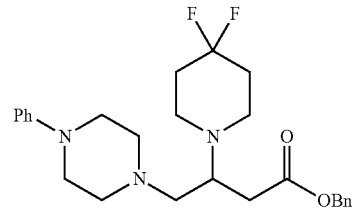 [SMILES: O=C(CC(CN1CCN(c2ccccc2)CC1)N1CCC(F)(F)CC1)OCc1ccccc1]

Compound 8 was prepared following the general procedure A (see Example 2 supra) using allenoate 2 (17.4 mg, 0.1 mmol, 1.0 equiv), 4,4-difluoropiperidine (13.3 mg, 0.11 mmol, 1.1 equiv) and 1-phenylpiperazine (24.3 mg, 0.15 mmol, 1.5 equiv). The reaction time of the electrophilic amination step was 7 h. The product was isolated by silica gel chromatography as a white solid (28.1 mg, 61% yield).

$^1$H NMR (500 MHz, CDCl$_3$) δ 7.40-7.30 (m, 5H), 7.29-7.23 (m, 2H), 6.93-6.89 (m, 2H), 6.86 (tt, J=7.3, 1.1 Hz, 1H), 5.18-5.07 (m, 2H), 3.41 (p, J=7.0 Hz, 1H), 3.13 (td, J=4.6, 4.2, 2.1 Hz, 4H), 2.76 (dt, J=11.5, 5.7 Hz, 2H), 2.68 (dt, J=10.4, 5.0 Hz, 2H), 2.61 (dt, J=11.5, 5.6 Hz, 2H), 2.58-2.44 (m, 5H), 2.34 (dd, J=12.4, 8.9 Hz, 1H), 1.93-1.80 (m, 4H); $^{13}$C NMR (126 MHz, CDCl$_3$) δ 172.5, 151.4, 136.2, 129.2, 128.7, 128.5, 128.4, 122.3 (t, J=241.4 Hz), 119.8, 116.1, 66.4, 59.3, 58.5, 53.7, 49.3, 45.6 (t, J=4.7 Hz), 36.3, 34.7 (t, J=22.4 Hz); $^{19}$F NMR (471 MHz, CDCl$_3$) δ −98.7; HRMS (ESI/[M+H]$^+$) calcd. for C$_{26}$H$_{34}$F$_2$N$_3$O$_2$$^+$: 458.2614, found

[M+H]⁺: 458.2608; FTIR (neat) $v_{max}$ 2941, 2821, 1731, 1599, 1497, 1454, 1360, 1231, 1135, 1091, 1010, 947, 927, 756, 696 cm⁻¹.

tert-Butyl 4-(4-(benzyloxy)-4-oxo-1-(4-phenylpiperazin-1-yl)butan-2-yl)piperazine-1-carboxylate (compound 9)

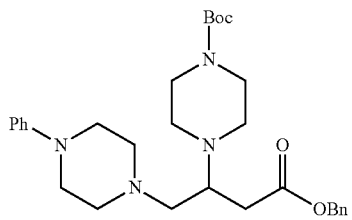 [SMILES: CC(C)(C)OC(=O)N1CCN(C(CC(=O)OCc2ccccc2)CN2CCN(c3ccccc3)CC2)CC1]

Compound 9 was prepared following the general procedure A (see Example 2 supra) using allenoate 2 (17.4 mg, 0.1 mmol, 1.0 equiv), tert-butyl piperazine-1-carboxylate (20.5 mg, 0.11 mmol, 1.1 equiv) and 1-phenylpiperazine (24.3 mg, 0.15 mmol, 1.5 equiv). The reaction time of the electrophilic amination step was 8 h. The product was isolated by silica gel chromatography as a colorless oil (30.7 mg, 59% yield).

¹H NMR (500 MHz, CDCl₃) δ 7.42-7.28 (m, 5H), 7.28-7.22 (m, 2H), 6.94-6.88 (m, 2H), 6.85 (tt, J=7.3, 1.1 Hz, 1H), 5.21-5.01 (m, 2H), 3.42-3.26 (m, 5H), 3.21-3.02 (m, 4H), 2.74-2.65 (m, 2H), 2.63-2.57 (m, 2H), 2.56-2.44 (m, 7H), 2.41-2.29 (m, 1H), 1.45 (s, 9H); ¹³C NMR (126 MHz, CDCl₃) δ 172.6, 154.9, 151.4, 136.1, 129.2, 128.7, 128.4, 128.3, 119.7, 116.1, 79.7, 66.4, 59.4, 58.8, 53.7, 49.3, 35.9, 28.6; HRMS (ESI/[M+H]⁺) calcd. for $C_{30}H_{43}N_4O_4^+$: 523.3279, found [M+H]⁺: 523.3271; FTIR (neat) $v_{max}$ 2917, 1733, 1693, 1599, 1423, 1246, 1166, 1136, 1080, 757 cm-1.

Benzyl 4-(4-phenylpiperazin-1-yl)-3-(2-oxa-6-azaspiro[3.3]heptan-6-yl)butanoate (compound 10)

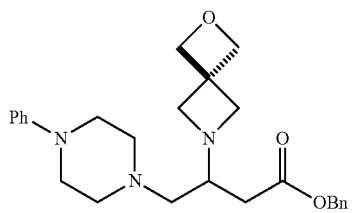

Compound 10 was prepared following the general procedure A (see Example 2 supra) using allenoate 2 (17.4 mg, 0.1 mmol, 1.0 equiv), 2-oxa-6-azaspiro[3.3]heptane (11.0 mg, 0.11 mmol, 1.1 equiv) and 1-phenylpiperazine (24.3 mg, 0.15 mmol, 1.5 equiv). The reaction time of the electrophilic amination step was 8 hours. The product was isolated by silica gel chromatography as a colorless oil (29.2 mg, 67% yield).

¹H NMR (500 MHz, CDCl₃) 7.38-7.28 (m, 5H), 7.29-7.22 (m, 2H), 6.93-6.87 (m, 2H), 6.85 (t, J=7.3 Hz, 1H), 5.18-5.05 (m, 2H), 4.70 (s, 4H), 3.44-3.26 (m, 5H), 3.16-3.03 (m, 4H), 2.87-2.77 (m, 2H), 2.66-2.49 (m, 4H), 2.45-2.30 (m, 3H), 2.26-2.13 (m, 1H); ¹³C NMR (126 MHz, CDCl₃) δ 172.2, 151.4, 136.0, 129.2, 128.7, 128.5, 128.4, 119.7, 116.1, 81.3, 66.5, 62.6, 61.4, 60.6, 54.0, 49.3, 38.9, 36.7; HRMS (ESI/[M+H]⁺) calcd. for $C_{26}H_{34}N_3O_3^+$: 436.2595, found [M+H]⁺: 436.2591; FTIR (neat) $v_{max}$ 2943, 2820, 1731, 1599, 1497, 1454, 1384, 1292, 1233, 1150, 1009, 971, 757, 695 cm⁻¹.

Benzyl 4-(4-phenylpiperazin-1-yl)-3-(4-phenylpiperidin-1-yl)butanoate (compound 11)

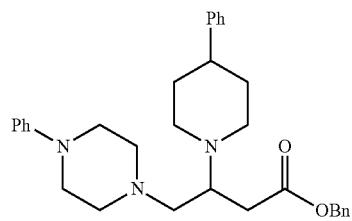 [SMILES: O=C(CC(CN1CCN(c2ccccc2)CC1)N1CCC(c2ccccc2)CC1)OCc1ccccc1]

Compound 11 was prepared following the general procedure A (see Example 2 supra) using allenoate 2 (17.4 mg, 0.1 mmol, 1.0 equiv), 4-phenylpiperidine (17.7 mg, 0.11 mmol, 1.1 equiv) and 1-phenylpiperazine (24.3 mg, 0.15 mmol, 1.5 equiv). The reaction time of the electrophilic amination step was 6 hours. The product was isolated by silica gel chromatography as a colorless oil (30.8 mg, 62% yield).

¹H NMR (500 MHz, CDCl₃) δ 7.41-7.34 (m, 4H), 7.33-7.25 (m, 5H), 7.24-7.18 (m, 3H), 6.93 (d, J=8.1 Hz, 2H), 6.87 (t, J=7.3 Hz, 1H), 5.20-5.09 (m, 2H), 3.49-3.38 (m, 1H), 3.22-3.08 (m, 4H), 2.93 (dd, J=31.2, 10.9 Hz, 2H), 2.81-2.71 (m, 2H), 2.67-2.58 (m, 2H), 2.58-2.50 (m, 4H), 2.49-2.39 (m, 3H), 1.87-1.78 (m, 2H), 1.75-1.62 (m, 2H); ¹³C NMR (126 MHz, CDCl₃) δ 173.0, 151.5, 146.5, 136.3, 129.2, 128.6, 128.5, 128.4, 128.3, 127.0, 126.2, 119.7, 116.1, 66.3, 60.0, 59.1, 53.8, 49.9, 49.8, 49.3, 43.1, 35.6, 34.2, 34.0; HRMS (ESI/[M+H]⁺) calcd. for $C_{32}H_{40}N_3O_2^+$: 498.3115, found [M+H]⁺: 498.3103; FTIR (neat) $v_{max}$ 2934, 2817, 1731, 1599, 1495, 1452, 1381, 1234, 1136, 1007, 756, 696 cm⁻¹.

Methyl 1-(4-(benzyloxy)-4-oxo-1-(4-phenylpiperazin-1-yl)butan-2-yl)piperidine-4-carboxylate (compound 12)

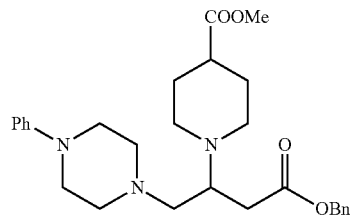 [SMILES: COC(=O)C1CCN(C(CC(=O)OCc2ccccc2)CN2CCN(c3ccccc3)CC2)CC1]

Compound 12 was prepared following the general procedure A (see Example 2 supra) using allenoate 2 (17.4 mg, 0.1 mmol, 1.0 equiv), methyl piperidine-4-carboxylate (15.7 mg, 0.11 mmol, 1.1 equiv) and 1-phenylpiperazine (24.3 mg, 0.15 mmol, 1.5 equiv). The reaction time of the electrophilic amination step was 6 hours. The product was isolated by silica gel chromatography as a colorless oil (38.8 mg, 81% yield).

¹H NMR (500 MHz, CDCl₃) δ 7.42-7.29 (m, 5H), 7.28 (t, J=7.9 Hz, 2H), 6.92 (d, J=8.2 Hz, 2H), 6.87 (t, J=7.3 Hz, 1H), 5.18-5.09 (m, 2H), 3.69 (s, 3H), 3.42-3.31 (m, 1H), 3.19-3.05 (m, 4H), 2.90-2.68 (m, 4H), 2.59-2.42 (m, 6H), 2.40-2.22 (m, 3H), 1.92-1.81 (m, 2H), 1.74-1.60 (m, 2H); $^{13}$C NMR (126 MHz, CDCl$_3$) δ 175.7, 172.8, 151.4, 136.2, 129.2, 128.6, 128.4, 128.2, 119.7, 116.0, 66.3, 59.5, 59.0, 53.7, 51.7, 49.3, 48.9, 48.2, 41.5, 35.7, 28.9, 28.8; HRMS (ESI/[M+H]$^+$) calcd. for C$_{28}$H$_{38}$N$_3$O$_4^+$: 480.2857, found [M+H]$^+$: 480.2857; FTIR (neat) ν$_{max}$ 2947, 2817, 1731, 1599, 1497, 1448, 1380, 1337, 1294, 1233, 1194, 1135, 1045, 1009, 971, 757, 695 cm$^{-1}$.

Benzyl 3-(diethylamino)-4-(4-phenylpiperazin-1-yl)butanoate (compound 13)

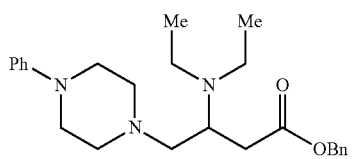 [SMILES: CCN(CC)C(CC(=O)OCc1ccccc1)CN1CCN(c2ccccc2)CC1]

Compound 13 was prepared following the general procedure A (see Example 2 supra) using allenoate 2 (17.4 mg, 0.1 mmol, 1.0 equiv), diethylamine (9.0 μL, 0.11 mmol, 1.1 equiv) and 1-phenylpiperazine (24.3 mg, 0.15 mmol, 1.5 equiv). The reaction time of the electrophilic amination step was 4 hours. The product was isolated by silica gel chromatography as a colorless oil (32.4 mg, 79% yield).

$^1$H NMR (500 MHz, CDCl$_3$) δ 7.41-7.22 (m, 7H), 6.94-6.89 (m, 1H), 6.85 (tt, J=7.2, 0.9 Hz, 1H), 5.17-5.04 (m, 2H), 3.57-3.46 (m, 1H), 3.17-3.06 (m, 4H), 2.77-2.69 (m, 2H), 2.58-2.34 (m, 10H), 1.04 (t, J=7.1 Hz, 6H); $^{13}$C NMR (126 MHz, CDCl$_3$) δ 173.1, 151.5, 136.3, 129.2, 128.6, 128.3, 128.2, 119.6, 116.0, 66.2, 60.4, 54.6, 53.9, 49.3, 44.1, 36.2, 14.7; HRMS (ESI/[M+H]$^+$) calcd. for C$_{25}$H$_{36}$N$_3$O$_2^+$: 410.2802, found [M+H]$^+$: 410.2802; FTIR (neat) ν$_{max}$ 2969, 2817, 1732, 1599, 1500, 1453, 1381, 1294, 1232, 1136, 1009, 756, 693 cm$^{-1}$.

Benzyl 3-(methyl(phenethyl)amino)-4-(4-phenylpiperazin-1-yl)butanoate (compound 14)

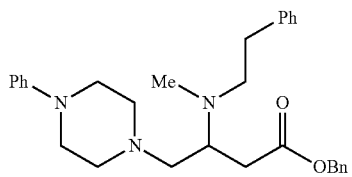 [SMILES: CN(CCc1ccccc1)C(CC(=O)OCc1ccccc1)CN1CCN(c2ccccc2)CC1]

Compound 14 was prepared following the general procedure A (see Example 2 supra) using allenoate 2 (17.4 mg, 0.1 mmol, 1.0 equiv), N-methyl-2-phenylethan-1-amine (16.0 μL, 0.11 mmol, 1.1 equiv) and 1-phenylpiperazine (24.3 mg, 0.15 mmol, 1.5 equiv). The reaction time of the electrophilic amination step was 8 hours. The product was isolated by silica gel chromatography as a colorless oil (35.4 mg, 75% yield).

$^1$H NMR (500 MHz, CDCl$_3$) δ 7.37-7.32 (m, 4H), 7.32-7.24 (m, 5H), 7.23-7.18 (m, 3H), 6.94-6.89 (m, 2H), 6.88-6.83 (m, 1H), 5.16-5.04 (m, 2H), 3.50-3.42 (m, 1H), 3.16-3.06 (m, 4H), 2.80-2.65 (m, 6H), 2.57-2.45 (m, 5H), 2.35 (s, 3H); $^{13}$C NMR (126 MHz, CDCl$_3$) δ 172.9, 151.4, 140.6, 136.2, 129.2, 128.9, 128.6, 128.4, 128.34, 128.26, 126.1, 119.7, 116.1, 66.3, 59.8, 57.9, 56.2, 53.8, 49.3, 37.4, 35.41, 35.35; HRMS (ESI/[M+H]$^+$) calcd. for C$_{30}$H$_{38}$N$_3$O$_2^+$: 472.2959, found [M+H]$^+$: 472.2968; FTIR (neat) ν$_{max}$ 2943, 2820, 1731, 1599, 1496, 1454, 1384, 1337, 1294, 1231, 1136, 1009, 925, 753, 696 cm$^{-1}$.

Benzyl 3-(allyl(methyl)amino)-4-(4-phenylpiperazin-1-yl)butanoate (compound 15)

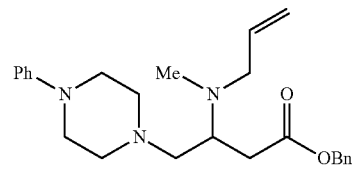 [SMILES: C=CCN(C)C(CC(=O)OCc1ccccc1)CN1CCN(c2ccccc2)CC1]

Compound 15 was prepared following the general procedure A (see Example 2 supra) using allenoate 2 (17.4 mg, 0.1 mmol, 1.0 equiv), N-allylmethylamine (11.0 μL, 0.11 mmol, 1.1 equiv) and 1-phenylpiperazine (24.3 mg, 0.15 mmol, 1.5 equiv). The reaction time of the electrophilic amination step was 6 hours. The product was isolated by silica gel chromatography as a colorless oil (24.5 mg, 60% yield).

$^1$H NMR (500 MHz, CDCl$_3$) δ 7.40-7.28 (m, 5H), 7.29-7.23 (m, 2H), 6.91 (d, J=7.9 Hz, 2H), 6.85 (t, J=7.3 Hz, 1H), 5.79 (ddt, J=16.6, 10.1, 6.3 Hz, 1H), 5.22-5.00 (m, 4H), 3.50-3.41 (m, 1H), 3.22-3.03 (m, 6H), 2.69 (dq, J=10.3, 5.1, 4.5 Hz, 2H), 2.58-2.45 (m, 5H), 2.35 (dd, J=12.4, 9.2 Hz, 1H), 2.24 (s, 3H); $^{13}$C NMR (126 MHz, CDCl$_3$) δ 172.8, 151.5, 136.8, 136.2, 129.2, 128.6, 128.33, 128.25, 119.7, 117.0, 116.1, 66.3, 59.7, 57.6, 56.7, 53.8, 49.3, 36.9, 35.4; HRMS (ESI/[M+H]$^+$) calcd. for C$_{25}$H$_{34}$N$_3$O$_2^+$: 408.2646, found [M+H]$^+$: 408.2648; FTIR (neat) ν$_{max}$ 3361, 2941, 2817, 1731, 1599, 1497, 1454, 1382, 1337, 1295, 1232, 1135, 1030, 1009, 923, 755, 693 cm$^{-1}$.

Benzyl 3-(methyl(prop-2-yn-1-yl)amino)-4-(4-phenylpiperazin-1-yl)butanoate (compound 16)

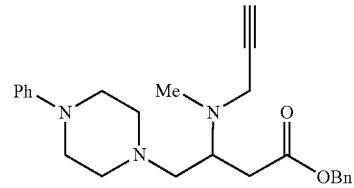 [SMILES: C#CCN(C)C(CC(=O)OCc1ccccc1)CN1CCN(c2ccccc2)CC1]

Compound 16 was prepared following the general procedure A (see Example 2 supra) using allenoate 2 (17.4 mg, 0.1 mmol, 1.0 equiv), N-methylprop-2-yn-1-amine (7.6 mg, 0.11 mmol, 1.1 equiv) and 1-phenylpiperazine (24.3 mg, 0.15 mmol, 1.5 equiv). The reaction time of the electrophilic amination step was 6 hours. The product was isolated by silica gel chromatography as a colorless oil (27.6 mg, 68% yield).

$^1$H NMR (500 MHz, CDCl$_3$) δ 7.38-7.31 (m, 4H), 7.26 (t, J=8.0 Hz, 3H), 6.95-6.87 (m, 2H), 6.89-6.81 (m, 1H), 5.17-5.07 (m, 2H), 3.57-3.48 (m, 1H), 3.49-3.37 (m, 2H), 3.22-3.04 (m, 5H), 2.76-2.47 (m, 8H), 2.37 (s, 3H); $^{13}$C NMR (126 MHz, CDCl$_3$) δ 172.5, 151.4, 136.2, 129.2, 128.6, 128.4, 128.3, 119.7, 116.1, 80.8, 72.8, 66.4, 60.1, 56.9, 53.8, 49.3, 43.8, 36.9, 35.8; HRMS (ESI/[M+H]$^+$)

Benzyl 4-(4-(4-bromophenyl)piperazin-1-yl)-3-(piperidin-1-yl)butanoate (compound 17)

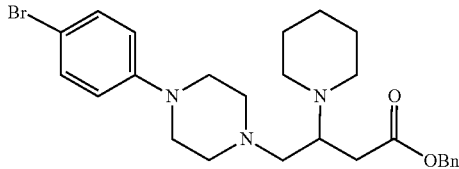 [SMILES: O=C(CC(CN1CCN(c2ccc(Br)cc2)CC1)N1CCCCC1)OCc1ccccc1]

Compound 17 was prepared following the general procedure A (see Example 2 supra) using allenoate 2 (17.4 mg, 0.1 mmol, 1.0 equiv), piperidine (11.0 µL, 0.11 mmol, 1.1 equiv) and 1-(4-bromophenyl)piperazine (36.2 mg, 0.15 mmol, 1.5 equiv). The reaction time of the electrophilic amination step was 4 hours. The product was isolated by silica gel chromatography as a colorless oil (30.5 mg, 61% yield).

$^1$H NMR (500 MHz, CDCl$_3$) δ 7.39-7.27 (m, 7H), 6.79-6.71 (m, 2H), 5.25-4.96 (m, 2H), 3.38-3.20 (m, 1H), 3.14-2.96 (m, 4H), 2.71 (dq, J=10.5, 5.9, 4.5 Hz, 2H), 2.62-2.31 (m, 10H), 1.50 (q, J=5.5 Hz, 4H), 1.40 (q, J=5.7 Hz, 2H); $^{13}$C NMR (126 MHz, CDCl$_3$) δ 173.2, 150.5, 136.3, 132.0, 128.7, 128.35, 128.28, 117.6, 111.7, 66.3, 60.0, 59.5, 53.6, 50.2, 49.2, 35.4, 26.7, 24.9; HRMS (ESI/[M+H]$^+$) calcd. for C$_{26}$H$_{35}$BrN$_3$O$_2$$^+$: 500.1907, found [M+H]$^+$: 500.1905; FTIR (neat) ν$_{max}$ 2932, 1733, 1493, 1453, 1235, 1151, 1136, 891, 808 cm$^{-1}$.

Benzyl 3-(piperidin-1-yl)-4-(4-(p-tolyl)piperazin-1-yl)butanoate (compound 18)

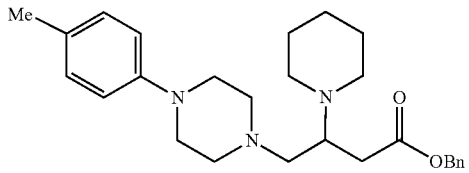 [SMILES: Cc1ccc(N2CCN(CC(CC(=O)OCc3ccccc3)N3CCCCC3)CC2)cc1]

Compound 18 was prepared following the general procedure A (see Example 2 supra) using allenoate 2 (17.4 mg, 0.1 mmol, 1.0 equiv), piperidine (11.0 µL, 0.11 mmol, 1.1 equiv) and 1-(p-tolyl)piperazine (26.4 mg, 0.15 mmol, 1.5 equiv). The reaction time of the electrophilic amination step was 4 hours. The product was isolated by silica gel chromatography as a colorless oil (25.3 mg, 58% yield).

$^1$H NMR (500 MHz, CDCl$_3$) δ 7.45-7.26 (m, 5H), 7.07 (d, J=8.4 Hz, 2H), 6.85-6.81 (m, 2H), 5.18-5.05 (m, 2H), 3.37-3.26 (m, 1H), 3.01-3.11 (m, 4H), 2.76-2.68 (m, 2H), 2.68-2.32 (m, 10H), 2.27 (s, 3H), 1.51 (q, J=5.6 Hz, 4H), 1.41 (q, J=5.5 Hz, 2H); $^{13}$C NMR (126 MHz, CDCl$_3$) δ 173.1, 149.4, 136.3, 129.7, 129.1, 128.6, 128.3, 128.2, 116.4, 66.2, 60.0, 59.4, 53.8, 50.2, 49.9, 35.4, 26.7, 24.9, 20.5; HRMS (ESI/[M+H]$^+$) calcd. for C$_{27}$H$_{38}$N$_3$O$_2$$^+$: 436.2959, found [M+H]$^+$: 436.2964; FTIR (neat) ν$_{max}$ 2932, 2817, 1733, 1515, 1453, 1238, 1151, 1008, 808 cm$^{-1}$.

Benzyl 4-(4-(4-methoxyphenyl)piperazin-1-yl)-3-(piperidin-1-yl)butanoate (compound 19)

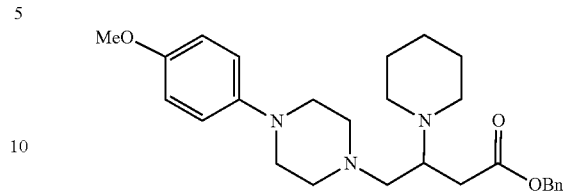

Compound 19 was prepared following the general procedure A (see Example 2 supra) using allenoate 2 (17.4 mg, 0.1 mmol, 1.0 equiv), piperidine (11.0 µL, 0.11 mmol, 1.1 equiv) and 1-(4-methoxyphenyl)piperazine (28.8 mg, 0.15 mmol, 1.5 equiv). The reaction time of the electrophilic amination step was 4 hours. The product was isolated by silica gel chromatography as a colorless oil (27.2 mg, 60% yield).

$^1$H NMR (500 MHz, CDCl$_3$) δ 7.40-7.27 (m, 5H), 6.91-6.80 (m, 4H), 5.24-5.03 (m, 2H), 3.76 (s, 3H), 3.38-3.24 (m, 1H), 3.05-2.95 (m, 4H), 2.78-2.69 (m, 2H), 2.61-2.36 (m, 10H), 1.50 (q, J=5.6 Hz, 4H), 1.40 (q, J=5.7 Hz, 2H); $^{13}$C NMR (126 MHz, CDCl$_3$) δ 173.1, 153.8, 145.9, 136.3, 128.6, 128.3, 128.2, 118.1, 114.5, 66.2, 59.9, 59.4, 55.7, 53.9, 50.8, 50.2, 35.4, 26.6, 24.9; HRMS (ESI/[M+H]$^+$) calcd. for C$_{27}$H$_{38}$N$_3$O$_3$$^+$: 452.2908, found [M+H]$^+$: 452.2911; FTIR (neat) ν$_{max}$ 2932, 2815, 1731, 1510, 1497, 1454, 1379, 1293, 1241, 1151, 1135, 1036, 1012, 822, 742, 698 cm$^{-1}$.

Benzyl 3-(piperidin-1-yl)-4-(4-(4-(trifluoromethyl)phenyl)piperazin-1-yl)butanoate (compound 20)

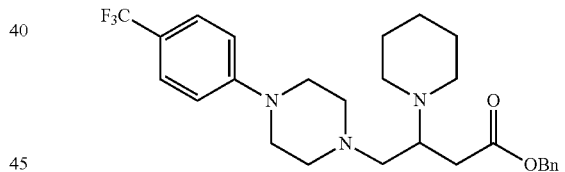

Compound 20 was prepared following the general procedure A (see Example 2 supra) using allenoate 2 (17.4 mg, 0.1 mmol, 1.0 equiv), piperidine (11.0 µL, 0.11 mmol, 1.1 equiv) and 1-(4-(trifluoromethyl)phenyl)piperazine (34.5 mg, 0.15 mmol, 1.5 equiv). The reaction time of the electrophilic amination step was 4 hours. The product was isolated by silica gel chromatography as a colorless oil (30.8 mg, 63% yield).

$^1$H NMR (500 MHz, CDCl$_3$) δ 7.47 (d, J=8.7 Hz, 2H), 7.39-7.26 (m, 5H), 6.88 (d, J=8.8 Hz, 2H), 5.32-4.90 (m, 2H), 3.36-3.24 (m, 1H), 3.23-3.07 (m, 4H), 2.75-2.68 (m, 2H), 2.65-2.34 (m, 10H), 1.58-1.47 (m, 4H), 1.41 (q, J=5.9 Hz, 2H); $^{13}$C NMR (126 MHz, CDCl$_3$) δ 173.1, 153.5, 136.3, 128.6, 128.3, 126.5 (q, J=3.8 Hz), 124.9 (q, J=270.9 Hz), 120.4 (q, J=32.7 Hz), 114.5, 66.3, 59.9, 59.4, 53.5, 50.2, 48.1, 35.3, 26.6, 24.9; $^{19}$F NMR (471 MHz, CDCl$_3$) δ −62.44; HRMS (ESI/[M+H]$^+$) calcd. for C$_{27}$H$_{35}$F$_3$N$_3$O$_2$$^+$: 490.2676, found [M+H]$^+$: 490.2674; FTIR (neat) ν$_{max}$ 2933, 2818, 1732, 1614, 1524, 1454, 1386, 1329, 1236, 1160, 1111, 1071, 1001, 823, 742, 697 cm$^{-1}$.

Benzyl 4-(4-(2-cyanophenyl)piperazin-1-yl)-3-(piperidin-1-yl)butanoate (compound 21)

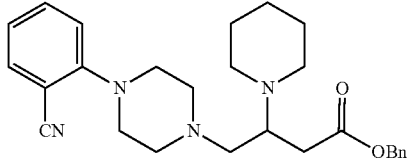 [SMILES: N#Cc1ccccc1N1CCN(CC(CC(=O)OCc2ccccc2)N2CCCCC2)CC1]

Compound 21 was prepared following the general procedure A (see Example 2 supra) using allenoate 2 (17.4 mg, 0.1 mmol, 1.0 equiv), piperidine (11.0 µL, 0.11 mmol, 1.1 equiv) and 4-(piperazin-1-yl)benzonitrile (28.1 mg, 0.15 mmol, 1.5 equiv). The reaction time of the electrophilic amination step was 4 hours. The product was isolated by silica gel chromatography as a colorless oil (25.7 mg, 57% yield).

$^1$H NMR (500 MHz, CDCl$_3$) δ 7.54 (dd, J=7.7, 1.7 Hz, 1H), 7.49-7.42 (m, 1H), 7.40-7.26 (m, 5H), 7.02-6.92 (m, 2H), 5.17-5.08 (m, 2H), 3.34-3.23 (m, 1H), 3.13 (t, J=4.8 Hz, 4H), 2.82-2.71 (m, 2H), 2.61-2.34 (m, 10H), 1.58-1.44 (m, 4H), 1.44-1.34 (m, 2H); $^{13}$C NMR (126 MHz, CDCl$_3$) δ 173.1, 155.8, 136.3, 134.5, 133.8, 128.6, 128.3, 128.2, 121.6, 118.7, 118.6, 105.9, 66.2, 59.5, 59.5, 53.7, 51.7, 50.2, 35.5, 26.6, 24.9; HRMS (ESI/[M+H]$^+$) calcd. for C$_{27}$H$_{35}$N$_4$O$_2$$^+$: 447.2755, found [M+H]$^+$: 447.2750; FTIR (neat) ν$_{max}$ 2932, 2818, 1731, 1595, 1488, 1446, 1378, 1347, 1293, 1230, 1150, 1134, 1009, 757, 698 cm$^{-1}$.

Benzyl 4-(4-(3,4-dichlorophenyl)piperazin-1-yl)-3-(piperidin-1-yl)butanoate (compound 22)

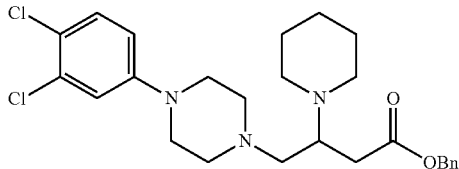 [SMILES: O=C(CC(CN1CCN(c2ccc(Cl)c(Cl)c2)CC1)N1CCCCC1)OCc1ccccc1]

Compound 22 was prepared following the general procedure A (see Example 2 supra) using allenoate 2 (17.4 mg, 0.1 mmol, 1.0 equiv), piperidine (11.0 µL, 0.11 mmol, 1.1 equiv) and 1-(3,4-dichlorophenyl)piperazine (34.7 mg, 0.15 mmol, 1.5 equiv). The reaction time of the electrophilic amination step was 4 h. The product was isolated by silica gel chromatography as a colorless oil (31.7 mg, 64% yield).

$^1$H NMR (500 MHz, CDCl$_3$) δ 7.39-7.25 (m, 5H), 7.25 (d, J=8.9 Hz, 1H), 6.90 (d, J=2.9 Hz, 1H), 6.69 (dd, J=8.9, 2.9 Hz, 1H), 5.15-5.06 (m, 2H), 3.34-3.24 (m, 1H), 3.11-2.98 (m, 4H), 2.73-2.64 (m, 2H), 2.62-2.34 (m, 10H), 1.58-1.46 (m, 4H), 1.44-1.36 (m, 2H); $^{13}$C NMR (126 MHz, CDCl$_3$) δ 173.1, 150.8, 136.3, 132.8, 130.5, 128.6, 128.32, 128.26, 122.0, 117.2, 115.3, 66.3, 59.9, 59.4, 53.4, 50.2, 48.8, 35.3, 26.6, 24.9; HRMS (ESI/[M+H]$^+$) calcd. for C$_{26}$H$_{34}$Cl$_2$N$_3$O$_2$$^+$: 490.2023, found [M+H]$^+$: 490.2027; FTIR (neat) ν$_{max}$ 2932, 2818, 1732, 1593, 1484, 1453, 1382, 1237, 1151, 1137, 1009, 951, 699 cm$^{-1}$.

Benzyl 3-(piperidin-1-yl)-4-thiomorpholinobutanoate (compound 23)

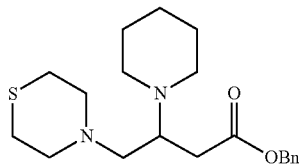 [SMILES: O=C(CC(CN1CCSCC1)N1CCCCC1)OCc1ccccc1]

Compound 23 was prepared following the general procedure A (see Example 2 supra) using allenoate 2 (17.4 mg, 0.1 mmol, 1.0 equiv), piperidine (11.0 µL, 0.11 mmol, 1.1 equiv) and thiomorpholine (15.5 mg, 0.15 mmol, 1.5 equiv). The reaction time of the electrophilic amination step was 4 hours. The product was isolated by silica gel chromatography as a colorless oil (21.0 mg, 58% yield).

$^1$H NMR (500 MHz, CDCl$_3$) δ 7.44-7.27 (m, 5H), 5.17-5.07 (m, 2H), 3.34-3.20 (m, 1H), 2.87-2.73 (m, 1H), 2.70-2.33 (m, 11H), 2.33-2.15 (m, 2H), 1.50 (bs, 5H), 1.44-1.32 (m, 3H); $^{13}$C NMR (126 MHz, CDCl$_3$) δ 173.1, 136.3, 128.7, 128.3, 128.2, 66.3, 60.7, 59.5, 55.8, 50.2, 35.3, 28.1, 26.6, 24.9; HRMS (ESI/[M+H]$^+$) calcd. for C$_{20}$H$_{31}$N$_2$O$_2$S$^+$: 363.2101, found [M+H]$^+$: 363.2100; FTIR (neat) ν$_{max}$ 2933, 2851, 2808, 1731, 1455, 1378, 1218, 1154, 1008, 1001, 957 cm$^{-1}$.

Benzyl 3-(piperidin-1-yl)-4-(4-(pyrimidin-2-yl)piperazin-1-yl)butanoate (compound 24)

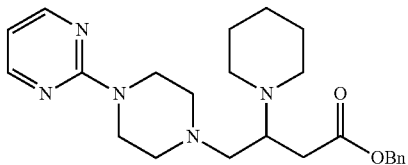 [SMILES: O=C(CC(CN1CCN(c2ncccn2)CC1)N1CCCCC1)OCc1ccccc1]

Compound 24 was prepared following the general procedure A (see Example 2 supra) using allenoate 2 (17.4 mg, 0.1 mmol, 1.0 equiv), piperidine (11.0 µL, 0.11 mmol, 1.1 equiv) and 2-(piperazin-1-yl)pyrimidine (24.6 mg, 0.15 mmol, 1.5 equiv). The reaction time of the electrophilic amination step was 4 hours. The product was isolated by silica gel chromatography as a colorless oil (28.8 mg, 68% yield).

$^1$H NMR (500 MHz, CDCl$_3$) δ 8.28 (d, J=4.7 Hz, 2H), 7.39-7.25 (m, 5H), 6.45 (t, J=4.7 Hz, 1H), 5.19-5.06 (m, 2H), 3.77-3.65 (m, 4H), 3.35-3.26 (m, 1H), 2.65-2.43 (m, 9H), 2.42-2.34 (m, 3H), 1.49 (q, J=5.5 Hz, 4H), 1.39 (q, J=5.9 Hz, 2H); $^{13}$C NMR (126 MHz, CDCl$_3$) δ 173.1, 161.8, 157.8, 136.3, 128.6, 128.3, 128.2, 109.8, 66.3, 60.0, 59.5, 53.7, 50.2, 43.9, 35.4, 26.6, 24.9; HRMS (ESI/[M+H]$^+$) calcd. for C$_{24}$H$_{34}$N$_5$O$_2$$^+$: 424.2707, found [M+H]$^+$: 424.2706; FTIR (neat) ν$_{max}$ 2932, 1733, 1585, 1546, 1500, 1447, 1359, 1259, 983 cm$^{-1}$.

Benzyl 4-(4-phenylpiperidin-1-yl)-3-(piperidin-1-yl)butanoate (compound 25)

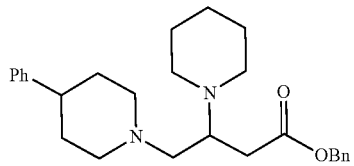 [SMILES: O=C(CC(CN1CCC(c2ccccc2)CC1)N1CCCCC1)OCc1ccccc1]

Compound 25 was prepared following the general procedure A (see Example 2 supra) using allenoate 2 (17.4 mg, 0.1 mmol, 1.0 equiv), piperidine (11.0 µL, 0.11 mmol, 1.1 equiv) and 4-phenylpiperidine (24.2 mg, 0.15 mmol, 1.5 equiv). The reaction time of the electrophilic amination step was 4 h. The product was isolated by silica gel chromatography as a colorless oil (33.6 mg, 80% yield).

$^1$H NMR (500 MHz, CDCl$_3$) δ 7.40-7.27 (m, 7H), 7.22-7.17 (m, 3H), 5.19-5.10 (m, 2H), 3.33 (s, 1H), 3.11 (d, J=11.2 Hz, 1H), 2.91 (d, J=11.3 Hz, 1H), 2.64-2.22 (m, 10H), 2.01 (s, 1H), 1.84-1.64 (m, 4H), 1.58-1.48 (m, 4H), 1.41 (q, J=6.0 Hz, 2H); $^{13}$C NMR (126 MHz, CDCl$_3$) δ 173.1, 146.6, 136.4, 128.6, 128.5, 128.3, 128.2, 126.9, 126.2, 66.3, 59.7, 56.1, 53.8, 50.2, 42.6, 33.8, 33.5, 26.5, 24.9; HRMS (ESI/[M+H]$^+$) calcd. for C$_{27}$H$_{37}$N$_2$O$_2^+$: 421.2850, found [M+H]$^+$: 421.2840; FTIR (neat) ν$_{max}$ 2932, 2849, 2796, 1732, 1494, 1452, 1378, 1346, 1260, 1216, 1153, 1135, 1008, 993, 751, 698 cm$^{-1}$.

Benzyl 4-((3,4-dimethoxyphenethyl)(methyl)amino)-3-(piperidin-1-yl)butanoate (compound 26)

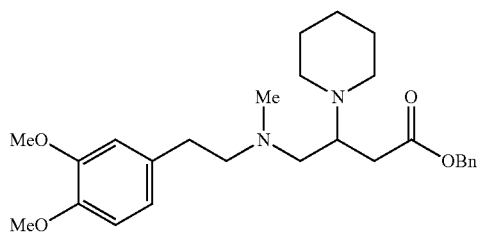 [SMILES: COc1ccc(CCN(C)CC(CC(=O)OCc2ccccc2)N2CCCCC2)cc1OC]

Compound 26 was prepared following the general procedure A (see Example 2 supra) using allenoate 2 (17.4 mg, 0.1 mmol, 1.0 equiv), piperidine (11.0 µL, 0.11 mmol, 1.1 equiv) and 2-(3,4-dimethoxyphenyl)-N-methylethan-1-amine (29.3 mg, 0.15 mmol, 1.5 equiv). The reaction time of the electrophilic amination step was 4 hours. The product was isolated by silica gel chromatography as a colorless oil (23.7 mg, 52% yield).

$^1$H NMR (500 MHz, CDCl$_3$) δ 7.40-7.27 (m, 5H), 6.77 (d, J=8.5 Hz, 1H), 6.74-6.67 (m, 2H), 5.22-5.02 (m, 2H), 3.85 (s, 3H), 3.84 (s, 3H), 3.27-3.18 (m, 1H), 2.70-2.58 (m, 3H), 2.57-2.48 (m, 5H), 2.48-2.42 (m, 3H), 2.40-2.33 (m, 1H), 2.27 (s, 3H), 1.53-1.45 (m, 4H), 1.41-1.34 (m, 2H); $^{13}$C NMR (126 MHz, CDCl$_3$) δ 173.2, 148.9, 147.3, 136.4, 133.3, 128.6, 128.3, 128.1, 120.6, 112.1, 111.3, 66.1, 60.5, 60.4, 58.5, 56.0, 55.9, 50.1, 42.8, 35.0, 33.5, 26.6, 24.9; HRMS (ESI/[M+H]$^+$) calcd. for C$_{27}$H$_{39}$N$_2$O$_4^+$: 455.2904, found [M+H]$^+$: 455.2901; FTIR (neat) ν$_{max}$ 2932, 2848, 1732, 155, 1454, 1262, 1236, 1153, 1031, 807, 700 cm$^{-1}$.

Benzyl 4-((N,4-dimethylphenyl)sulfonamido)-3-(piperidin-1-yl)butanoate (compound 27)

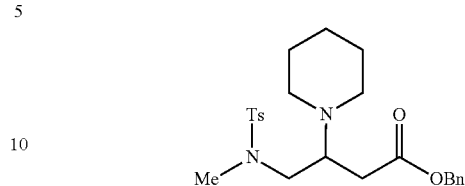

Compound 27 was prepared following the general procedure A (see Example 2 supra) using allenoate 2 (17.4 mg, 0.1 mmol, 1.0 equiv), piperidine (11.0 µL, 0.11 mmol, 1.1 equiv) and N,4-dimethylbenzenesulfonamide (27.8 mg, 0.15 mmol, 1.5 equiv). The reaction time of the electrophilic amination step was 4 hours. The reaction temperature of the nucleophilic amination step was 60° C. The product was isolated by silica gel chromatography as a colorless oil (31.2 mg, 70% yield).

$^1$H NMR (500 MHz, CDCl$_3$) δ 7.65 (d, J=8.3 Hz, 2H), 7.41-7.28 (m, 7H), 5.23-5.04 (m, 2H), 3.36-3.27 (m, 1H), 3.19 (dd, J=13.1, 8.4 Hz, 1H), 2.87 (dd, J=13.0, 6.0 Hz, 1H), 2.71 (s, 3H), 2.61 (dd, J=15.0, 6.7 Hz, 1H), 2.53-2.46 (m, 5H), 2.42 (s, 3H), 1.52-1.43 (m, 4H), 1.41-1.34 (m, 2H); $^{13}$C NMR (126 MHz, CDCl$_3$) δ 172.7, 143.4, 136.1, 134.6, 129.8, 128.6, 128.5, 128.3, 127.6, 66.6, 59.9, 50.9, 50.0, 35.6, 33.7, 26.5, 24.8, 21.6; HRMS (ESI/[M+H]$^+$) calcd. for C$_{24}$H$_{33}$N$_2$O$_4$S$^+$: 445.2156, found [M+H]$^+$: 445.2154; FTIR (neat) ν$_{max}$ 2932, 1732, 1454, 1341, 1161, 1110, 968, 741 cm$^{-1}$.

Benzyl 4-(bis(tert-butoxycarbonyl)amino)-3-(piperidin-1-yl)butanoate (compound 28)

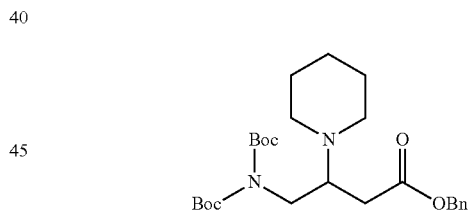

Compound 28 was prepared following the general procedure A (see Example 2 supra) using allenoate 2 (17.4 mg, 0.1 mmol, 1.0 equiv), piperidine (11.0 µL, 0.11 mmol, 1.1 equiv) and di-tert-butyl iminodicarbonate (32.6 mg, 0.15 mmol, 1.5 equiv). The reaction time of the electrophilic amination step was 4 hours. The reaction temperature of the nucleophilic amination step was 60° C. The product was isolated by silica gel chromatography as a colorless oil (28.2 mg, 59% yield).

$^1$H NMR (500 MHz, CDCl$_3$) δ 7.39-7.29 (m, 5H), 5.12 (s, 2H), 3.81 (dd, J=13.9, 7.1 Hz, 1H), 3.50 (dd, J=13.9, 7.4 Hz, 1H), 3.40-3.33 (m, 1H), 2.57 (dd, J=14.3, 7.9 Hz, 1H), 2.50 (s, 4H), 2.30 (dd, J=14.3, 6.6 Hz, 1H), 1.49 (s, 18H), 1.47-1.43 (m, 4H), 1.38-1.33 (m, 2H); $^{13}$C NMR (126 MHz, CDCl$_3$) δ 172.6, 152.9, 136.2, 128.6, 128.4, 128.2, 82.4, 66.4, 61.3, 49.9, 45.8, 34.2, 28.3, 26.6, 24.9; HRMS (ESI/[M+H]$^+$) calcd. for C$_{26}$H$_{41}$N$_2$O$_6^+$: 477.2959, found [M+H]$^+$: 477.2960; FTIR (neat) ν$_{max}$ 2932, 2820, 1737, 1367, 1162, 1122, 755 cm-1.

Benzyl 4-(1,3-dioxoisoindolin-2-yl)-3-(piperidin-1-yl)butanoate (compound 29)

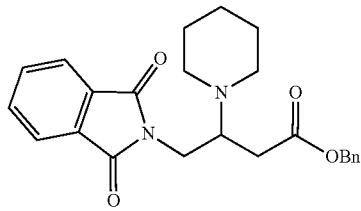 [SMILES: O=C(CC(CN1C(=O)c2ccccc2C1=O)N1CCCCC1)OCc1ccccc1]

Compound 29 was prepared following the general procedure A (see Example 2 supra) using allenoate 2 (17.4 mg, 0.1 mmol, 1.0 equiv), piperidine (11.0 µL, 0.11 mmol, 1.1 equiv) and phthalimide (22.1 mg, 0.15 mmol, 1.5 equiv). The reaction time of the electrophilic amination step was 4 hours. The reaction temperature of the nucleophilic amination step was 60° C. The product was isolated by silica gel chromatography as a colorless oil (23.6 mg, 58% yield).

$^1$H NMR (500 MHz, CDCl$_3$) δ 7.83 (dd, J=5.4, 3.0 Hz, 2H), 7.70 (dd, J=5.5, 3.0 Hz, 2H), 7.39-7.27 (m, 5H), 5.10-5.01 (m, 2H), 3.88 (dd, J=13.7, 8.1 Hz, 1H), 3.65-3.57 (m, 1H), 3.56-3.47 (m, 1H), 2.68 (dd, J=14.7, 6.8 Hz, 1H), 2.59 (dt, J=10.5, 4.8 Hz, 2H), 2.44 (dt, J=10.6, 5.1 Hz, 2H), 2.33 (dd, J=14.7, 7.2 Hz, 1H), 1.41-1.29 (m, 6H); $^{13}$C NMR (126 MHz, CDCl$_3$) δ 172.2, 168.4, 136.0, 134.0, 132.3, 128.6, 128.4, 128.3, 123.3, 66.5, 59.9, 49.8, 38.7, 34.0, 26.6, 24.8; HRMS (ESI/[M+H]$^+$) calcd. for C$_{24}$H$_{27}$N$_2$O$_4^+$: 407.1965, found [M+H]$^+$: 407.1960; FTIR (neat) $v_{max}$ 2933, 1712, 1398, 1171, 1099, 1000, 723, 698 cm$^{-1}$.

Ethyl 4-(4-phenylpiperazin-1-yl)-3-(piperidin-1-yl)butanoate (compound 30)

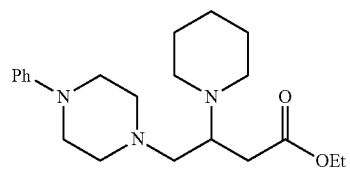 [SMILES: CCOC(=O)CC(CN1CCN(c2ccccc2)CC1)N1CCCCC1]

Compound 30 was prepared following the general procedure A (see Example 2 supra) using allenoate A1 (11.2 mg, 0.1 mmol, 1.0 equiv), piperidine (11.0 µL, 0.11 mmol, 1.1 equiv) and 1-phenylpiperazine (24.3 mg, 0.15 mmol, 1.5 equiv). The reaction time of the electrophilic amination step was 4 hours. The product was isolated by silica gel chromatography as a colorless oil (18.7 mg, 52% yield).

$^1$H NMR (500 MHz, CDCl$_3$) δ 7.28-7.23 (m, 2H), 6.94-6.89 (m, 2H), 6.88-6.81 (m, 1H), 4.16-4.05 (m, 2H), 3.28 (dt, J=13.9, 6.7 Hz, 1H), 3.17-3.08 (m, 4H), 2.77-2.71 (m, 2H), 2.60-2.47 (m, 8H), 2.43-2.35 (m, 2H), 1.53 (q, J=5.4 Hz, 4H), 1.42 (q, J=5.7 Hz, 2H), 1.25 (t, J=7.1 Hz, 3H); $^{13}$C NMR (126 MHz, CDCl$_3$) δ 173.3, 151.5, 129.2, 119.7, 116.1, 60.3, 60.1, 59.4, 53.8, 50.2, 49.4, 35.4, 26.7, 24.9, 14.4; HRMS (ESI/[M+H]$^+$) calcd. for C$_{21}$H$_{34}$N$_3$O$_2^+$: 360.2646, found [M+H]$^+$: 360.2631; FTIR (neat) $v_{max}$ 2932, 2817, 1730, 1599, 1501, 1452, 1385, 1296, 1231, 1152, 1136, 1009, 927, 757, 690 cm$^{-1}$.

3-Chlorobenzyl 4-(4-phenylpiperazin-1-yl)-3-(piperidin-1-yl)butanoate (compound 31)

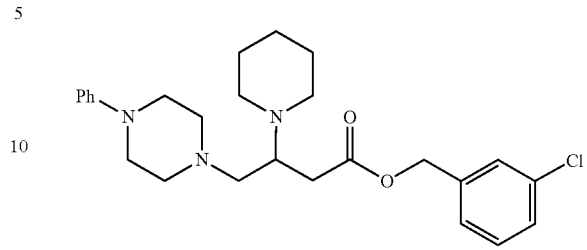

Compound 31 was prepared following the general procedure A (see Example 2 supra) using allenoate A2 (20.8 mg, 0.1 mmol, 1.0 equiv), piperidine (11.0 µL, 0.11 mmol, 1.1 equiv) and 1-phenylpiperazine (24.3 mg, 0.15 mmol, 1.5 equiv). The reaction time of the electrophilic amination step was 4 hours. The product was isolated by silica gel chromatography as a colorless oil (25.8 mg, 56% yield).

$^1$H NMR (500 MHz, CDCl$_3$) δ 7.33-7.23 (m, 6H), 6.90 (dd, J=8.8, 0.9 Hz, 2H), 6.87-6.83 (m, 1H), 5.11-5.02 (m, 2H), 3.34-3.25 (m, 1H), 3.17-3.03 (m, 4H), 2.77-2.68 (m, 2H), 2.61-2.51 (m, 4H), 2.51-2.43 (m, 5H), 2.42-2.35 (m, 1H), 1.56-1.46 (m, 4H), 1.45-1.36 (m, 2H); $^{13}$C NMR (126 MHz, CDCl$_3$) δ 173.0, 151.5, 134.9, 134.1, 129.7, 129.2, 128.8, 119.7, 116.0, 65.4, 59.8, 59.5, 53.8, 50.2, 49.3, 35.5, 26.6, 24.9; HRMS (ESI/[M+H]$^+$) calcd. for C$_{26}$H$_{35}$ClN$_3$O$_2^+$: 456.2412, found [M+H]$^+$: 456.2404; FTIR (neat) $v_{max}$ 2932, 2817, 1732, 1599, 1494, 1452, 1231, 1151, 1135, 1010, 807, 757 cm$^{-1}$.

3-Methoxybenzyl 4-(4-phenylpiperazin-1-yl)-3-(piperidin-1-yl)butanoate (compound 32)

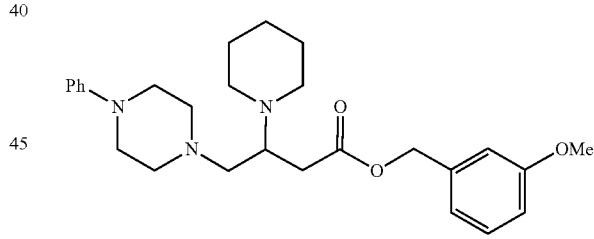

Compound 32 was prepared following the general procedure A (see Example 2 supra) using allenoate A3 (20.4 mg, 0.1 mmol, 1.0 equiv), piperidine (11.0 µL, 0.11 mmol, 1.1 equiv) and 1-phenylpiperazine (24.3 mg, 0.15 mmol, 1.5 equiv). The reaction time of the electrophilic amination step was 4 hours. The product was isolated by silica gel chromatography as a colorless oil (30.7 mg, 68% yield).

$^1$H NMR (500 MHz, CDCl$_3$) δ 7.32-7.22 (m, 3H), 6.99-6.89 (m, 4H), 6.86 (t, J=7.2 Hz, 2H), 5.14-5.05 (m, 2H), 3.80 (s, 3H), 3.34 (bs, 1H), 3.17-3.08 (m, 4H), 2.80-2.70 (m, 2H), 2.67-2.40 (m, 10H), 1.55 (bs, 4H), 1.43 (q, J=6.0 Hz, 2H); $^{13}$C NMR (126 MHz, CDCl$_3$) δ 173.1, 159.8, 151.5, 137.8, 129.7, 129.2, 120.5, 119.7, 116.1, 113.8, 113.7, 66.2, 59.4, 55.3, 53.8, 50.2, 49.3, 35.4, 29.8, 26.6, 24.9; HRMS (ESI/[M+H]$^+$) calcd. for C$_{27}$H$_{38}$N$_3$O$_3^+$: 452.2908, found [M+H]$^+$: 452.2902; FTIR (neat) $v_{max}$ 2931, 1731, 1599, 1494, 1453, 1267, 1231, 1152, 1136, 1008, 757, 689 cm$^{-1}$.

Benzyl 4-(4-(2-((2,4-dimethylphenyl)thio)phenyl)piperazin-1-yl)-3-(piperidin-1-yl)butanoate (compound 33)

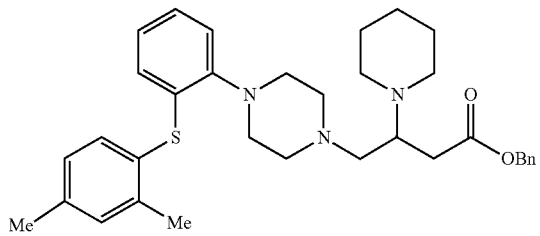 [SMILES: Cc1ccc(Sc2ccccc2N2CCN(CC(CC(=O)OCc3ccccc3)N3CCCCC3)CC2)c(C)c1]

Compound 33 was prepared following the general procedure A (see Example 2 supra) using allenoate 2 (17.4 mg, 0.1 mmol, 1.0 equiv), piperidine (11.0 μL, 0.11 mmol, 1.1 equiv) and Vortioxetine (44.7 mg, 0.15 mmol, 1.5 equiv). The reaction time of the electrophilic amination step was 4 hours. The product was isolated by silica gel chromatography as a colorless oil (30.7 mg, 55% yield).

$^1$H NMR (500 MHz, CDCl$_3$) δ 7.41-7.35 (m, 5H), 7.34-7.29 (m, 1H), 7.16-7.14 (m, 1H), 7.09-6.99 (m, 3H), 6.89-6.80 (m, 1H), 6.50 (dd, J=7.9, 1.4 Hz, 1H), 5.25-5.09 (m, 2H), 3.39-3.24 (m, 1H), 3.02 (bs, 4H), 2.77 (bs, 2H), 2.63-2.45 (m, 8H), 2.36 (s, 1H), 2.32 (s, 1H), 1.56-1.48 (m, 4H), 1.46-1.35 (m, 2H); $^{13}$C NMR (126 MHz, CDCl$_3$) δ 173.2, 149.5, 142.6, 139.3, 136.4, 136.3, 134.6, 131.8, 128.6, 128.4, 128.3, 128.2, 127.9, 126.3, 125.5, 124.3, 119.8, 66.2, 59.7, 59.6, 54.2, 51.9, 50.2, 35.6, 26.7, 24.9, 21.3, 20.7; HRMS (ESI/[M+H]$^+$) calcd. for C$_{34}$H$_{44}$N$_3$O$_2$S$^+$: 558.3149, found [M+H]$^+$: 558.3122; FTIR (neat) ν$_{max}$ 2933, 2815, 1733, 1579, 1470, 1440, 1376, 1224, 1150, 1010, 750 cm$^{-1}$.

Benzyl 4-(4-(2-chlorodibenzo[b,f][1,4]oxazepin-11-yl)piperazin-1-yl)-3-(piperidin-1-yl)butanoate (compound 34)

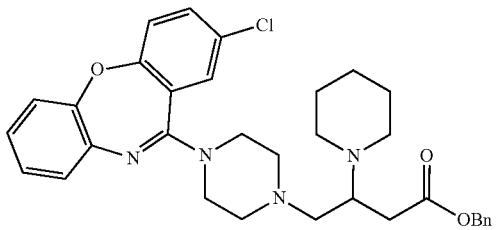 [SMILES: O=C(CC(CN1CCN(C2=Nc3ccccc3Oc3ccc(Cl)cc32)CC1)N1CCCCC1)OCc1ccccc1]

Compound 34 was prepared following the general procedure B (see Example 2 supra) using allenoate 2 (17.4 mg, 0.1 mmol, 1.0 equiv), N-chloropiperidine (13.1 mg, 0.11 mmol, 1.1 equiv) and Amoxapine (46.7 mg, 0.15 mmol, 1.5 equiv). The reaction time of the electrophilic amination step was 4 hours. The product was isolated by silica gel chromatography as a colorless oil (37.8 mg, 66% yield).

$^1$H NMR (500 MHz, CDCl$_3$) δ 7.40-7.29 (m, 6H), 7.28 (d, J=2.6 Hz, 1H), 7.18 (d, J=8.6 Hz, 1H), 7.13 (dd, J=7.8, 1.7 Hz, 1H), 7.11-7.05 (m, 2H), 7.01-6.95 (m, 1H), 5.24-5.03 (m, 2H), 3.59-3.12 (m, 5H), 2.80-2.28 (m, 12H), 1.58-1.45 (m, 4H), 1.42-1.31 (m, 2H); $^{13}$C NMR (126 MHz, CDCl$_3$) δ 173.1, 159.4, 159.0, 151.9, 140.4, 136.3, 132.54, 130.3, 129.3, 128.7, 128.4, 128.3, 127.2, 125.9, 125.2, 124.5, 122.8, 120.2, 66.3, 59.8, 59.4, 53.6, 50.2, 35.4, 26.6, 24.9; HRMS (ESI/[M+H]$^+$) calcd. for C$_{33}$H$_{38}$ClN$_4$O$_3^+$: 573.2626, found [M+H]$^+$: 573.2623; FTIR (neat) ν$_{max}$ 2932, 2850, 2805, 1730, 1600, 1587, 1556, 1453, 1304, 1241, 1215, 1154, 1109, 1004, 752 cm$^{-1}$.

Benzyl 4-(methyl((R)-3-phenyl-3-(o-tolyloxy)propyl)amino)-3-(piperidin-1-yl)butanoate (compound 35)

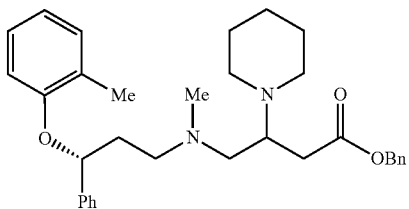 [SMILES: Cc1ccccc1O[C@H](CCN(C)CC(CC(=O)OCc1ccccc1)N1CCCCC1)c1ccccc1]

Compound 35 was prepared following the general procedure B (see Example 2 supra) using allenoate 2 (17.4 mg, 0.1 mmol, 1.0 equiv), N-chloropiperidine (13.1 mg, 0.11 mmol, 1.1 equiv) and Atomoxetine (38.3 mg, 0.15 mmol, 1.5 equiv). The reaction time of the electrophilic amination step was 4 hours. The product was isolated by silica gel chromatography as a colorless oil (41.7 mg, 81% yield, 1:1 dr, characterized as an inseparable mixture).

$^1$H NMR (500 MHz, CDCl$_3$) δ 7.42-7.30 (m, 8H), 7.30-7.23 (m, 2H), 7.12 (d, J=7.2 Hz, 1H), 7.00-6.92 (m, 1H), 6.78 (t, J=7.3 Hz, 1H), 6.62 (dd, J=8.1, 2.7 Hz, 1H), 5.23 (dd, J=8.3, 4.4 Hz, 1H), 5.15-5.08 (m, 2H), 3.24 (bs, 1H), 2.72-2.41 (m, 9H), 2.38-2.30 (m, 4H), 2.24 (s, 3H), 2.17-2.12 (m, 1H), 2.01-1.96 (m, 1H), 1.50 (bs, 4H), 1.40-1.32 (m, 2H); $^{13}$C NMR (126 MHz, CDCl$_3$) δ [173.1, 172.9], 156.2, [142.44, 142.38], 136.3, [130.67, 130.66], 128.7, 128.6, 128.4, 128.2, 127.5, 127.0, 126.7, [125.94, 125.90], 120.3, 112.9, [77.91, 77.85], 66.2, [60.3, 60.1], 58.6, 55.0, 50.1, 42.6, 36.6, 29.8, 26.5, 24.8, 16.7; HRMS (ESI/[M+H]$^+$) calcd. for C$_{33}$H$_{43}$N$_2$O$_3^+$: 515.3268, found [M+H]$^+$: 515.3268; FTIR (neat) ν$_{max}$ 2932, 2849, 2797, 1731, 1491, 1454, 1238, 1119, 752, 699 cm$^{-1}$.

Benzyl 4-(4-(isoquinolin-5-ylsulfonyl)-1,4-diazepan-1-yl)-3-(piperidin-1-yl)butanoate (compound 36)

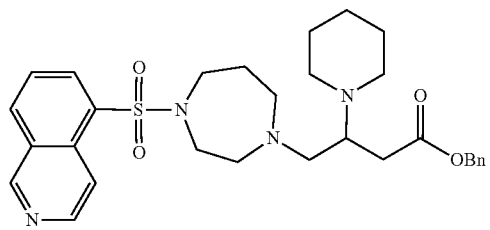 [SMILES: O=C(CC(CN1CCCN(S(=O)(=O)c2cccc3cnccc23)CC1)N1CCCCC1)OCc1ccccc1]

Compound 36 was prepared following the general procedure A (see Example 2 supra) using allenoate 2 (17.4 mg, 0.1 mmol, 1.0 equiv), piperidine (11.0 µL, 0.11 mmol, 1.1 equiv) and Fasudil (43.6 mg, 0.15 mmol, 1.5 equiv). The reaction time of the electrophilic amination step was 4 hours. The product was isolated by silica gel chromatography as a light-yellow oil (29.2 mg, 53% yield).

$^1$H NMR (500 MHz, CDCl$_3$) δ 9.32 (d, J=1.0 Hz, 1H), 8.67 (d, J=6.2 Hz, 1H), 8.44 (d, J=6.2 Hz, 1H), 8.31 (dd, J=7.4, 1.2 Hz, 1H), 8.16 (d, J=8.2 Hz, 1H), 7.73-7.63 (m, 1H), 7.37-7.25 (m, 5H), 5.07-5.00 (m, 2H), 3.47-3.27 (m, 5H), 3.16-3.06 (m, 1H), 2.78-2.56 (m, 5H), 2.53-2.26 (m, 7H), 1.84-1.66 (m, 2H), 1.51-1.41 (m, 4H), 1.36 (q, J=5.4 Hz, 2H); $^{13}$C NMR (126 MHz, CDCl$_3$) δ 173.1, 153.3, 145.2, 136.2, 134.7, 133.4, 133.1, 131.8, 129.3, 128.6, 128.4, 128.2, 126.0, 117.8, 66.2, 60.5, 58.4, 56.6, 55.0, 50.2, 48.4, 46.2, 34.9, 28.4, 26.5, 24.8; HRMS (ESI/[M+H]$^+$) calcd. for C$_{30}$H$_{39}$N$_4$O$_4$S$^+$: 551.2687, found [M+H]$^+$: 551.2691; FTIR (neat) ν$_{max}$ 2932, 1728, 1615, 1453, 1327, 1155, 1135, 709 cm$^{-1}$.

Benzyl 4-(methyl((S)-3-(naphthalen-1-yloxy)-3-(thiophen-2-yl)propyl)amino)-3-(piperidin-1-yl)butanoate (compound 37)

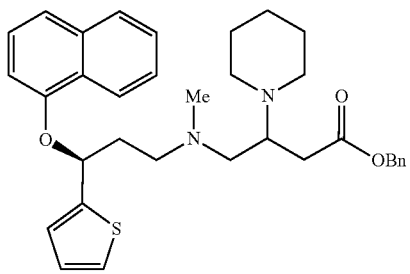 [SMILES: CN(CC[C@H](Oc1cccc2ccccc12)c1cccs1)CC(CC(=O)OCc1ccccc1)N1CCCCC1]

Compound 37 was prepared following the general procedure B (see Example 2 supra) using allenoate 2 (17.4 mg, 0.1 mmol, 1.0 equiv), N-chloropiperidine (13.1 mg, 0.11 mmol, 1.1 equiv) and Duloxetine (44.6 mg, 0.15 mmol, 1.5 equiv). The reaction time of the electrophilic amination step was 4 hours. The product was isolated by silica gel chromatography as a colorless oil (46.2 mg, 83% yield, 1:1 dr, characterized as an inseparable mixture).

$^1$H NMR (500 MHz, CDCl$_3$) δ 8.41-8.31 (m, 1H), 7.82-7.73 (m, 1H), 7.51-7.45 (m, 2H), 7.41-7.24 (m, 7H), 7.20 (dt, J=5.0, 1.2 Hz, 1H), 7.07 (t, J=3.5 Hz, 1H), 6.96-6.91 (m, 1H), 6.88 (dd, J=7.5, 5.2 Hz, 1H), 5.76 (t, J=6.5 Hz, 1H), 5.21-5.01 (m, 2H), 3.28-3.16 (m, 1H), 2.72-2.33 (m, 11H), 2.29-2.23 (m, 1H), 2.21 (s, 3H), 2.19-2.10 (m, 1H), 1.45 (d, J=4.6 Hz, 4H), 1.39-1.30 (m, 2H). $^{13}$C NMR (126 MHz, CDCl$_3$) δ [173.1, 173.0], [153.7, 153.6], 145.6, 136.3, 134.7, 128.6, 128.4, 128.2, 127.6, 126.7, 126.4, 126.3, 125.9, 125.3, 124.8, 122.3, 120.6, 107.2, 107.1, [74.64, 74.57], 66.2, [60.3, 60.1], [58.9, 58.8], 54.8, [50.09, 50.06], 42.6, [36.9, 36.8], [35.2, 34.9], 26.5, 24.8; HRMS (ESI/[M+H]$^+$) calcd. for C$_{34}$H$_{41}$N$_2$O$_3$S$^+$: 557.2832, found [M+H]$^+$: 557.2832; FTIR (neat) ν$_{max}$ 2931, 2849, 2796, 1731, 1595, 1507, 1456, 1396, 1263, 1235, 1095, 757 cm$^{-1}$.

Benzyl 4-((3S,4R)-3-((benzo[d][1,3]dioxol-5-yloxy)methyl)-4-(4-fluorophenyl)piperidin-1-yl)-3-(piperidin-1-yl)butanoate (compound 38)

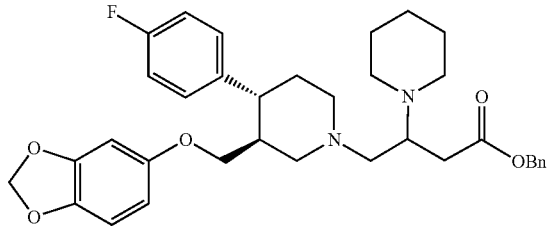 [SMILES: O=C(CC(CN1CC[C@@H](c2ccc(F)cc2)[C@H](COc2ccc3c(c2)OCO3)C1)N1CCCCC1)OCc1ccccc1]

Compound 38 was prepared following the general procedure B (see Example 2 supra) using allenoate 2 (17.4 mg, 0.1 mmol, 1.0 equiv), N-chloropiperidine (13.1 mg, 0.11 mmol, 1.1 equiv) and Duloxetine (44.6 mg, 0.15 mmol, 1.5 equiv). The reaction time of the electrophilic amination step was 4 hours. The product was isolated by silica gel chromatography as a colorless oil (37.1 mg, 63% yield, 1:1 dr, characterized as an inseparable mixture).

$^1$H NMR (500 MHz, CDCl$_3$) δ 7.44-7.29 (m, 5H), 7.14-7.06 (m, 2H), 6.94 (td, J=8.6, 1.0 Hz, 2H), 6.62 (d, J=8.5 Hz, 1H), 6.33 (t, J=2.2 Hz, 1H), 6.12 (dt, J=8.5, 2.2 Hz, 1H), 5.87 (s, 2H), 5.16 (d, J=1.9 Hz, 2H), 3.55-3.50 (m, 1H), 3.45-2.87 (m, 4H), 2.64-2.38 (m, 9H), 2.28-1.97 (m, 3H), 1.76 (s, 2H), 1.53 (s, 4H), 1.41 (d, J=4.5 Hz, 2H); $^{13}$C NMR (126 MHz, CDCl$_3$) δ [173.14, 173.07], 161.6 (d, J=244.4 Hz), [154.6, 154.5], 148.3, 141.7, 139.9, 136.3, 128.91 (d, J=10.6 Hz), 128.90, 128.7, 128.2, [115.48 (d, J=20.9 Hz), 115.45 (d, J=20.9 Hz)], 108.0, [105.7, 105.6], 101.2, [98.12, 98.06], 69.7, 66.2, [59.8, 59.7], 57.2, 55.8, 53.6, 50.2, [44.2, 44.0], [42.3, 42.1], 34.5, 29.8, 26.5, 24.9; $^{19}$F NMR (471 MHz, CDCl$_3$) δ -117.80; HRMS (ESI/[M+H]$^+$) calcd. for C$_{35}$H$_{42}$FN$_2$O$_5$$^+$: 589.3072, found [M+H]$^+$: 589.3073; FTIR (neat) ν$_{max}$ 2931, 2850, 2805, 1731, 1508, 1488, 1467, 1221, 1184, 1135, 1037, 830 cm$^{-1}$.

Benzyl 4-morpholino-3-(piperidin-1-yl)butanoate (compound 39)

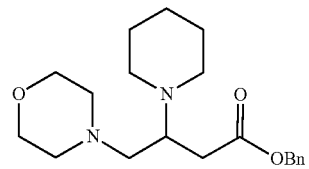 [SMILES: O=C(CC(CN1CCOCC1)N1CCCCC1)OCc1ccccc1]

Compound 39 was prepared following the general procedure A (see Example 2 supra) using allenoate 2 (17.4 mg, 0.1 mmol, 1.0 equiv), piperidine (11.0 µL, 0.11 mmol, 1.1 equiv) and morpholine (14.0 µL, 0.15 mmol, 1.5 equiv). The reaction time of the electrophilic amination step was 4 hours. The product was isolated by silica gel chromatography as a colorless oil (23.6 mg, 68% yield).

$^1$H NMR (500 MHz, CDCl$_3$) δ 7.41-7.27 (m, 5H), 5.15-5.09 (m, 2H), 3.66-3.53 (m, 4H), 3.29-3.21 (m, 1H), 2.59-2.40 (m, 9H), 2.36-2.25 (m, 5H), 1.54-1.43 (m, 4H), 1.41-1.36 (m, 2H); $^{13}$C NMR (126 MHz, CDCl$_3$) δ 173.1, 136.3, 128.6, 128.3, 128.2, 67.2, 66.2, 60.4, 59.1, 54.2, 50.1, 35.3, 26.6, 24.9; HRMS (ESI/[M+H]$^+$) calcd. for C$_{20}$H$_{31}$N$_2$O$_3$$^+$:

Benzyl 3-morpholino-4-(piperidin-1-yl)butanoate (compound 40)

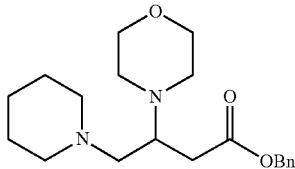 [SMILES: O=C(CC(CN1CCCCC1)N1CCOCC1)OCc1ccccc1]

Compound 40 was prepared following the general procedure A (see Example 2 supra) using allenoate 2 (17.4 mg, 0.1 mmol, 1.0 equiv), morpholine (10.0 µL, 0.11 mmol, 1.1 equiv) and piperidine (15.0 µL, 0.15 mmol, 1.5 equiv). The reaction time of the electrophilic amination step was 7 hours. The product was isolated by silica gel chromatography as a colorless oil (25.0 mg, 72% yield).

$^1$H NMR (500 MHz, CDCl$_3$) δ 7.41-7.27 (m, 5H), 5.15-5.09 (m, 2H), 3.66-3.53 (m, 4H), 3.29-3.21 (m, 1H), 2.59-2.40 (m, 9H), 2.36-2.25 (m, 3H), 1.54-1.43 (m, 4H), 1.41-1.36 (m, 2H); $^{13}$C NMR (126 MHz, CDCl$_3$) δ 173.1, 136.3, 128.6, 128.3, 128.2, 67.2, 66.2, 60.4, 59.1, 54.2, 50.1, 35.3, 26.6, 24.9; HRMS (ESI/[M+H]$^+$) calcd. for C$_{20}$H$_{31}$N$_2$O$_3^+$: 347.2329, found [M+H]$^+$: 347.2320. FTIR (neat) ν$_{max}$ 2931, 2818, 1732, 1600, 1452, 1280, 1150, 1110, 757, 698 cm$^{-1}$.

Ethyl 2-fluoro-3-(piperidin-1-yl)-4-(4-(4-(trifluoromethyl)phenyl)piperazin-1-yl)butanoate (compound 41)

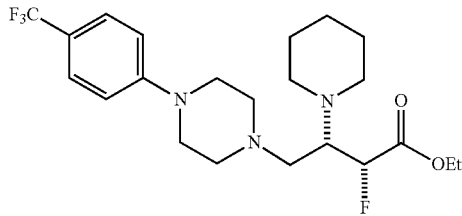 [SMILES: CCOC(=O)[C@H](F)[C@H](CN1CCN(c2ccc(C(F)(F)F)cc2)CC1)N1CCCCC1]

Compound 41 was prepared following the general procedure B (see Example 2 supra) using allenoate A1 (11.2 mg, 0.1 mmol, 1.0 equiv), N-chloropiperidine (13.1 mg, 0.11 mmol, 1.1 equiv) and 1-(4-(trifluoromethyl)phenyl)piperazine (34.5 mg, 0.15 mmol, 1.5 equiv). The reaction time of the electrophilic amination step was 4 hours. The enamine reduction was conducted under EtOH/AcOH, pH 4 at −20° C. The product was isolated by silica gel chromatography as a colorless oil (21.0 mg, 47% yield, 10:1 dr).

Major diastereomer: $^1$H NMR (500 MHz, CDCl$_3$) δ 7.47 (d, J=8.6 Hz, 2H), 6.91 (d, J=8.7 Hz, 2H), 5.23 (dd, J=48.8, 3.6 Hz, 1H), 4.39-4.18 (m, 2H), 3.31-3.21 (m, 4H), 3.19-3.05 (m, 1H), 2.84 (dt, J=10.6, 5.2 Hz, 2H), 2.72 (dt, J=9.3, 7.6 Hz, 3H), 2.64-2.56 (m, 3H), 2.48 (dt, J=10.6, 5.2 Hz, 2H), 1.51-1.42 (m, 4H), 1.40-1.29 (m, 5H); $^{13}$C NMR (126 MHz, CDCl$_3$) δ 169.8 (d, J=24.3 Hz), 153.4, 126.5 (d, J=3.4 Hz), 124.9 (q, J=270.5 Hz), 120.6 (q, J=32.7 Hz), 114.61, 92.0 (d, J=190.7 Hz), 63.4 (d, J=18.2 Hz), 61.2, 53.5, 52.6 (d, J=4.2 Hz), 51.6, 48.3, 26.9, 24.6, 14.5; $^{19}$F NMR (471 MHz, CDCl$_3$) δ −62.52, −203.37 (dd, J=48.8, 32.0 Hz); HRMS (ESI/[M+H]$^+$) calcd. for C$_{22}$H$_{32}$F$_4$N$_3$O$_2^+$: 446.2425, found [M+H]$^+$: 446.2425; FTIR (neat) ν$_{max}$ 2932, 2850, 1762, 1737, 1615, 1524, 1453, 1387, 1329, 1298, 1235, 1200, 1149, 1113, 1071, 826, 755 cm$^{-1}$.

Ethyl 4-(4-(4-bromophenyl)piperazin-1-yl)-2-fluoro-3-(piperidin-1-yl)butanoate (compound 42)

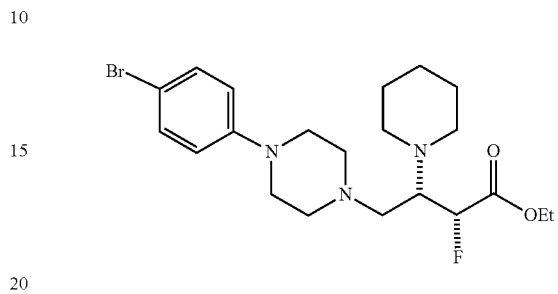

Compound 42 was prepared following the general procedure B (see Example 2 supra) using allenoate A1 (11.2 mg, 0.1 mmol, 1.0 equiv), N-chloropiperidine (13.1 mg, 0.11 mmol, 1.1 equiv) and 1-(4-bromophenyl)piperazine (36.2 mg, 0.15 mmol, 1.5 equiv). The reaction time of the electrophilic amination step was 4 hours. The enamine reduction was conducted under EtOH/AcOH, pH 4 at −20° C. The product was isolated by silica gel chromatography as a colorless oil (18.3 mg, 40% yield, 12:1 dr).

Major diastereomer: $^1$H NMR (500 MHz, CDCl$_3$) δ 7.37-7.30 (m, 2H), 6.81-6.74 (m, 2H), 5.22 (dd, J=48.8, 3.5 Hz, 1H), 4.37-4.17 (m, 2H), 3.21-3.04 (m, 5H), 2.83 (dt, J=10.5, 5.2 Hz, 2H), 2.76-2.66 (m, 3H), 2.58 (dt, J=15.6, 5.3 Hz, 3H), 2.47 (dt, J 10.5, 5.1 Hz, 2H), 1.52-1.42 (m, 4H), 1.40-1.31 (m, 5H); $^{13}$C NMR (126 MHz, CDCl$_3$) δ 169.8 (d, J=24.2 Hz), 150.5, 132.0, 117.7, 111.9, 92.0 (d, J=190.6 Hz), 63.4 (d, J=18.3 Hz), 61.2 (s), 53.6, 52.6 (d, J=4.2 Hz), 51.6, 49.3, 27.0, 24.6, 14.5; $^{19}$F NMR (471 MHz, CDCl$_3$) δ −203.38 (dd, J=48.8, 32.0 Hz); HRMS (ESI/[M+H]$^+$) calcd. for C$_{21}$H$_{32}$BrFN$_3$O$_2^+$: 456.1656, found [M+H]$^+$: 456.1655; FTIR (neat) ν$_{max}$ 2931, 2818, 1761, 1736, 1589, 1494, 1452, 1297, 1233, 1146, 1127, 1094, 1033, 1010, 814 cm$^{-1}$.

Ethyl 2-fluoro-3-morpholino-4-(4-phenylpiperazin-1-yl)butanoate (compound 43)

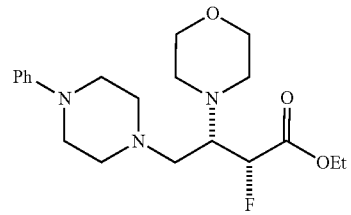 [SMILES: CCOC(=O)[C@H](F)[C@H](CN1CCN(c2ccccc2)CC1)N1CCOCC1]

Compound 43 was prepared following the general procedure B (see Example 2 supra) using allenoate A1 (11.2 mg, 0.1 mmol, 1.0 equiv), N-chloromorpholine (13.3 mg, 0.11 mmol, 1.1 equiv) and 1-phenylpiperazine (24.3 mg, 0.15 mmol, 1.5 equiv). The reaction time of the electrophilic amination step was 7 hours. The enamine reduction was conducted under EtOH/AcOH, pH 4 at −20° C. The product was isolated by silica gel chromatography as a colorless oil (16.3 mg, 43% yield, 13:1 dr).

Major diastereomer: $^1$H NMR (500 MHz, CDCl$_3$) δ 7.31-7.21 (m, 2H), 6.95-6.89 (m, 2H), 6.86 (t, J=7.3 Hz, 1H), 5.24 (dd, J=48.5, 3.2 Hz, 1H), 4.40-4.23 (m, 2H), 3.60 (t, J=4.6 Hz, 4H), 3.27-3.09 (m, 5H), 2.99-2.89 (m, 2H), 2.79-2.67 (m, 4H), 2.67-2.60 (m, 2H), 2.60-2.52 (m, 2H), 1.34 (t, J=7.1 Hz, 3H); $^{13}$C NMR (126 MHz, CDCl$_3$) δ 169.5 (d, J=23.9 Hz), 151.4 (s), 129.3, 119.9, 116.2, 92.0 (d, J=190.8 Hz), 67.8, 62.72 (d, J=18.2 Hz), 61.3, 53.8, 52.64 (d, J=4.0 Hz), 50.7, 49.5, 14.6; $^{19}$F NMR (471 MHz, CDCl$_3$) δ −204.04 (dd, J=48.5, 32.2 Hz); HRMS (ESI/[M+H]$^+$) calcd. for C$_{20}$H$_{31}$FN$_3$O$_3^+$: 380.2344, found [M+H]$^+$: 380.2345; FTIR (neat) ν$_{max}$ 2956, 2823, 1761, 1737, 1600, 1496, 1454, 1372, 1291, 1231, 1215, 1154, 1117, 1009, 754 cm$^{-1}$.

Ethyl 2-fluoro-4-(4-phenylpiperazin-1-yl)-3-(4-phenylpiperidin-1-yl)butanoate (compound 44)

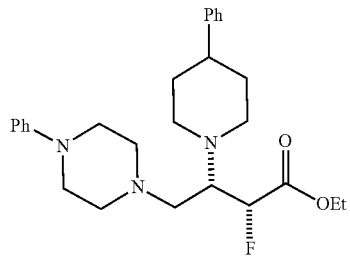 [SMILES: CCOC(=O)[C@H](F)[C@H](CN1CCN(c2ccccc2)CC1)N1CCC(c2ccccc2)CC1]

Compound 44 was prepared following the general procedure B (see Example 2 supra) using allenoate A1 (11.2 mg, 0.1 mmol, 1.0 equiv), N-chloro-4-phenylpiperidine (21.5 mg, 0.11 mmol, 1.1 equiv) and 1-phenylpiperazine (24.3 mg, 0.15 mmol, 1.5 equiv). The reaction time of the electrophilic amination step was 6 hours. The enamine reduction was conducted under EtOH/AcOH, pH 4 at −20° C. The product was isolated by silica gel chromatography as a colorless oil (18.2 mg, 40% yield, 6:1 dr).

Major diastereomer: $^1$H NMR (500 MHz, CDCl$_3$) δ 7.31-7.25 (m, 4H), 7.23-7.15 (m, 3H), 6.94 (d, J=7.9 Hz, 2H), 6.87 (t, J=7.3 Hz, 1H), 5.26 (dd, J=48.8, 3.5 Hz, 1H), 4.45-4.19 (m, 2H), 3.32-3.10 (m, 6H), 2.90-2.72 (m, 5H), 2.70-2.61 (m, 3H), 2.52 (td, J=11.4, 2.1 Hz, 1H), 2.42 (tt, J=12.1, 3.6 Hz, 1H), 1.83-1.73 (m, 2H), 1.70-1.57 (m, 2H), 1.36 (t, J=7.1 Hz, 3H); $^{13}$C NMR (126 MHz, CDCl$_3$) δ 169.8 (d, J=24.3 Hz), 151.4, 146.7, 129.3, 128.5, 126.9, 126.2, 119.9, 116.2, 92.0 (d, J=190.5 Hz), 62.95 (d, J=18.2 Hz), 61.3, 53.8, 53.6, 52.93 (d, J=3.8 Hz), 49.5, 49.0 (d, J=3.9 Hz), 42.7, 34.9, 33.9, 14.6; $^{19}$F NMR (471 MHz, CDCl$_3$) δ −203.49 (dd, J=48.7, 31.9 Hz); HRMS (ESI/[M+H]$^+$) calcd. for C$_{27}$H$_{37}$FN$_3$O$_3^+$: 454.2864, found [M+H]$^+$: 454.2865; FTIR (neat) ν$_{max}$ 2932, 2817, 1763, 1731, 1599, 1494, 1452, 1371, 1297, 1231, 1147, 1094, 1029, 1011, 924, 757, 698 cm$^{-1}$.

Ethyl 2-fluoro-4-(4-phenylpiperazin-1-yl)-3-(piperidin-1-yl)butanoate-3-d (compound 45)

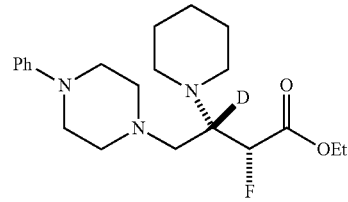 [SMILES: [2H][C@](CN1CCN(c2ccccc2)CC1)([C@@H](F)C(=O)OCC)N1CCCCC1]

Compound 45 was prepared following the general procedure B (see Example 2 supra) using allenoate A1 (11.2 mg, 0.1 mmol, 1.0 equiv), N-chloropiperidine (13.1 mg, 0.11 mmol, 1.1 equiv) and 1-phenylpiperazine (24.3 mg, 0.15 mmol, 1.5 equiv). The reaction time of the electrophilic amination step was 4 hours. NaBD$_3$CN was used instead of NaBH$_3$CN. The enamine reduction was conducted under EtOH/AcOH, pH 4 at −20° C. The product was isolated by silica gel chromatography as a colorless oil (13.3 mg, 35% yield, 14:1 dr).

Major diastereomer: $^1$H NMR (500 MHz, CDCl$_3$) δ 7.32-7.18 (m, 2H), 6.92 (dd, J=8.7, 0.8 Hz, 2H), 6.85 (t, J=7.3 Hz, 1H), 5.23 (d, J=48.8 Hz, 1H), 4.39-4.14 (m, 2H), 3.24-3.07 (m, 4H), 2.84 (dt, J=10.6, 5.2 Hz, 2H), 2.72 (dd, J=11.5, 8.2 Hz, 3H), 2.65-2.54 (m, 3H), 2.48 (dt, J=10.6, 5.2 Hz, 2H), 1.51-1.43 (m, 4H), 1.40-1.30 (m, 5H); $^{13}$C NMR (126 MHz, CDCl$_3$) δ 169.8 (d, J=24.2 Hz), 151.5, 129.2, 119.8, 116.2, 92.0 (d, J=190.2 Hz), 61.2, 53.8, 52.6 (d, J=4.2 Hz), 51.5, 49.5, 27.0, 24.6, 14.5. The quaternary carbon connected with deuterium was omitted; $^{19}$F NMR (471 MHz, CDCl$_3$) δ −203.67 (d, J=48.8 Hz); HRMS (ESI/[M+H]$^+$) calcd. for C$_{21}$H$_{32}$DFN$_3$O$_2^+$: 379.2614, found [M+H]$^+$: 379.2613; FTIR (neat) ν$_{max}$ 2931, 2816, 1761, 1738, 1600, 1489, 1456, 1299, 1233, 1098, 1007, 755 cm$^{-1}$.

1-phenyl-4-(3-(phenylsulfonyl)-2-(piperidin-1-yl)propyl)piperazine (compound 46)

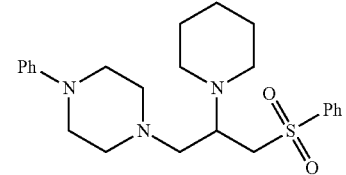 [SMILES: O=S(=O)(CC(CN1CCN(c2ccccc2)CC1)N1CCCCC1)c1ccccc1]

Compound 46 was prepared following the general procedure B (see Example 2 supra) using allene A5 (18.0 mg, 0.1 mmol, 1.0 equiv), N-chloropiperidine (13.1 mg, 0.11 mmol, 1.1 equiv) and 1-phenylpiperazine (24.3 mg, 0.15 mmol, 1.5 equiv). The reaction time of the electrophilic amination step was 2 hours. The product was isolated by silica gel chromatography as a colorless oil (25.2 mg, 59% yield).

$^1$H NMR (500 MHz, CDCl$_3$) δ 8.00-7.85 (m, 2H), 7.70-7.56 (m, 1H), 7.58-7.41 (m, 2H), 7.34-7.18 (m, 2H), 6.92 (m, 2H), 6.85 (m, 1H), 3.43 (m, 1H), 3.39-3.30 (m, 2H), 3.15 (t, J=5.0 Hz, 3H), 2.77-2.63 (m, 2H), 2.57-2.35 (m, 5H), 2.40-2.20 (m, 3H), 1.31-1.13 (m, 5H), 1.05 (m, 2H); $^{13}$C NMR (126 MHz, CDCl$_3$) δ 151.4, 141.2, 133.2, 129.3, 129.0, 128.2, 119.8, 116.2, 57.9, 56.4, 55.5, 53.6, 49.5, 49.4, 25.9, 24.6; HRMS (ESI/[M+H]$^+$) calcd. for $C_{24}H_{34}N_3O_2S^+$: 428.2366, found [M+H]$^+$: 428.2365; FTIR (neat) $\nu_{max}$ 2932, 2917, 1599, 1497, 1446, 1300, 1141, 752, 688.

1-phenyl-4-(2-(piperidin-1-yl)-3-((3-(trifluoromethyl)phenyl)sulfonyl)propyl)piperazine (compound 47)

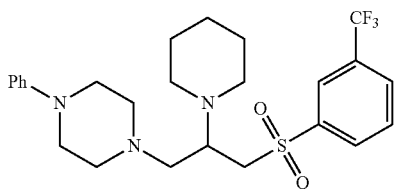 [SMILES: O=S(=O)(CC(CN1CCN(c2ccccc2)CC1)N1CCCCC1)c1cccc(C(F)(F)F)c1]

Compound 47 was prepared following the general procedure B (see Example 2 supra) using allene A6 (24.8 mg, 0.1 mmol, 1.0 equiv), N-chloropiperidine (13.1 mg, 0.11 mmol, 1.1 equiv) and 1-phenylpiperazine (24.3 mg, 0.15 mmol, 1.5 equiv). The reaction time of the electrophilic amination step was 2 hours. The product was isolated by silica gel chromatography as a colorless oil (21.8 mg, 44% yield).

$^1$H NMR (500 MHz, CDCl$_3$) δ 8.20 (s, 1H), 8.11 (d, J=7.7 Hz, 1H), 7.88 (d, J=7.7 Hz, 1H), 7.69 (t, J=7.8 Hz, 1H), 7.27 (t, J=7.8 Hz, 2H), 6.92 (d, J=8.1 Hz, 2H), 6.86 (t, J=7.2 Hz, 1H), 3.57 (d, J 12.5 Hz, 1H), 3.46-3.30 (m, 2H), 3.17 (t, J=4.8 Hz, 3H), 2.83-2.63 (m, 2H), 2.60-2.37 (m, 4H), 2.36-2.16 (m, 3H), 1.35-1.07 (m, 6H), 0.91 (s, 2H); $^{13}$C NMR (126 MHz, CDCl$_3$) δ 151.4, 142.7, 131.7 (q, J=33.4 Hz), 131.5, 129.8 (d, J=3.1 Hz), 129.8, 129.3, 125.5 (d, J=3.4 Hz), 123.4 (q, J=273.1 Hz), 119.9, 116.3, 58.0, 55.7, 55.5, 53.6, 49.4, 49.3, 25.7, 24.4; $^{19}$F NMR (471 MHz, CDCl$_3$) δ −63.92; HRMS (ESI/[M+H]$^+$) calcd. for $C_{25}H_{33}F_3N_3O_2S^+$: 496.2240, found [M+H]$^+$: 496.2240; FTIR (neat) $\nu_{max}$ 2935, 2817, 1599, 1501, 1453, 1326, 1300, 1140, 769, 694.

1-phenyl-4-(2-(piperidin-1-yl)-3-(thiophen-3-ylsulfonyl)propyl)piperazine (compound 48)

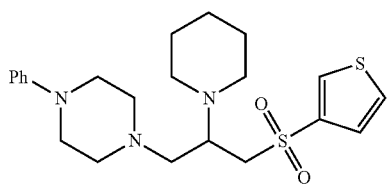 [SMILES: O=S(=O)(CC(CN1CCN(c2ccccc2)CC1)N1CCCCC1)c1ccsc1]

Compound 48 was prepared following the general procedure B (see Example 2 supra) using allene A7 (18.6 mg, 0.1 mmol, 1.0 equiv), N-chloropiperidine (13.1 mg, 0.11 mmol, 1.1 equiv) and 1-phenylpiperazine (24.3 mg, 0.15 mmol, 1.5 equiv). The reaction time of the electrophilic amination step was 2 h. The product was isolated by silica gel chromatography as a colorless oil (21.2 mg, 49% yield).

$^1$H NMR (500 MHz, CDCl$_3$) δ 7.70 (m, 2H), 7.43-7.20 (m, 2H), 7.16 (dd, J=5.0, 3.8 Hz, 1H), 7.06-6.91 (m, 2H), 6.88 (tt, J=7.3, 1.1 Hz, 1H), 3.59-3.50 (m, 1H), 3.52-3.33 (m, 2H), 3.18 (t, J=5.0 Hz, 3H), 2.76 (m, 2H), 2.54 (dh, J=18.3, 5.1 Hz, 5H), 2.45-2.20 (m, 4H), 1.41-1.14 (m, 6H); $^{13}$C NMR (126 MHz, CDCl$_3$) 151.5, 142.3, 133.7, 133.4, 129.3, 127.7, 119.9, 116.2, 58.1, 57.0, 56.6, 53.6, 49.7, 49.4, 26.3, 24.7; HRMS (ESI/[M+H]$^+$) calcd. for $C_{22}H_{32}N_3O_2S_2^+$: 434.1930, found [M+H]$^+$: 434.1928; FTIR (neat) $\nu_{max}$ 2931, 2817, 1599, 1305, 1282, 1137, 1010, 763.

1-(3-((4'-chloro-[1,1'-biphenyl]-4-yl)sulfonyl)-2-(piperidin-1-yl)propyl)-4-phenylpiperazine (compound 49)

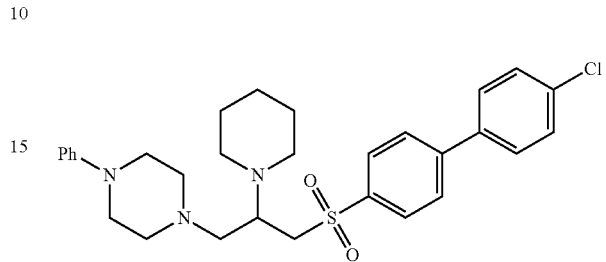

Compound 49 was prepared following the general procedure B (see Example 2 supra) using allene A8 (29.0 mg, 0.1 mmol, 1.0 equiv), N-chloropiperidine (13.1 mg, 0.11 mmol, 1.1 equiv) and 1-phenylpiperazine (24.3 mg, 0.15 mmol, 1.5 equiv). The reaction time of the electrophilic amination step was 2 hours. The product was isolated by silica gel chromatography as a colorless oil (47.9 mg, 89% yield).

$^1$H NMR (500 MHz, CDCl$_3$) δ 7.98 (d, J=8.3 Hz, 2H), 7.69 (d, J=8.3 Hz, 2H), 7.55-7.48 (m, 2H), 7.48-7.42 (m, 2H), 7.32-7.22 (m, 2H), 6.91 (d, J=7.9 Hz, 2H), 6.86 (t, J=7.3 Hz, 1H), 3.48 (q, J=7.3 Hz, 1H), 3.42-3.30 (m, 2H), 3.15 (s, 3H), 2.81-2.66 (m, 2H), 2.59-2.43 (m, 4H), 2.34 (dd, J=19.0, 8.6 Hz, 3H), 1.25 (d, J=6.6 Hz, 6H), 1.09 (s, 2H); $^{13}$C NMR (126 MHz, CDCl$_3$) δ 151.4, 145.0, 140.2, 138.1, 135.0, 129.5, 129.3, 128.9, 128.8, 127.6, 119.9, 116.2, 57.9, 56.4, 55.7, 53.6, 49.6, 49.4, 26.0, 24.6; HRMS (ESI/[M+H]$^+$) calcd. for $C_{30}H_{37}ClN_3O_2S^+$: 538.2289, found [M+H]$^+$: 538.2284; FTIR (neat) $\nu_{max}$ 2939, 2819, 1598, 1502, 1453, 1387, 1297, 1237, 1142, 1089, 820, 762.

2-(3-((4-chlorophenyl)sulfonyl)-2-(piperidin-1-yl)propyl)isoindoline-1,3-dione (compound 50)

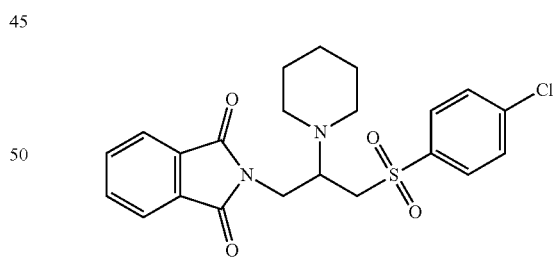

Compound 50 was prepared following the general procedure B (see Example 2 supra) using allene A8 (21.5 mg, 0.1 mmol, 1.0 equiv), N-chloropiperidine (13.1 mg, 0.11 mmol, 1.1 equiv) and phthalimide (22.1 mg, 0.15 mmol, 1.5 equiv). The reaction time of the electrophilic amination step was 2 hours. The product was isolated by silica gel chromatography as a colorless oil (18.8 mg, 42% yield).

$^1$H NMR (500 MHz, CDCl$_3$) δ 7.89 (d, J=8.5 Hz, 2H), 7.84 (dd, J=5.4, 3.1 Hz, 2H), 7.72 (dd, J=5.4, 3.0 Hz, 2H), 7.53 (d, J=8.6 Hz, 2H), 3.89 (dd, J=13.8, 7.5 Hz, 1H), 3.79 (dd, J=13.9, 7.0 Hz, 1H), 3.53-3.37 (m, 2H), 3.06 (dd, J=15.9, 8.0 Hz, 1H), 2.52-2.43 (m, 2H), 2.27-2.16 (m, 2H), 1.27 (d, J=14.4 Hz, 6H); $^{13}$C NMR (126 MHz, CDCl$_3$) δ 168.4, 140.6, 138.0, 134.2, 132.2, 130.0, 129.7, 123.4, 58.2, 54.5, 49.5, 38.1, 26.0, 24.5; HRMS (ESI/[M+H]$^+$) calcd. for C$_{22}$H$_{24}$ClN$_2$O$_4$S$^+$: 447.1140, found [M+H]$^+$: 447.1138; FTIR (neat) ν$_{max}$ 2933, 2953, 1713, 1396, 1304, 1145, 1087, 774, 715.

4-(1-((4-chlorophenyl)sulfonyl)-3-(4-phenylpiperazin-1-yl)propan-2-yl)morpholine (compound 51)

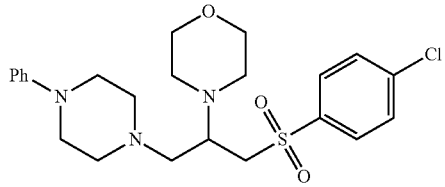 [SMILES: O=S(=O)(CC(CN1CCN(c2ccccc2)CC1)N1CCOCC1)c1ccc(Cl)cc1]

Compound 51 was prepared following the general procedure B (see Example 2 supra) using allene A9 (21.5 mg, 0.1 mmol, 1.0 equiv), N-4-chloromorpholine (13.3 mg, 0.11 mmol, 1.1 equiv) and 1-phenylpiperazine (24.3 mg, 0.15 mmol, 1.5 equiv). The reaction time of the electrophilic amination step was 2 hours. The product was isolated by silica gel chromatography as a colorless oil (19.5 mg, 42% yield).

$^1$H NMR (500 MHz, CDCl$_3$) δ 7.90-7.82 (m, 2H), 7.58-7.49 (m, 2H), 7.30-7.23 (m, 2H), 6.92 (d, J=7.8 Hz, 2H), 6.86 (t, J=7.3 Hz, 1H), 3.47 (dd, J=14.1, 2.6 Hz, 1H), 3.44-3.36 (m, 3H), 3.32 (dd, J=14.1, 8.9 Hz, 1H), 3.30-3.22 (m, 2H), 3.16 (t, J=4.9 Hz, 4H), 2.76-2.67 (m, 2H), 2.60-2.47 (m, 5H), 2.47-2.38 (m, 2H), 2.30 (dd, J=12.5, 9.1 Hz, 1H); $^{13}$C NMR (126 MHz, CDCl$_3$) δ 151.3, 140.2, 139.7, 129.7, 129.5, 129.3, 120.0, 116.3, 66.9, 57.4, 56.3, 55.7, 53.6, 49.4, 48.7; HRMS (ESI/[M+H]$^+$) calcd. for C$_{23}$H$_{31}$ClN$_3$O$_3$S$^+$: 464.1769, found [M+H]$^+$: 464.1766; FTIR (neat) ν$_{max}$ 2923, 2822, 1599, 1496, 1303, 1147, 1087, 1004, 759.

1-(3-((4-chlorophenyl)sulfonyl)-2-(piperidin-1-yl)propyl)-4-phenylpiperidine (compound 52)

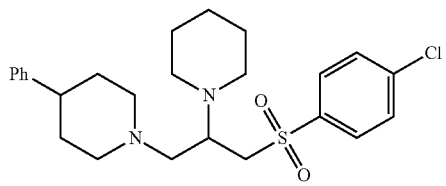 [SMILES: O=S(=O)(CC(CN1CCC(c2ccccc2)CC1)N1CCCCC1)c1ccc(Cl)cc1]

Compound 52 was prepared following the general procedure B (see Example 2 supra) using allene A9 (21.5 mg, 0.1 mmol, 1.0 equiv), N-chloropiperidine (13.1 mg, 0.11 mmol, 1.1 equiv) and 1-chloro-4-phenylpiperidine (29.2 mg, 0.15 mmol, 1.5 equiv). The reaction time of the electrophilic amination step was 2 hours. The product was isolated by silica gel chromatography as a colorless oil (26.2 mg, 57% yield).

$^1$H NMR (500 MHz, CDCl$_3$) δ 7.90-7.82 (m, 2H), 7.53-7.46 (m, 2H), 7.34-7.27 (m, 2H), 7.24-7.14 (m, 3H), 3.49 (t, J=10.7 Hz, 1H), 3.40-3.24 (m, 2H), 3.04 (d, J=11.1 Hz, 1H), 2.82 (d, J=11.2 Hz, 1H), 2.53-2.40 (m, 4H), 2.35-2.27 (m, 2H), 2.26-2.16 (m, 2H), 1.97 (td, J=11.7, 2.4 Hz, 1H), 1.79 (dd, J=13.0, 2.0 Hz, 2H), 1.76-1.64 (m, 2H), 1.34-1.15 (m, 4H), 1.08-0.97 (m, 2H); $^{13}$C NMR (126 MHz, CDCl$_3$) δ 146.4, 139.9, 139.7, 129.8, 129.2, 128.6, 127.0, 126.3, 58.2, 56.21, 56.16, 55.9, 53.5, 49.4, 42.7, 34.0, 33.5, 25.9, 24.6; HRMS (ESI/[M+H]$^+$) calcd. for C$_{25}$H$_{34}$ClN$_2$O$_2$S$^+$: 461.2024, found [M+H]$^+$: 461.2020; FTIR (neat) ν$_{max}$ 2933, 2850, 1582, 1306, 1143, 1087, 777, 699.

Example 7

Aminoetherification of Allenes and Optimization of Reaction Conditions

General Procedure A of Aminoetherification: To an oven-dried 8 mL vial wrapped with aluminum foil and equipped with a stir bar was added the indicated amine (0.11 mmol, 1.1 equiv.), t-BuOCl (14.0 μL, 0.12 mmol, 1.2 equiv.), and CH$_3$CN (2.0 mL) under argon atmosphere. The reaction mixture was stirred for 1 hour at rt. Then, tetrabutylammonium iodide (TBAI, 55.4 mg, 0.15 mmol, 1.5 equiv) and allene (0.1 mmol, 1.0 equiv) were added and the reaction mixture was stirred for 4-8 hours (the conversion of allene was monitored by TLC). After the indicated time, Cs$_2$CO$_3$ (48.9 mg, 0.15 mmol, 1.5 equiv.) and the corresponding phenol (0.15 mmol, 1.5 equiv.) were added. The reaction mixture was stirred at 60° C. for 24 hours.

Subsequently, NaBH$_3$CN (0.2 mmol) and a co-solvent of MeOH/AcOH (pH=4, 1.0 mL) were added to the reaction mixture. After 1.5 hours, the reaction was quenched with a saturated aqueous solution of NaHCO$_3$, extracted with CH$_2$Cl$_2$ for three times. The combined organic extracts were dried over Na$_2$SO$_4$, filtered, and concentrated under reduced pressure. The resulting crude mixture was purified by flash column chromatography on silica gel (hexanes/EtOAc/Et$_3$N) to afford the desired compound.

General Procedure B of Aminoetherification: To an oven-dried 10 mL vial wrapped with aluminum foil and equipped with a stir bar was added allene (0.1 mmol, 1.0 equiv.), N-chloropiperidine (13.1 mg, 0.11 mmol, 1.1 equiv.), tetrabutylammonium iodide (TBAI, 55.4 mg, 0.15 mmol, 1.5 equiv.) and CH$_3$CN (2.0 mL) under argon atmosphere. The reaction mixture was stirred for 4 hours at rt before Cs$_2$CO$_3$ (48.9 mg, 0.15 mmol, 1.5 equiv.) and the corresponding phenol were added. The reaction mixture was then stirred at 60° C. for 24 hours. Subsequently, NaBH$_3$CN (0.2 mmol) and a co-solvent of MeOH/AcOH (pH=4, 1.0 mL) were added to the reaction mixture. After 1.5 hours, the reaction was quenched with a saturated aqueous solution of NaHCO$_3$ and extracted with CH$_2$Cl$_2$ for three times. The combined organic extracts were dried over Na$_2$SO$_4$, filtered, and concentrated under reduced pressure. The resulting crude mixture was purified by flash column chromatography on silica gel (hexanes/EtOAc/Et$_3$N) to afford the desired compound.

Figure 4:
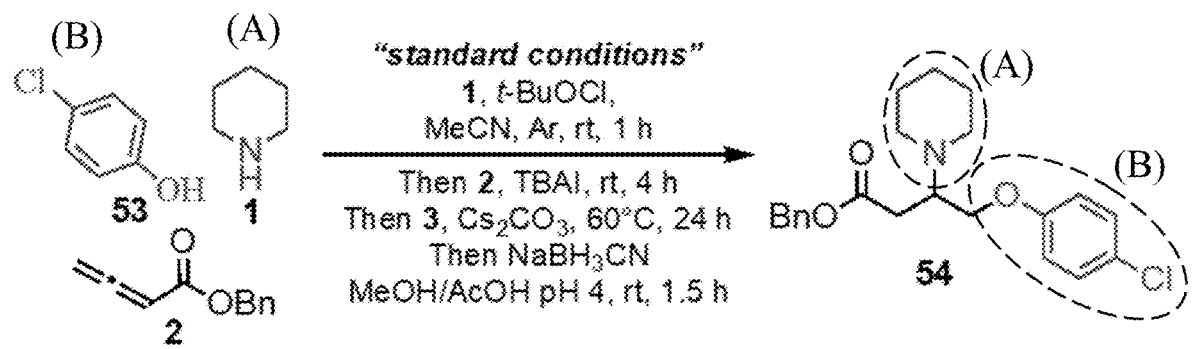
FIG. 4 illustrates parameters for an optimization of one-pot amino-etherification conditions.

Studies were also performed to optimize the reaction conditions for the aminoetherification of allenes. As shown in FIG. 4, t-BuOCl was a superior chlorination reagent and TBAI worked better that KI. The product (54) was produced in 73% yield.

Example 8

Scope of Substrates of Aminoetherification

Figure 5:
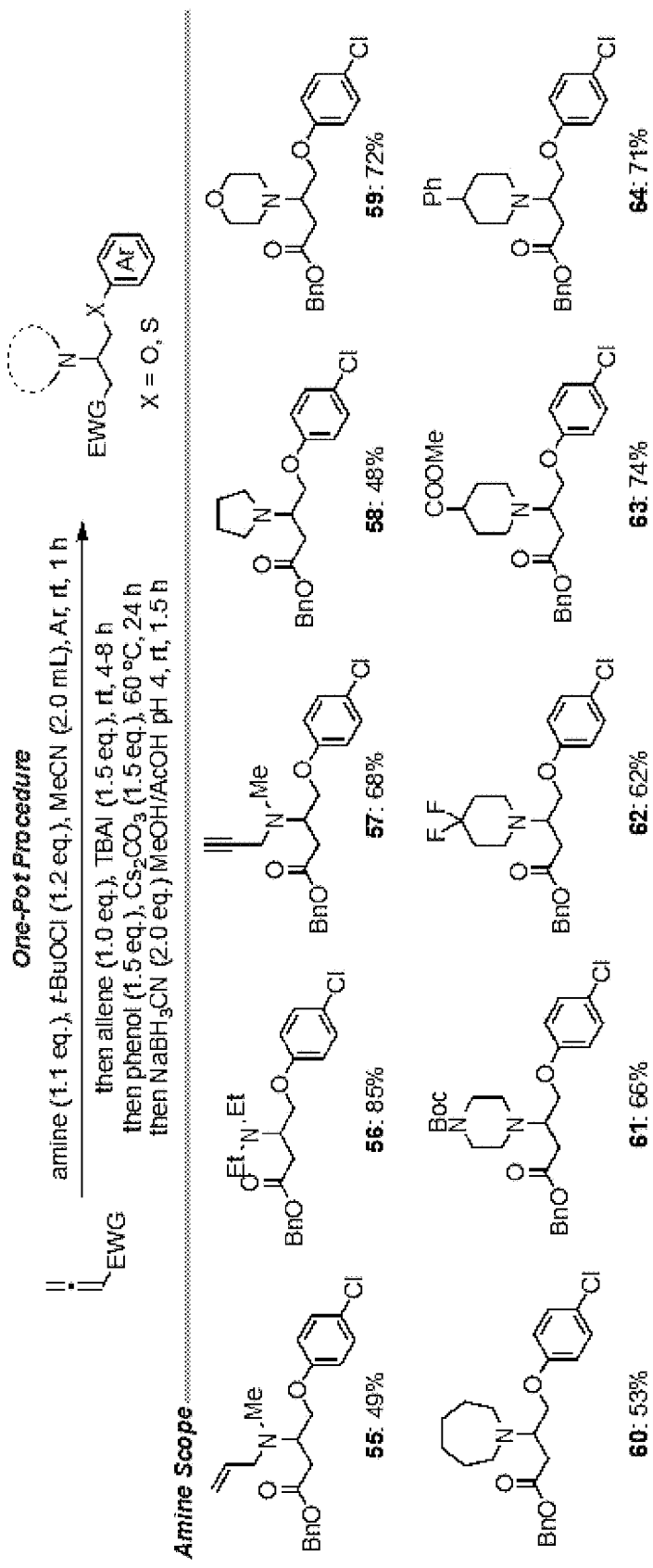
FIG. 5 illustrates amino-etherification products synthesized using the methods hereof.
Figure 5:
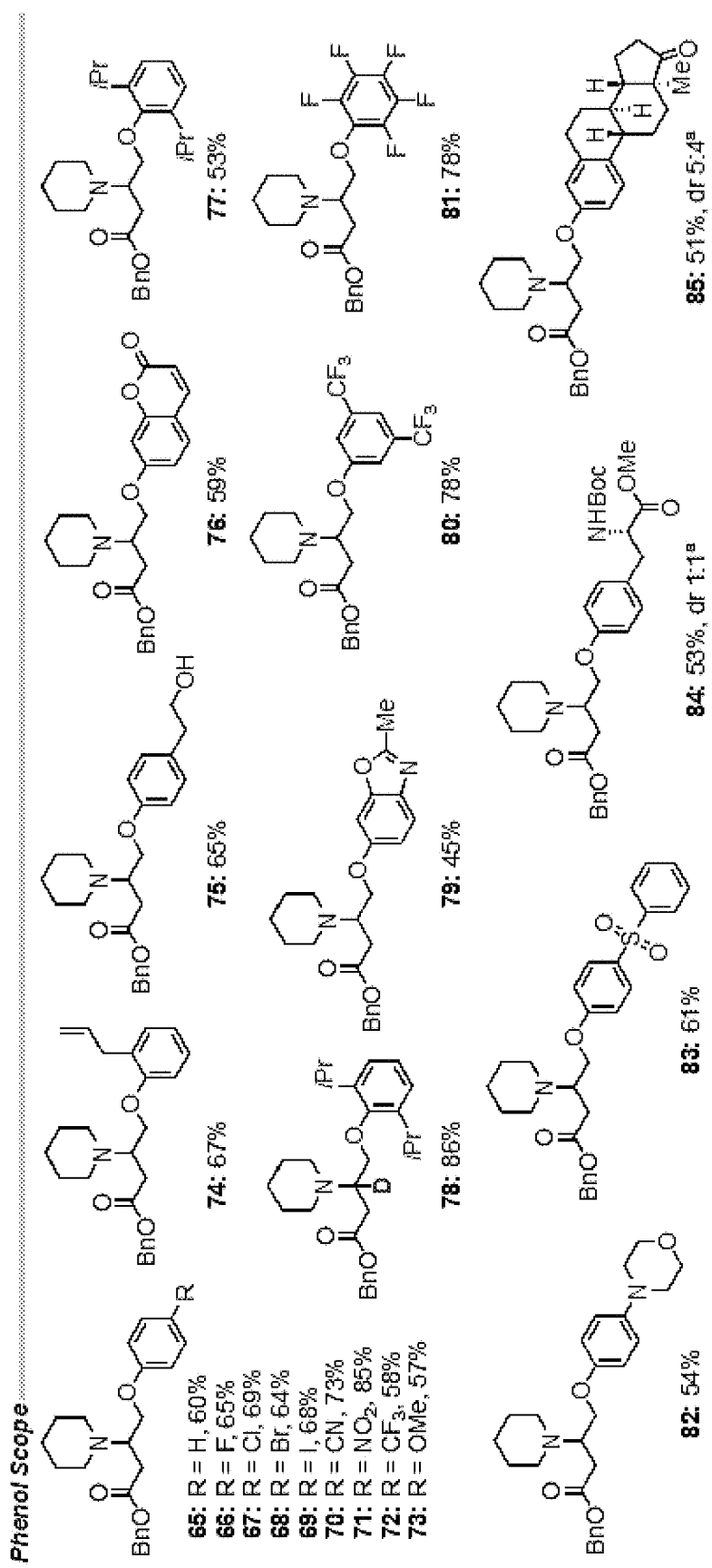
Figure 5:
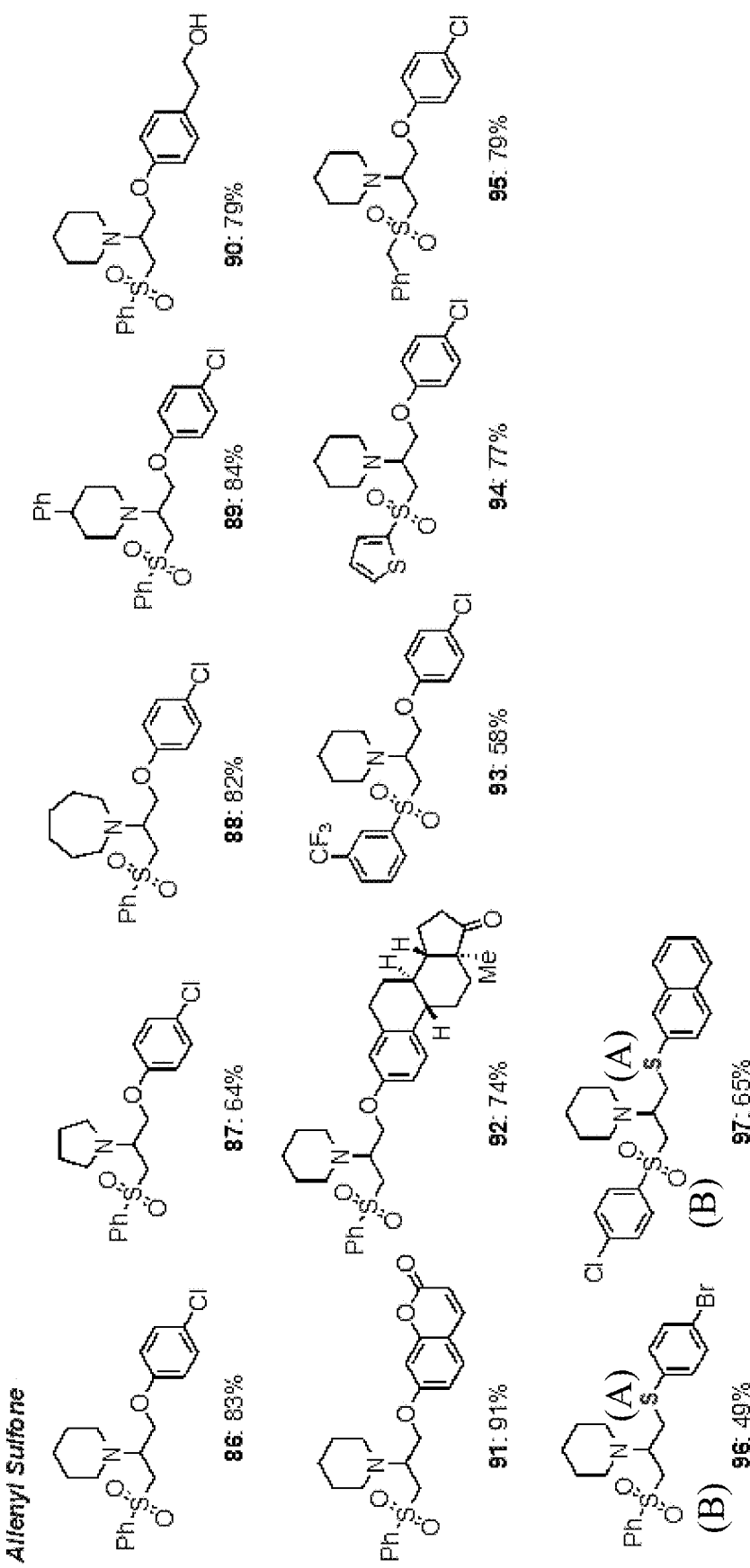

Substrate scope of the aminoetherification was investigated (summarized in FIG. 5). Similar to the diamination reaction, the aminoetherification featured broad substrate scope. Notably, thiophenols can be used as nucleophiles as well (96 and 97).

Benzyl 3-(allyl(methyl)amino)-4-(4-chlorophenoxy)butanoate (compound 55)

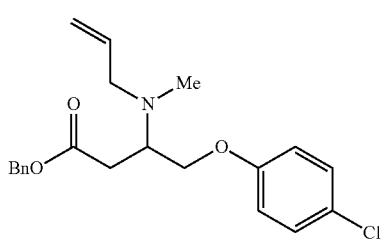 [SMILES: C=CCN(C)C(COc1ccc(Cl)cc1)CC(=O)OCc1ccccc1]

Compound 55 was prepared following the general procedure A (see Example 7 supra) (18.3 mg, 49% yield). $^1$H NMR (500 MHz, CDCl$_3$) δ 7.39-7.29 (m, 5H), 7.24-7.17 (m, 2H), 6.81-6.74 (m, 2H), 5.81-5.70 (m, 1H), 5.19-5.06 (m, 4H), 4.06 (dd, J=9.6, 5.8 Hz, 1H), 3.93 (dd, J=9.6, 5.7 Hz, 1H), 3.65-3.57 (m, 1H), 3.24-3.12 (m, 2H), 2.72-2.58 (m, 2H), 2.31 (s, 3H); $^{13}$C NMR (126 MHz, CDCl$_3$) δ 172.1, 157.3, 136.4, 136.0, 129.4, 128.7, 128.40, 128.36, 125.9, 117.3, 115.9, 67.9, 66.5, 58.4, 57.9, 37.5, 34.0; HRMS (ESI/[M+H]$^+$) calcd. for C$_{21}$H$_{25}$ClNO$_3^+$: 374.1517, found [M+H]$^+$: 374.1522; FTIR (neat) ν$_{max}$ 3067, 2857, 1732, 1491, 1241, 1170, 920, 824 cm$^{-1}$.

Benzyl 4-(4-chlorophenoxy)-3-(diethylamino)butanoate (compound 56)

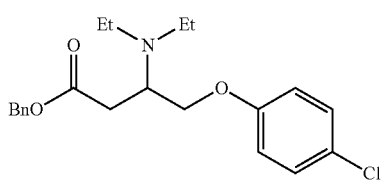 [SMILES: CCN(CC)C(COc1ccc(Cl)cc1)CC(=O)OCc1ccccc1]

Compound 56 was prepared following the general procedure A (see Example 7 supra) (32.0 mg, 85% yield). $^1$H NMR (500 MHz, CDCl$_3$) δ 7.37-7.30 (m, 5H), 7.24-7.17 (m, 2H), 6.79-6.73 (m, 2H), 5.17-5.08 (m, 2H), 4.04 (dd, J=9.3, 5.3 Hz, 1H), 3.87 (dd, J=9.3, 6.8 Hz, 1H), 3.72-3.64 (m, 1H), 2.67-2.52 (m, 6H), 1.02 (t, J=7.1 Hz, 6H); $^{13}$C NMR (126 MHz, CDCl$_3$) δ 172.4, 157.4, 136.1, 129.4, 128.6, 128.5, 128.3, 125.8, 115.9, 68.6, 66.5, 56.22 (s), 44.3, 34.9, 14.7; HRMS (ESI/[M+H]$^+$) calcd. for C$_{21}$H$_{27}$ClNO$_3^+$: 376.1764, found [M+H]$^+$: 376.1762; FTIR (neat) ν$_{max}$ 2970, 2971, 1732, 1491, 1240, 823, 748, 697 cm$^{-1}$.

Benzyl 4-(4-chlorophenoxy)-3-(methyl(prop-2-yn-1-yl)amino)butanoate (compound 57)

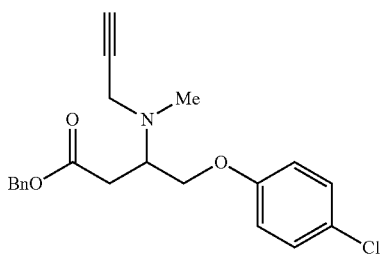 [SMILES: C#CCN(C)C(COc1ccc(Cl)cc1)CC(=O)OCc1ccccc1]

Compound 57 was prepared following the general procedure A (see Example 7 supra) (25.3 mg, 68% yield). $^1$H NMR (500 MHz, CDCl$_3$) δ 7.33 (s, 5H), 7.24-7.16 (m, 2H), 6.82-6.75 (m, 2H), 5.13 (d, J=2.6 Hz, 2H), 4.12 (dd, J=9.7, 5.3 Hz, 1H), 4.02 (dd, J=9.7, 5.4 Hz, 1H), 3.69-3.56 (m, 1H), 3.48 (d, J=2.4 Hz, 2H), 2.84-2.63 (m, 2H), 2.45 (s, 3H), 2.21 (t, J=2.4 Hz, 1H); $^{13}$C NMR (126 MHz, CDCl$_3$) δ 172.0, 157.3, 136.0, 129.5, 128.7, 128.4, 126.0, 116.0, 80.5, 73.1, 68.0, 66.6, 58.7, 44.0, 37.8, 34.4; HRMS (ESI/[M+H]$^+$) calcd. for C$_{21}$H$_{23}$ClNO$_3^+$: 372.1361, found [M+H]$^+$: 372.1364; FTIR (neat) ν$_{max}$ 1732, 1491, 1241, 1169, 1034, 824 cm$^{-1}$.

Benzyl 4-(4-chlorophenoxy)-3-(pyrrolidin-1-yl)butanoate (compound 58)

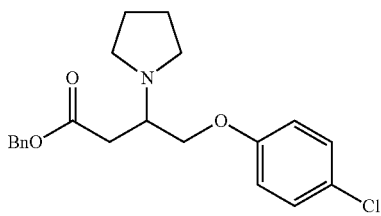 [SMILES: O=C(CC(COc1ccc(Cl)cc1)N1CCCC1)OCc1ccccc1]

Compound 58 was prepared following the general procedure A (see Example 7 supra) (18.0 mg, 48% yield) $^1$H NMR (500 MHz, CDCl$_3$) δ 7.32 (s, 5H), 7.20 (d, J=8.7 Hz, 2H), 6.78 (d, J=8.7 Hz, 2H), 4.91 (s, 2H), 4.09 (dd, J=9.6, 4.5 Hz, 1H), 4.03 (dd, J=9.6, 5.4 Hz, 1H), 3.38-3.26 (m, 1H), 2.76 (d, J=6.5 Hz, 2H), 2.69 (d, J=6.3 Hz, 4H), 1.76 (d, J=5.8 Hz, 4H); $^{13}$C NMR (126 MHz, CDCl$_3$) δ 172.2, 157.4, 136.0, 129.6, 129.4, 128.7, 128.4, 126.0, 117.0, 116.1, 69.1, 66.6, 58.8, 50.9, 35.2, 23.6; HRMS (ESI/[M+H]$^+$) calcd. for C$_{21}$H$_{25}$ClNO$_3^+$: 374.1517, found [M+H]$^+$: 374.1505; FTIR (neat) ν$_{max}$ 1732, 1492, 1242, 1169, 824 cm$^{-1}$.

Benzyl 4-(4-chlorophenoxy)-3-morpholinobutanoate (compound 59)

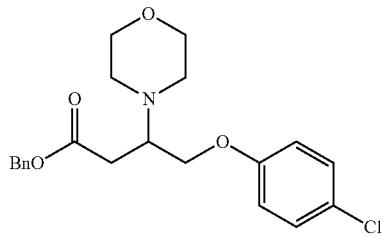 [SMILES: O=C(CC(COc1ccc(Cl)cc1)N1CCOCC1)OCc1ccccc1]

Compound 59 was prepared following the general procedure A (see Example 7 supra) (26.3 mg, 62% yield). $^1$H NMR (500 MHz, CDCl$_3$) δ 7.39-7.30 (m, 5H), 7.24-7.19 (m, 2H), 6.82-6.73 (m, 2H), 5.14 (s, 2H), 4.02 (dd, J=9.6, 5.9 Hz, 1H), 3.94 (dd, J=9.6, 5.2 Hz, 1H), 3.62-3.51 (m, 1H), 2.83 (dt, J=11.4, 5.6 Hz, 2H), 2.71-2.60 (m, 4H), 1.91-1.80 (m, 4H); $^{13}$C NMR (126 MHz, CDCl$_3$) δ 171.8, 157.1, 136.0, 129.5, 128.7, 128.6, 128.5, 126.1, 122.1 (t, J=241.4 Hz), 115.9, 67.6, 66.6, 60.1, 46.2, 34.8, 34.7 (t, J=22.5 Hz); HRMS (ESI/[M+H]$^+$) calcd. for C$_{21}$H$_{23}$ClNO$_3$$^+$: 390.1467, found [M+H]$^+$: 390.1464; FTIR (neat) $v_{max}$ 2853, 1731, 1491, 1455, 1240, 1114, 824 cm$^{-1}$.

Benzyl 3-(azepan-1-yl)-4-(4-chlorophenoxy)butanoate (compound 60)

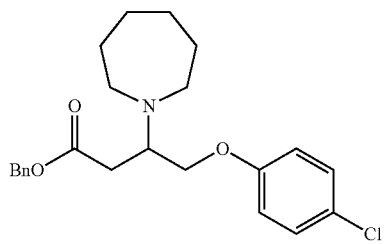 [SMILES: O=C(CC(COc1ccc(Cl)cc1)N1CCCCCC1)OCc1ccccc1]

Compound 60 was prepared following the general procedure A (see Example 7 supra) (21.3 mg, 53% yield). $^1$H NMR (500 MHz, CDCl$_3$) δ 7.40-7.28 (m, 5H), 7.20 (d, J=8.9 Hz, 2H), 6.77 (d, J=8.9 Hz, 2H), 5.13 (s, 2H), 4.11-3.99 (m, 1H), 3.94-3.80 (m, 1H), 3.65-3.51 (m, 1H), 2.87-2.73 (m, 2H), 2.73-2.64 (m, 2H), 2.62 (d, J=7.0 Hz, 2H), 1.53 (d, J=11.7 Hz, 8H); $^{13}$C NMR (126 MHz, CDCl$_3$) δ 172.4, 157.5, 136.1, 129.4, 128.7, 128.5, 128.4, 125.8, 116.0, 68.3, 66.5, 61.6, 51.8, 35.6, 30.1, 27.0; HRMS (ESI/[M+H]$^+$) calcd. for C$_{23}$H$_{29}$ClNO$_3$$^+$: 402.1830, found [M+H]$^+$: 402.1847; FTIR (neat) $v_{max}$ 2855, 1733, 1492, 1242, 1171, 1092, 824 cm$^{-1}$.

tert-Butyl 4-(4-(benzyloxy)-1-(4-chlorophenoxy)-4-oxobutan-2-yl)piperazine-1-carboxylate (compound 61)

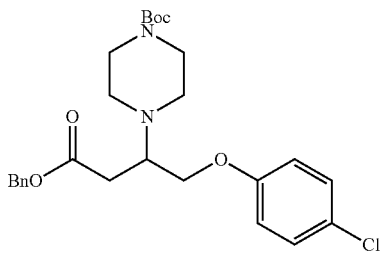 [SMILES: CC(C)(C)OC(=O)N1CCN(C(COc2ccc(Cl)cc2)CC(=O)OCc2ccccc2)CC1]

Compound 61 was prepared following the general procedure A (see Example 7 supra) (32.3 mg, 66% yield). $^1$H NMR (500 MHz, CDCl$_3$) δ 7.36-7.30 (m, 5H), 7.24-7.17 (m, 2H), 6.80-6.72 (m, 2H), 5.17-5.10 (m, 2H), 4.03 (dd, J=9.6, 5.7 Hz, 1H), 3.95 (dd, J=9.6, 5.2 Hz, 1H), 3.54-3.46 (m, 1H), 3.35-3.29 (m, 4H), 2.72-2.61 (m, 4H), 2.56-2.49 (m, 2H), 1.44 (s, 9H); $^{13}$C NMR (126 MHz, CDCl$_3$) δ 171.9, 157.1, 154.8, 135.9, 129.5, 128.7, 128.5, 128.4, 126.1, 115.9, 79.7, 67.5, 66.5, 60.4, 49.3, 34.4, 28.5; HRMS (ESI/[M+H]$^+$) calcd. for C$_{26}$H$_{34}$ClN$_2$O$_5$$^+$: 489.2151, found [M+H]$^+$: 489.2149; FTIR (neat) $v_{max}$ 3015, 1732, 1683, 1492, 1242, 1169, 747 cm$^{-1}$.

Benzyl 4-(4-chlorophenoxy)-3-(4,4-difluoropiperidin-1-yl)butanoate (compound 62)

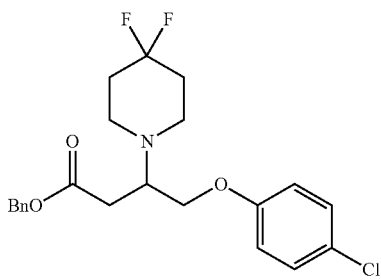 [SMILES: O=C(CC(COc1ccc(Cl)cc1)N1CCC(F)(F)CC1)OCc1ccccc1]

Compound 62 was prepared following the general procedure A (see Example 7 supra) (26.3 mg, 62% yield). $^1$H NMR (500 MHz, CDCl$_3$) δ 7.39-7.30 (m, 5H), 7.24-7.19 (m, 2H), 6.82-6.73 (m, 2H), 5.14 (s, 2H), 4.02 (dd, J=9.6, 5.9 Hz, 1H), 3.94 (dd, J=9.6, 5.2 Hz, 1H), 3.62-3.51 (m, 1H), 2.83 (dt, J=11.4, 5.6 Hz, 2H), 2.71-2.60 (m, 4H), 1.91-1.80 (m, 4H); $^{13}$C NMR (126 MHz, CDCl$_3$) δ 171.8, 157.1, 136.0, 129.5, 128.7, 128.6, 128.5, 126.1, 122.1 (t, J=241.4 Hz), 115.9, 67.6, 66.6, 60.1, 46.2, 34.8, 34.7 (t, J=22.5 Hz); $^{19}$F NMR (471 MHz, CDCl$_3$) δ -97.62 (s); HRMS (ESI/[M+H]$^+$) calcd. for C$_{22}$H$_{25}$ClF$_2$NO$_3$$^+$: 424.1486, found [M+H]$^+$: 424.1473; FTIR (neat) $v_{max}$ 2854, 1732, 1492, 1242, 1094, 825 cm$^{-1}$.

Methyl 1-(4-(benzyloxy)-1-(4-chlorophenoxy)-4-oxobutan-2-yl)piperidine-4-carboxylate (compound 63)

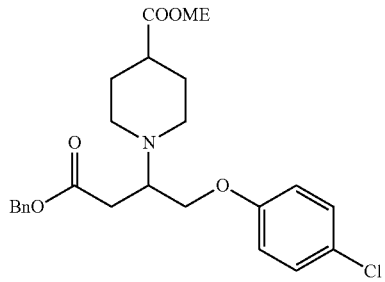

Compound 63 was prepared following the general procedure A (see Example 7 supra) (33.0 mg, 74% yield). $^1$H NMR (500 MHz, CDCl$_3$) δ 7.33 (dt, J=6.2, 3.9 Hz, 5H), 7.25-7.16 (m, 2H), 6.81-6.72 (m, 2H), 5.13 (s, 2H), 4.04 (dd, J=9.4, 5.7 Hz, 1H), 3.93 (dd, J=9.3, 5.6 Hz, 1H), 3.67 (s, 3H), 3.50 (dd, J=11.9, 5.8 Hz, 1H), 2.93 (d, J=10.9 Hz, 1H), 2.84 (d, J=10.9 Hz, 1H), 2.72-2.58 (m, 2H), 2.53 (t, J=10.3 Hz, 1H), 2.31 (t, J=10.4 Hz, 1H), 2.27-2.18 (m, 1H), 1.84 (d, J=12.3 Hz, 2H), 1.70-1.57 (m, 2H); $^{13}$C NMR (126 MHz, CDCl$_3$) δ 175.6, 172.1, 157.2, 136.0, 129.5, 128.7, 128.5, 128.4, 126.0, 115.9, 67.8, 66.5, 60.5, 51.7, 50.4, 48.0, 41.4, 34.4, 29.0, 28.9; HRMS (ESI/[M+H]$^+$) calcd. for C$_{24}$H$_{29}$ClNO$_5$$^+$: 446.1729, found [M+H]$^+$: 446.1730; FTIR (neat) $v_{max}$ 2859, 1733, 1492, 1243, 904 cm$^{-1}$.

Benzyl 4-(4-chlorophenoxy)-3-(4-phenylpiperidin-1-yl)butanoate (compound 64)

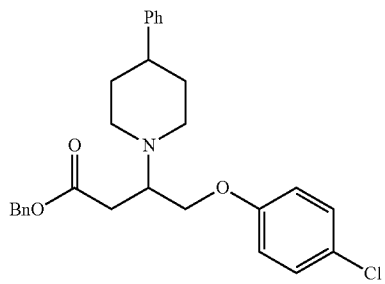 [SMILES: O=C(CC(COc1ccc(Cl)cc1)N1CCC(c2ccccc2)CC1)OCc1ccccc1]

Compound 64 was prepared following the general procedure A (see Example 7 supra) (32.9 mg, 71% yield). $^1$H NMR (500 MHz, CDCl$_3$) δ 7.39-7.29 (m, 7H), 7.25-7.19 (m, 5H), 6.84-6.78 (m, 2H), 5.20-5.14 (m, 2H), 4.12 (dd, J=9.5, 5.5 Hz, 1H), 4.00 (dd, J=9.5, 5.7 Hz, 1H), 3.61-3.52 (m, 1H), 3.04 (d, J=11.1 Hz, 1H), 2.97 (d, J=11.2 Hz, 1H), 2.78-2.60 (m, 3H), 2.48-2.41 (m, 2H), 1.81 (d, J=12.3 Hz, 2H), 1.72-1.62 (m, 2H); $^{13}$C NMR (126 MHz, CDCl$_3$) δ 172.3, 157.3, 146.4, 136.1, 129.4, 128.7, 128.49, 128.45, 128.4, 127.0, 126.2, 125.9, 116.0, 67.9, 66.5, 60.6, 51.7, 49.2, 43.0, 34.4, 34.2, 34.0; HRMS (ESI/[M+H]$^+$) calcd. for C$_{28}$H$_{31}$ClNO$_3$$^+$: 464.1987, found [M+H]$^+$: 464.1999; FTIR (neat) $v_{max}$ 3030, 1731, 1491, 1240, 731, 697 cm$^{-1}$.

Benzyl 4-phenoxy-3-(piperidin-1-yl)butanoate (compound 65)

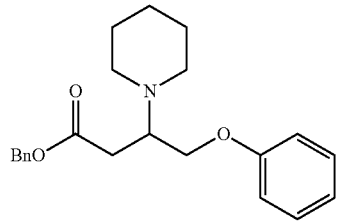 [SMILES: O=C(CC(COc1ccccc1)N1CCCCC1)OCc1ccccc1]

Compound 65 was prepared following the general procedure A (see Example 7 supra) (21.2 mg, 60% yield). $^1$H NMR (500 MHz, CDCl$_3$) δ 7.39-7.30 (m, 5H), 7.30-7.25 (m, 2H), 6.98-6.92 (m, 1H), 6.87 (dd, J=8.7, 0.9 Hz, 2H), 5.14 (s, 2H), 4.12 (dd, J=9.5, 5.3 Hz, 1H), 3.98 (dd, J=9.5, 6.0 Hz, 1H), 3.58-3.40 (m, 1H), 2.76-2.62 (m, 4H), 2.62-2.49 (m, 2H), 1.59-1.47 (m, 4H), 1.41 (dd, J=11.7, 5.8 Hz, 2H); $^{13}$C NMR (126 MHz, CDCl$_3$) δ 172.5, 158.7, 136.2, 129.5, 128.6, 128.3, 128.2, 120.9, 114.7, 67.4, 66.4, 61.0, 50.7, 34.4, 26.7, 24.8; HRMS (ESI/[M+H]$^+$) calcd. for C$_{22}$H$_{28}$NO$_4$$^+$: 354.2064, found [M+H]$^+$: 354.2046; FTIR (neat) $v_{max}$ 2931, 1731, 1599, 1497, 1240, 1152, 750, 691 cm$^{-1}$.

Benzyl 4-(4-fluorophenoxy)-3-(piperidin-1-yl)butanoate (compound 66)

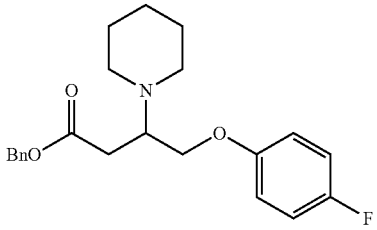 [SMILES: O=C(CC(COc1ccc(F)cc1)N1CCCCC1)OCc1ccccc1]

Compound 66 was prepared following the general procedure A (see Example 7 supra) (24.1 mg, 65% yield). $^1$H NMR (500 MHz, CDCl$_3$) δ 7.38-7.30 (m, 5H), 7.01-6.87 (m, 2H), 6.83-6.72 (m, 2H), 5.17-5.10 (m, 2H), 4.06 (dd, J=9.4, 5.3 Hz, 1H), 3.93 (dd, J=9.4, 6.0 Hz, 1H), 3.51-3.41 (m, 1H), 2.75-2.60 (m, 4H), 2.53 (dt, J=10.7, 5.1 Hz, 2H), 1.54-1.48 (m, 4H), 1.45-1.36 (m, 2H); $^{13}$C NMR (126 MHz, CDCl$_3$) δ 172.5, 157.4 (d, J=238.4 Hz), 154.9, 136.1, 128.6, 128.4, 128.3, 115.9 (d, J=23.0 Hz), 115.7 (d, J=7.9 Hz), 68.3, 66.4, 61.0, 50.7, 34.2, 26.7, 24.8; $^{19}$F NMR (471 MHz, CDCl$_3$) δ −125.08 (s); HRMS (ESI/[M+H]$^+$) calcd. for C$_{22}$H$_{27}$FNO$_3$$^+$: 372.1969, found [M+H]$^+$: 372.1971; FTIR (neat) $v_{max}$ 3034, 2855, 1734, 1506, 1011, 828 cm$^{-1}$.

Benzyl 4-(4-chlorophenoxy)-3-(piperidin-1-yl)butanoate (compound 67)

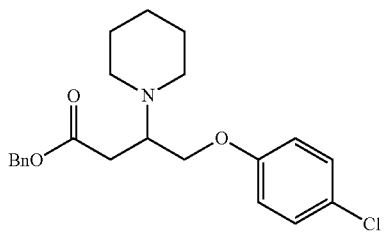

Compound 67 was prepared following the general procedure A (see Example 7 supra) (26.8 mg, 69% yield). $^1$H NMR (500 MHz, CDCl$_3$) δ 7.39-7.29 (m, 5H), 7.24-7.17 (m, 2H), 6.82-6.73 (m, 2H), 5.16-5.10 (m, 2H), 4.07 (dd, J=9.4, 5.4 Hz, 1H), 3.94 (dd, J=9.5, 6.0 Hz, 1H), 3.55-3.38 (m, 1H), 3.55-3.38 (m, 1H), 2.74-2.59 (m, 4H), 2.56-2.50 (m, 2H), 1.54-1.47 (m, 4H), 1.45-1.36 (m, 2H); $^{13}$C NMR (126 MHz, CDCl$_3$) δ 172.4, 157.4, 136.1, 129.4, 128.6, 128.4, 128.3, 125.8, 115.9, 67.9, 66.4, 60.9, 50.7, 34.2, 26.7, 24.8; $^{19}$F NMR (471 MHz, CDCl$_3$) δ −125.08; HRMS (ESI/[M+H]$^+$) calcd. for C$_{22}$H$_{27}$ClNO$_3$$^+$: 388.1674, found [M+H]$^+$: 388.1680; FTIR (neat) ν$_{max}$ 2932, 1734, 1492, 1242, 1170, 824 cm$^{-1}$.

Benzyl 4-(4-bromophenoxy)-3-(piperidin-1-yl)butanoate (compound 68)

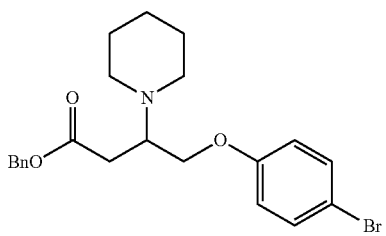 [SMILES: O=C(CC(COc1ccc(Br)cc1)N1CCCCC1)OCc1ccccc1]

Compound 68 was prepared following the general procedure A (see Example 7 supra) (27.6 mg, 64% yield). $^1$H NMR (500 MHz, CDCl$_3$) δ 7.46-7.27 (m, 7H), 6.78-6.67 (m, 2H), 5.16-5.10 (m, 2H), 4.07 (dd, J=9.5, 5.4 Hz, 1H), 3.94 (dd, J=9.5, 6.0 Hz, 1H), 3.56-3.36 (m, 1H), 3.55-3.38 (m, 1H), 2.74-2.59 (m, 4H), 2.52 (dt, J=10.6, 5.2 Hz, 2H), 1.55-1.48 (m, 4H), 1.45-1.36 (m, 2H); $^{13}$C NMR (126 MHz, CDCl$_3$) δ 172.4, 157.8, 136.1, 132.3, 128.6, 128.4, 128.3, 116.5, 113.1, 67.9, 66.4, 60.9, 50.7, 34.2, 26.7, 24.8; HRMS (ESI/[M+H]$^+$) calcd. for C$_{22}$H$_{27}$BrNO$_3$$^+$: 432.1169/434.1148, found [M+H]$^+$: 432.1185/434.1152; FTIR (neat) ν$_{max}$ 2931, 1734, 1489, 1242, 1171, 822 cm$^{-1}$.

Benzyl 4-(4-iodophenoxy)-3-(piperidin-1-yl)butanoate (compound 69)

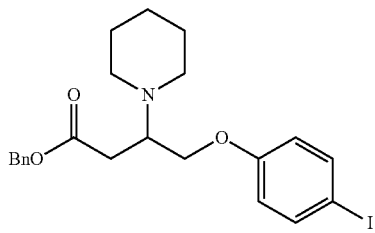

Compound 69 was prepared following the general procedure A (see Example 7 supra) (32.6 mg, 68% yield). $^1$H NMR (500 MHz, CDCl$_3$) δ 7.58-7.48 (m, 2H), 7.38-7.29 (m, 5H), 6.67-6.58 (m, 2H), 5.16-5.10 (m, 2H), 4.06 (dd, J=9.5, 5.4 Hz, 1H), 3.93 (dd, J=9.5, 6.0 Hz, 1H), 3.53-3.39 (m, 1H), 2.73-2.59 (m, 4H), 2.55-2.49 (m, 2H), 1.54-1.47 (m, 4H), 1.46-1.37 (m, 2H); $^{13}$C NMR (126 MHz, CDCl$_3$) δ 172.3, 158.6, 138.3, 136.1, 128.6, 128.4, 128.3, 117.1, 83.0, 67.7, 66.4, 60.8, 50.7, 34.2, 26.7, 24.8; HRMS (ESI/[M+H]$^+$) calcd. for C$_{22}$H$_{27}$INO$_3$$^+$: 384.1030, found [M+H]$^+$: 384.1020; FTIR (neat) ν$_{max}$ 2932, 1731, 1485, 1240, 1172, 907, 730 cm$^{-1}$.

Benzyl 4-(4-cyanophenoxy)-3-(piperidin-1-yl)butanoate (compound 70)

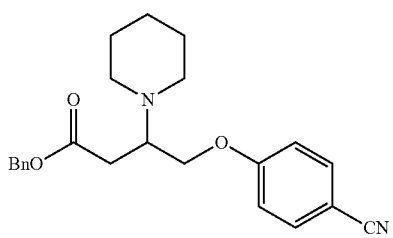 [SMILES: N#Cc1ccc(OCC(CC(=O)OCc2ccccc2)N2CCCCC2)cc1]

Compound 70 was prepared following the general procedure A (see Example 7 supra) (27.6 mg, 73% yield). $^1$H NMR (500 MHz, CDCl$_3$) δ 7.57-7.53 (m, 2H), 7.35-7.29 (m, 5H), 6.90-6.85 (m, 2H), 5.20-5.02 (m, 2H), 4.15 (dd, J=9.6, 5.5 Hz, 1H), 4.02 (dd, J=9.5, 5.9 Hz, 1H), 3.55-3.40 (m, 1H), 2.78-2.59 (m, 4H), 2.57-2.47 (m, 2H), 1.57-1.44 (m, 4H), 1.45-1.35 (m, 2H); $^{13}$C NMR (126 MHz, CDCl$_3$) δ 172.2, 161.9, 136.0, 134.1, 128.7, 128.4, 127.1, 119.3, 115.4, 104.3, 68.0, 66.5, 60.6, 50.7, 34.0, 26.6, 24.7; HRMS (ESI/[M+H]$^+$) calcd. for C$_{23}$H$_{27}$N$_2$O$_3$$^+$: 379.2016, found [M+H]$^+$: 379.2021; FTIR (neat) ν$_{max}$ 3020, 1730, 1606, 1508, 1256, 1215, 749 cm$^{-1}$.

Benzyl 4-(4-nitrophenoxy)-3-(piperidin-1-yl)butanoate (compound 71)

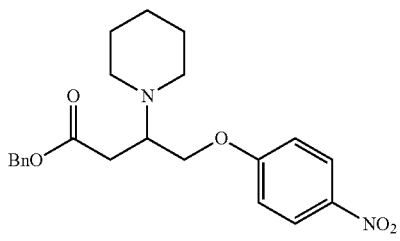

Compound 71 was prepared following the general procedure A (see Example 7 supra) (33.8 mg, 85% yield). $^1$H NMR (500 MHz, CDCl$_3$) δ 8.26-7.98 (m, 2H), 7.36-7.28 (m, 5H), 7.01-6.70 (m, 2H), 5.24-5.02 (m, 2H), 4.19 (dd, J=9.6, 5.5 Hz, 1H), 4.07 (dd, J=9.6, 5.9 Hz, 1H), 3.57-3.42 (m, 1H), 2.77-2.59 (m, 4H), 2.53 (dt, J=10.7, 5.2 Hz, 2H), 1.51 (dt, J=10.7, 5.2 Hz, 4H), 1.45-1.38 (m, 2H); $^{13}$C NMR (126 MHz, CDCl$_3$) δ 172.1, 163.7, 141.7, 136.0, 128.7, 128.4, 126.0, 114.6, 68.5, 66.5, 60.6, 50.7, 34.0, 26.6, 24.7; HRMS (ESI/[M+H]$^+$) calcd. for C$_{22}$H$_{27}$N$_2$O$_5$$^+$: 399.1914, found [M+H]$^+$: 399.1912; FTIR (neat) ν$_{max}$ 3030, 1730, 1592, 1513, 1341, 1258, 1171, 750, 731 cm$^{-1}$.

Benzyl 3-(piperidin-1-yl)-4-(4-(trifluoromethyl)phenoxy)butanoate (compound 72)

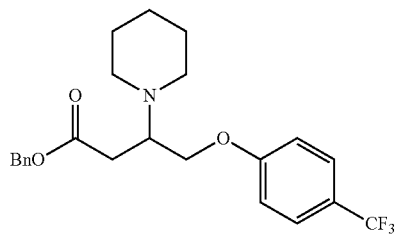 [SMILES: O=C(CC(COc1ccc(C(F)(F)F)cc1)N1CCCCC1)OCc1ccccc1]

Compound 72 was prepared following the general procedure A (see Example 7 supra) (24.4 mg, 58% yield). $^1$H NMR (500 MHz, CDCl$_3$) δ 7.52 (d, J=8.6 Hz, 2H), 7.39-7.29 (m, 5H), 6.90 (d, J=8.6 Hz, 2H), 5.21-5.04 (m, 2H), 4.14 (dd, J=9.5, 5.4 Hz, 1H), 4.02 (dd, J=9.5, 5.9 Hz, 1H), 3.56-3.43 (m, 1H), 2.77-2.61 (m, 4H), 2.53 (dt, J=10.6, 5.2 Hz, 2H), 1.60-1.45 (m, 4H), 1.44-1.36 (m, 2H); $^{13}$C NMR (126 MHz, CDCl$_3$) δ 172.3, 161.1, 136.1, 128.6, 128.4, 128.3, 127.0 (q, J=3.3 Hz), 124.55 (q, J=270.6 Hz), 123.14 (q, J=32.5 Hz), 114.6, 67.9, 66.5, 60.8, 50.7, 34.2, 26.7, 24.8; $^{19}$F NMR (471 MHz, CDCl$_3$) δ −61.49 (s); HRMS (ESI/[M+H]$^+$) calcd. for C$_{23}$H$_{27}$F$_3$NO$_3$$^+$: 422.1938, found [M+H]$^+$: 422.1937; FTIR (neat) ν$_{max}$ 2933, 1731, 1615, 1325, 1254, 1158, 1109, 731 cm$^{-1}$.

Benzyl 4-(4-methoxyphenoxy)-3-(piperidin-1-yl)butanoate (compound 73)

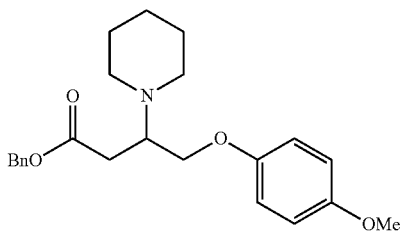 [SMILES: COc1ccc(OCC(CC(=O)OCc2ccccc2)N2CCCCC2)cc1]

Compound 73 was prepared following the general procedure A (see Example 7 supra) (21.8 mg, 57% yield). $^1$H NMR (500 MHz, CDCl$_3$) δ 7.39-7.28 (m, 5H), 6.85-6.75 (m, 4H), 5.14 (s, 2H), 4.07 (dd, J=9.5, 5.3 Hz, 1H), 3.93 (dd, J=9.4, 6.1 Hz, 1H), 3.76 (s, 3H), 3.56-3.41 (m, 1H), 2.76-2.61 (m, 4H), 2.61-2.47 (m, 2H), 1.52 (s, 4H), 1.44-1.38 (m, 2H); $^{13}$C NMR (126 MHz, CDCl$_3$) δ 172.5, 154.0, 152.9, 136.2, 128.6, 128.3, 128.2, 115.6, 114.7, 68.2, 66.4, 61.1, 55.9, 50.7, 34.3, 26.6, 24.8; HRMS (ESI/[M+H]$^+$) calcd. for C$_{23}$H$_{30}$NO$_4$$^+$: 354.2169, found [M+H]$^+$: 354.2179; FTIR (neat) ν$_{max}$ 2931, 1732, 1507, 1229, 824, 749 cm$^{-1}$.

Benzyl 4-(2-allylphenoxy)-3-(piperidin-1-yl)butanoate (compound 74)

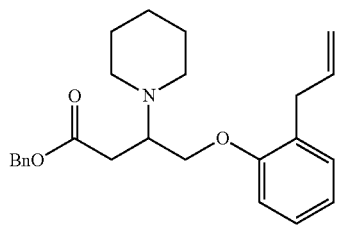 [SMILES: C=CCc1ccccc1OCC(CC(=O)OCc1ccccc1)N1CCCCC1]

Compound 74 was prepared following the general procedure A (see Example 7 supra) (26.4 mg, 67% yield). $^1$H NMR (500 MHz, CDCl$_3$) δ 7.36-7.30 (m, 5H), 7.21-7.11 (m, 2H), 6.91 (t, J=7.4 Hz, 1H), 6.82 (d, J=7.8 Hz, 1H), 6.04-5.91 (m, 1H), 5.14 (s, 2H), 5.08-5.01 (m, 2H), 4.10 (dd, J=9.5, 5.3 Hz, 1H), 4.02 (dd, J=9.5, 5.2 Hz, 1H), 3.51 (td, J=7.2, 3.6 Hz, 1H), 3.38 (d, J=6.6 Hz, 2H), 2.76-2.65 (m, 4H), 2.59-2.51 (m, 2H), 1.58-1.47 (m, 4H), 1.46-1.36 (m, 2H); $^{13}$C NMR (126 MHz, CDCl$_3$) δ 172.4, 156.3, 137.1, 136.2, 129.9, 128.8, 128.6, 128.3, 128.2, 127.4, 120.8, 115.6, 111.0, 67.1, 66.4, 61.1, 50.7, 34.5, 26.7, 24.8; HRMS (ESI/[M+H]$^+$) calcd. for C$_{25}$H$_{32}$NO$_4$$^+$: 394.2377, found [M+H]$^+$: 394.2372; FTIR (neat) ν$_{max}$ 2930, 1732, 1493, 1239, 1153, 1122749 cm$^{-1}$.

Benzyl 4-(4-(2-hydroxyethyl)phenoxy)-3-(piperidin-1-yl)butanoate (compound 75)

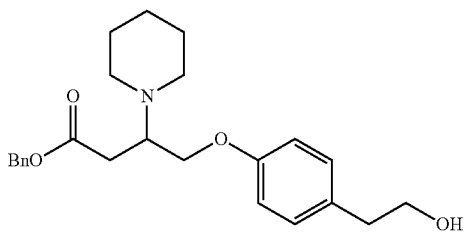 [SMILES: O=C(CC(COc1ccc(CCO)cc1)N1CCCCC1)OCc1ccccc1]

Compound 75 was prepared following the general procedure A (see Example 7 supra) (25.9 mg, 65% yield). $^1$H NMR (500 MHz, CDCl$_3$) δ 7.51-7.28 (m, 5H), 7.24-6.99 (m, 2H), 6.87-6.60 (m, 2H), 5.13 (s, 2H), 4.09 (dd, J=9.5, 5.3 Hz, 1H), 3.95 (dd, J=9.5, 6.0 Hz, 1H), 3.81 (t, J=6.6 Hz, 2H), 3.60-3.40 (m, 1H), 2.80 (t, J=6.6 Hz, 2H), 2.75-2.59 (m, 4H), 2.53 (dt, J=11.0, 5.3 Hz, 2H), 1.62-1.46 (m, 4H), 1.40 (dd, J=11.3, 5.7 Hz, 2H); $^{13}$C NMR (126 MHz, CDCl$_3$) δ 172.5, 157.5, 136.2, 130.8, 130.1, 128.7, 128.4, 128.3, 114.8, 67.6, 66.4, 64.0, 61.0, 50.7, 38.4, 34.4, 26.7, 24.8; HRMS (ESI/[M+H]$^+$) calcd. for C$_{24}$H$_{32}$NO$_4^+$: 398.2326, found [M+H]$^+$: 398.2316; FTIR (neat) ν$_{max}$ 2930, 1729, 1611, 1511, 1239, 1172, 1044, 826 cm$^{-1}$.

Benzyl 4-((2-oxo-2H-chromen-7-yl)oxy)-3-(piperidin-1-yl)butanoate (compound 76)

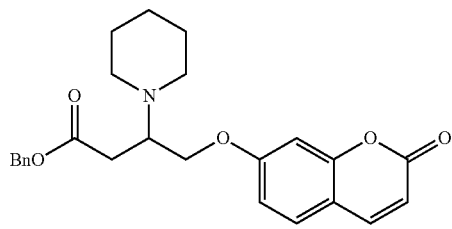 [SMILES: O=C(CC(COc1ccc2ccc(=O)oc2c1)N1CCCCC1)OCc1ccccc1]

Compound 76 was prepared following the general procedure A (see Example 7 supra) (24.8 mg, 59% yield). $^1$H NMR (500 MHz, CDCl$_3$) δ 7.62 (d, J=9.5 Hz, 1H), 7.40-7.27 (m, 6H), 6.80-6.75 (m, 2H), 6.25 (d, J=9.5 Hz, 1H), 5.17-5.09 (m, 2H), 4.16 (dd, J=9.6, 5.4 Hz, 1H), 4.03 (dd, J=9.6, 5.9 Hz, 1H), 3.55-3.44 (m, 1H), 2.75-2.59 (m, 4H), 2.53 (dt, J=10.6, 5.1 Hz, 2H), 1.56-1.46 (m, 4H), 1.47-1.37 (m, 2H); $^{13}$C NMR (126 MHz, CDCl$_3$) δ 172.2, 161.9, 161.3, 155.9, 143.5, 136.0, 128.8, 128.6, 128.4, 128.3, 113.3, 113.0, 112.8, 101.7, 68.2, 66.5, 60.7, 50.7, 34.1, 26.7, 24.7; HRMS (ESI/[M+H]$^+$) calcd. for C$_{25}$H$_{28}$NO$_5^+$: 422.1962, found [M+H]$^+$: 422.1961; FTIR (neat) ν$_{max}$ 2854, 1726, 1612, 1155, 1121, 727 cm$^{-1}$.

Benzyl 4-(2,6-diisopropylphenoxy)-3-(piperidin-1-yl)butanoate (compound 77)

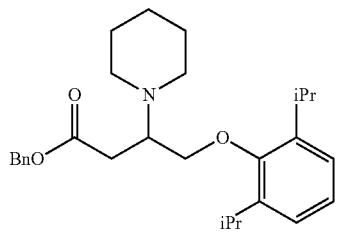 [SMILES: CC(C)c1cccc(C(C)C)c1OCC(CC(=O)OCc1ccccc1)N1CCCCC1]

Compound 77 was prepared following the general procedure A (see Example 7 supra) (23.2 mg, 53% yield). iPR=isopropyl group. $^1$H NMR (500 MHz, CDCl$_3$) δ 7.43-7.29 (m, 5H), 7.18-7.01 (m, 3H), 5.17 (s, 2H), 3.87 (dd, J=9.4, 5.8 Hz, 1H), 3.71 (dd, J=9.1, 6.7 Hz, 1H), 3.58-3.50 (m, 1H), 3.36-3.24 (m, 2H), 2.73 (d, J=6.9 Hz, 2H), 2.67 (dt, J=10.4, 5.1 Hz, 2H), 2.63-2.57 (m, 2H), 1.53 (dt, J=10.9, 5.4 Hz, 4H), 1.45-1.36 (m, 2H), 1.22 (dd, J=6.9, 4.0 Hz, 12H); $^{13}$C NMR (126 MHz, CDCl$_3$) δ 172.6, 153.2, 141.8, 136.2, 128.6, 128.33, 128.27, 124.7, 124.1, 73.9, 66.4, 62.0, 50.6, 34.0, 26.7, 26.5, 25.0, 24.2; HRMS (ESI/[M+H]$^+$) calcd. for C$_{28}$H$_{40}$NO$_3^+$: 438.3003, found [M+H]$^+$: 438.2990; FTIR (neat) ν$_{max}$ 2962, 2930, 1736, 1256, 1153 cm$^{-1}$.

Benzyl 4-(2,6-diisopropylphenoxy)-3-(piperidin-1-yl)butanoate-3-d (compound 78)

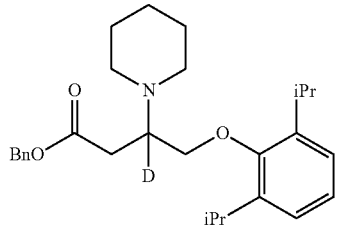 [SMILES: [2H]C(COc1c(C(C)C)cccc1C(C)C)(CC(=O)OCc1ccccc1)N1CCCCC1]

Compound 78 was prepared following the general procedure A (see Example 7 supra) (37.7 mg, 86% yield). $^1$H NMR (500 MHz, CDCl$_3$) δ 7.40-7.32 (m, 5H), 7.11-7.06 (m, 3H), 5.16 (s, 2H), 3.86 (d, J=9.4 Hz, 1H), 3.70 (d, J=9.4 Hz, 1H), 3.33-3.25 (m, 2H), 2.72 (s, 2H), 2.66 (q, J=5.3 Hz, 2H), 2.60 (q, J=5.1 Hz, 2H), 1.56-1.49 (m, 4H), 1.43-1.39 (m, 2H), 1.21 (dd, J=6.9, 4.1 Hz, 12H); $^{13}$C NMR (126 MHz, CDCl$_3$) δ 172.6, 153.2, 141.8, 136.2, 128.6, 128.34, 128.28, 124.7, 124.1, 73.8, 66.4, 50.6, 33.9, 26.7, 26.5, 25.0, 24.23, 24.19; HRMS (ESI/[M+H]$^+$) calcd. for C$_{28}$H$_{39}$DNO$_3^+$: 439.3065, found [M+H]$^+$: 439.3063; FTIR (neat) ν$_{max}$ 2931, 1734, 1442, 1324, 1251, 1183, 1051 cm$^{-1}$.

Benzyl 4-((2-methylbenzo[d]oxazol-6-yl)oxy)-3-(piperidin-1-yl)butanoate (compound 79)

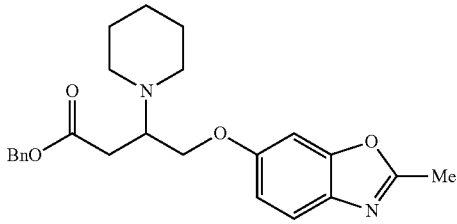 [SMILES: Cc1nc2ccc(OCC(CC(=O)OCc3ccccc3)N3CCCCC3)cc2o1]

Compound 79 was prepared following the general procedure A (see Example 7 supra) (18.4 mg, 45% yield). $^1$H NMR (500 MHz, CDCl$_3$) δ 7.47 (d, J=8.7 Hz, 1H), 7.45-7.28 (m, 5H), 6.96 (d, J=2.3 Hz, 1H), 6.83 (dd, J=8.7, 2.4 Hz, 1H), 5.31-4.97 (m, 2H), 4.13 (dd, J=9.4, 5.3 Hz, 1H), 4.00 (dd, J=9.4, 6.0 Hz, 1H), 3.64-3.39 (m, 1H), 2.89-2.64 (m, 4H), 2.59 (s, 3H), 2.54 (dt, J=10.9, 5.3 Hz, 2H), 1.60-1.47 (m, 4H), 1.43-1.31 (m, 2H); $^{13}$C NMR (126 MHz, CDCl$_3$) δ 172.5, 163.0, 156.8, 151.8, 136.1, 135.5, 128.7, 128.4, 128.3, 119.4, 112.7, 96.4, 68.5, 66.5, 61.0, 50.8, 50.1, 34.3, 26.7, 24.8, 14.6; HRMS (ESI/[M+H]$^+$) calcd. for C$_{24}$H$_{29}$N$_2$O$_4$$^+$: 409.2122, found [M+H]$^+$: 409.2120; FTIR (neat) $v_{max}$ 2931, 1732, 1618, 1455, 1295, 1142, 1028 cm$^{-1}$.

Benzyl 4-(3,5-bis(trifluoromethyl)phenoxy)-3-(piperidin-1-yl)butanoate (compound 80)

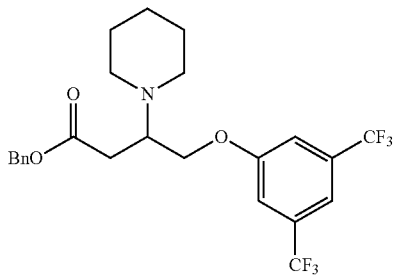

Compound 80 was prepared following the general procedure A (see Example 7 supra) (38.1 mg, 78% yield). $^1$H NMR (500 MHz, CDCl$_3$) δ 7.46 (s, 1H), 7.36-7.30 (m, 5H), 7.27 (s, 2H), 5.14 (s, 2H), 4.17 (dd, J=9.3, 5.5 Hz, 1H), 4.06 (dd, J=9.3, 5.6 Hz, 1H), 3.55-3.45 (m, 1H), 2.78-2.60 (m, 4H), 2.59-2.51 (m, 2H), 1.56-1.49 (m, 4H), 1.46-1.36 (m, 2H); $^{13}$C NMR (126 MHz, CDCl$_3$) δ 172.1, 159.3, 136.0, 132.9 (q, J=33.3 Hz), 128.7, 128.4, 123.3 (q, J=273.1 Hz), 115.0, 114.6, 68.5, 66.6, 60.8, 50.8, 33.9, 26.6, 24.7; $^{19}$F NMR (471 MHz, CDCl$_3$) δ −62.98 (s); HRMS (ESI/[M+H]$^+$) calcd. for C$_{24}$H$_{26}$F$_6$NO$_3$$^+$: 490.1811, found [M+H]$^+$: 490.1824; FTIR (neat) $v_{max}$ 3035, 1734, 1463, 1370, 1277, 1173, 1133 cm$^{-1}$.

Benzyl 4-(perfluorophenoxy)-3-(piperidin-1-yl)butanoate (compound 81)

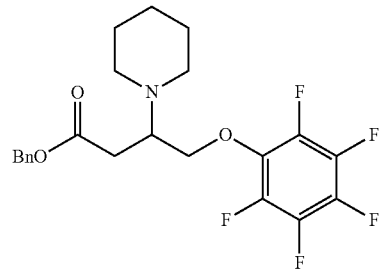 [SMILES: O=C(CC(COc1c(F)c(F)c(F)c(F)c1F)N1CCCCC1)OCc1ccccc1]

Compound 81 was prepared following the general procedure A (see Example 7 supra) (34.1 mg, 77% yield). $^1$H NMR (500 MHz, CDCl$_3$) δ 7.47-7.27 (m, 5H), 5.20-5.05 (m, 2H), 4.25 (dd, J=10.0, 6.2 Hz, 1H), 4.17 (dd, J=10.0, 5.1 Hz, 1H), 3.56-3.36 (m, 1H), 2.69 (dd, J=15.1, 6.8 Hz, 1H), 2.65-2.38 (m, 5H), 1.56-1.30 (m, 6H); $^{13}$C NMR (126 MHz, CDCl$_3$) δ 172.1, 142.8, 140.8, 139.0, 138.4, 137.0, 136.0, 133.9, 128.6, 128.5, 128.4, 74.4, 66.6, 61.7, 50.4, 32.9, 26.6, 24.7; $^{19}$F NMR (471 MHz, CDCl$_3$) δ −157.60--157.73 (m), −164.65--164.82 (m), −164.89 (d, J=21.0 Hz); HRMS (ESI/[M+H]$^+$) calcd. for C$_{22}$H$_{23}$F$_5$NO$_4$$^+$: 444.1593, found [M+H]$^+$: 444.1619; FTIR (neat) $v_{max}$ 2856, 1732, 1511, 1216, 1154, 992, 751 cm$^{-1}$.

Benzyl 4-(4-morpholinophenoxy)-3-(piperidin-1-yl)butanoate (compound 82)

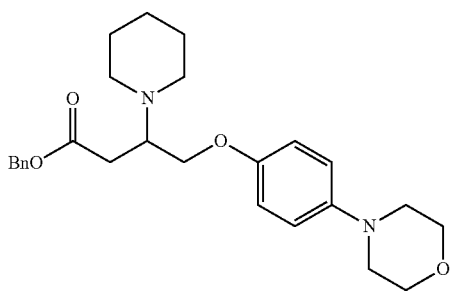 [SMILES: O=C(CC(COc1ccc(N2CCOCC2)cc1)N1CCCCC1)OCc1ccccc1]

Compound 82 was prepared following the general procedure A (see Example 7 supra) (23.7 mg, 54% yield). $^1$H NMR (500 MHz, CDCl$_3$) δ 7.41-7.27 (m, 5H), 6.89-6.78 (m, 4H), 5.13 (s, 2H), 4.14-4.06 (m, 1H), 3.93 (dd, J=9.5, 6.1 Hz, 1H), 3.88-3.83 (m, 4H), 3.45 (dq, J=14.6, 7.2 Hz, 1H), 3.08-3.02 (m, 4H), 2.72-2.61 (m, 4H), 2.53 (dt, J=10.3, 5.1 Hz, 2H), 1.51 (s, 4H), 1.48-1.37 (m, 2H); $^{13}$C NMR (126 MHz, CDCl$_3$) δ 172.5, 153.1, 145.9, 136.2, 128.6, 128.3, 128.2, 117.9, 115.4, 68.0, 67.2, 66.4, 61.1, 50.9, 50.7, 34.3, 26.7, 24.8; HRMS (ESI/[M+H]$^+$) calcd. for C$_{26}$H$_{35}$N$_2$O$_4$$^+$: 439.2591, found [M+H]$^+$: 439.2581; FTIR (neat) $v_{max}$ 2854, 1734, 1510, 1231, 1121 cm$^{-1}$.

Benzyl 4-(4-(phenylsulfonyl)phenoxy)-3-(piperidin-1-yl)butanoate (compound 83)

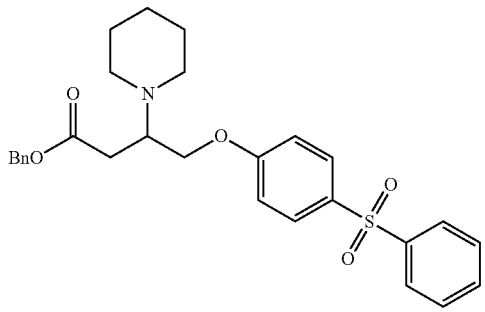 [SMILES: O=C(CC(COc1ccc(S(=O)(=O)c2ccccc2)cc1)N1CCCCC1)OCc1ccccc1]

Compound 83 was prepared following the general procedure A (see Example 7 supra) (30.1 mg, 61% yield). $^1$H NMR (500 MHz, CDCl$_3$) δ 7.91 (dt, J=3.5, 2.3 Hz, 2H), 7.87-7.82 (m, 2H), 7.56-7.51 (m, 1H), 7.51-7.45 (m, 2H), 7.35-7.26 (m, 5H), 6.93-6.86 (m, 2H), 5.14-5.08 (m, 2H), 4.12 (dd, J=9.6, 5.5 Hz, 1H), 4.00 (dd, J=9.6, 5.8 Hz, 1H), 3.49-3.42 (m, 1H), 2.72-2.58 (m, 4H), 2.50 (dt, J=10.6, 5.2 Hz, 2H), 1.48 (dd, J=11.0, 5.6 Hz, 4H), 1.41-1.35 (m, 2H); $^{13}$C NMR (126 MHz, CDCl$_3$) δ 172.2, 162.5, 142.4, 136.0, 133.4, 132.96, 129.95, 129.3, 128.6, 128.4, 128.3, 127.4, 115.1, 68.1, 66.5, 60.7, 50.7, 34.0, 26.6, 24.7; HRMS (ESI/[M+H]$^+$) calcd. for C$_{28}$H$_{32}$NO$_5$S$^+$: 494.1996, found [M+H]$^+$: 494.1993; FTIR (neat) $v_{max}$ 2930, 1731, 1592, 1496, 1301, 1257, 1151, 732 cm$^{-1}$.

Benzyl 4-(4-((S)-2-((tert-butoxycarbonyl)amino)-3-methoxy-3-oxopropyl)phenoxy)-3-(piperidin-1-yl)butanoate (compound 84)

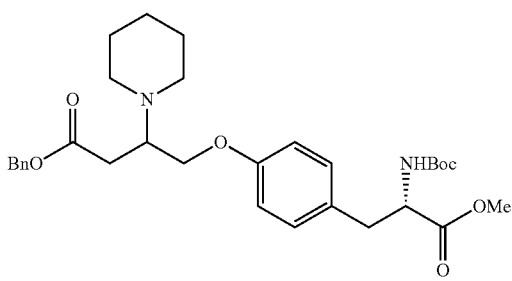 [SMILES: COC(=O)[C@H](Cc1ccc(OCC(CC(=O)OCc2ccccc2)N2CCCCC2)cc1)NC(=O)OC(C)(C)C]

Compound 84 was prepared following the general procedure B (see Example 7 supra) (29.4 mg, 53% yield, dr 1:1). $^1$H NMR (500 MHz, CDCl$_3$) δ 7.58-7.26 (m, 5H), 7.00 (d, J=8.5 Hz, 2H), 6.81-6.43 (m, 2H), 5.13 (s, 2H), 4.96 (d, J=8.3 Hz, 1H), 4.53 (d, J=7.9 Hz, 1H), 3.94 (ddd, J=9.5, 6.0, 1.2 Hz, 1H), 3.71 (s, 3H), 3.50-3.41 (m, 1H), 3.01 (dd, J=12.8, 5.9 Hz, 2H), 2.78-2.60 (m, 4H), 2.52 (dt, J=11.1, 5.2 Hz, 2H), 1.65-1.47 (m, 4H), 1.42 (s, 9H); $^{13}$C NMR (126 MHz, CDCl$_3$) δ 172.6, 172.5, 157.9, 155.3, 136.2, 130.4, 128.6, 128.4, 128.3, 114.8, 80.1, 67.5, 66.4, 61.0, 54.7, 52.4, 50.7, 37.6, 34.4, 28.5, 26.7, 24.8; HRMS (ESI/[M+H]$^+$) calcd. for C$_{31}$H$_{43}$N$_2$O$_7^+$: 555.3065, found [M+H]$^+$: 555.3064; FTIR (neat) $v_{max}$ 2932, 1713, 1511, 1366, 1243, 1158, 1022 cm$^{-1}$.

Benzyl 4-(((8R,9S,13S,14S)-13-methyl-17-oxo-7,8,9,11,12,13,14,15,16,17-decahydro-6H-cyclopenta[a]phenanthren-3-yl)oxy)-3-(piperidin-1-yl)butanoate (compound 85)

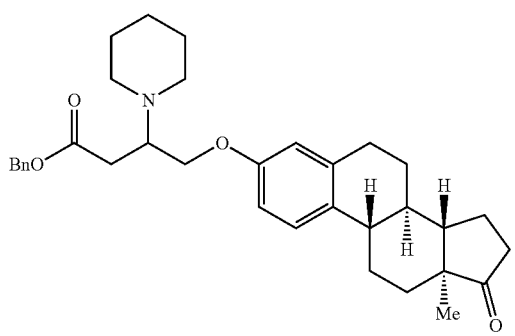

Compound 85 was prepared following the general procedure B (see Example 7 supra) (27.0 mg, 51% yield, dr 5:4). $^1$H NMR (500 MHz, CDCl$_3$) δ 7.47-7.28 (m, 5H), 7.18 (d, J=8.6 Hz, 1H), 6.68 (dt, J=8.6, 1.7 Hz, 1H), 6.61 (d, J=2.7 Hz, 1H), 4.11-4.04 (m, 1H), 3.95 (dt, J=10.2, 5.4 Hz, 1H), 3.47 (p, J=7.5, 7.0 Hz, 1H), 2.96-2.84 (m, 2H), 2.74-2.62 (m, 4H), 2.60-2.42 (m, 3H), 2.42-2.34 (m, 1H), 2.24 (s, OH), 2.13 (dd, J=19.0, 9.0 Hz, 1H), 2.07-1.90 (m, 2H), 1.78-1.57 (m, 1H), 1.54-1.46 (m, 8H), 1.43-1.33 (m, 2H), 0.91 (s, 3H); $^{13}$C NMR (126 MHz, CDCl$_3$) δ 221.1, 172.5, 156.8, 137.9, 136.2, 132.4, 128.6, 128.4, 128.3, 126.5, 114.7, 114.7, 112.3, 67.4, 66.4, 61.1, 50.7, 50.6, 48.2, 44.2, 38.5, 36.0, 34.4, 31.8, 29.8, 26.7, 26.1, 24.8, 21.8, 14.0; HRMS (ESI/[M+H]$^+$) calcd. for C$_{34}$H$_{44}$NO$_4^+$: 530.3265, found [M+H]$^+$: 530.3263; FTIR (neat) $v_{max}$ 2929, 1735, 1498, 1234, 1154, 1056 cm$^{-1}$.

1-(1-(4-Chlorophenoxy)-3-(phenylsulfonyl)propan-2-yl)piperidine (compound 86)

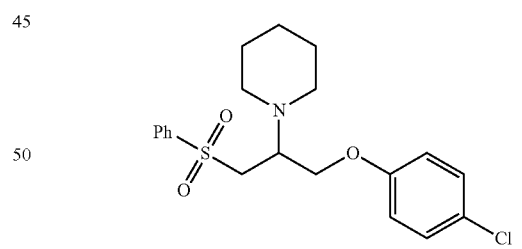

Compound 86 was prepared following the general procedure A (see Example 7 supra) (32.7 mg, 83% yield). $^1$H NMR (500 MHz, CDCl$_3$) δ 8.05-7.80 (m, 2H), 7.69-7.57 (m, 1H), 7.58-7.43 (m, 2H), 7.24-7.12 (m, 2H), 6.84-6.67 (m, 2H), 4.03 (qd, J=9.7, 4.6 Hz, 2H), 3.57-3.45 (m, 2H), 3.45-3.32 (m, 1H), 2.45 (dddd, J=35.6, 10.9, 7.0, 3.4 Hz, 4H), 1.46-1.24 (m, 4H), 1.20 (td, J=9.2, 8.5, 4.1 Hz, 2H); $^{13}$C NMR (126 MHz, CDCl$_3$) δ 157.0, 140.6, 133.5, 129.5, 129.2, 128.2, 126.2, 116.0, 66.7, 59.4, 54.6, 50.4, 26.1, 24.5; HRMS (ESI/[M+H]$^+$) calcd. for C$_{20}$H$_{25}$ClNO$_3$S$^+$: 394.1238, found [M+H]$^+$: 394.1237; FTIR (neat) $v_{max}$ 2934, 2852, 1595, 1492, 1303, 1242, 1143, 1084 cm$^{-1}$.

1-(1-(4-Chlorophenoxy)-3-(phenylsulfonyl)propan-2-yl)pyrrolidine (compound 87)

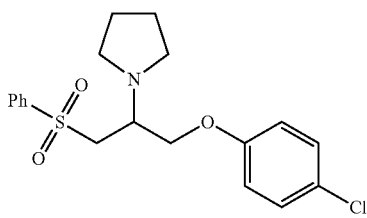 [SMILES: O=S(=O)(CC(COc1ccc(Cl)cc1)N1CCCC1)c1ccccc1]

Compound 87 was prepared following the general procedure A (see Example 7 supra) (24.3 mg, 64% yield). $^1$H NMR (500 MHz, CDCl$_3$) δ 7.99-7.82 (m, 2H), 7.67-7.58 (m, 1H), 7.56-7.45 (m, 2H), 7.24-7.13 (m, 2H), 6.84-6.73 (m, 2H), 4.25-4.03 (m, 2H), 3.63-3.51 (m, 2H), 3.49-3.30 (m, 2H), 2.56 (dt, J=39.5, 7.7 Hz, 4H), 1.85-1.47 (m, 4H); $^{13}$C NMR (126 MHz, CDCl$_3$) δ 157.1, 140.3, 133.7, 129.5, 129.3, 128.1, 126.3, 116.1, 68.0, 55.8, 54.8, 49.7, 23.6; HRMS (ESI/[M+H]$^+$) calcd. for C$_{19}$H$_{23}$ClNO$_3$S$^+$: 380.1081, found [M+H]$^+$: 380.1081; FTIR (neat) v$_{max}$ 2967, 1581, 1492, 1303, 1242, 1146, 1085 cm$^{-1}$.

1-(1-(4-Chlorophenoxy)-3-(phenylsulfonyl)propan-2-yl)azepane (compound 88)

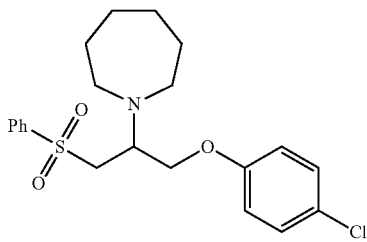 [SMILES: O=S(=O)(CC(COc1ccc(Cl)cc1)N1CCCCCC1)c1ccccc1]

Compound 88 was prepared following the general procedure A (see Example 7 supra) (24.3 mg, 64% yield). $^1$H NMR (500 MHz, CDCl$_3$) δ 8.01-7.93 (m, H), 7.70-7.58 (m, 1H), 7.59-7.46 (m, 2H), 7.26-7.02 (m, 2H), 6.81-6.69 (m, 2H), 4.18-3.89 (m, 2H), 3.75-3.53 (m, 1H), 3.39 (d, J=6.0 Hz, 2H), 2.79-2.55 (m, 4H), 1.55-1.31 (m, 8H); $^{13}$C NMR (126 MHz, CDCl$_3$) δ 157.1, 140.4, 133.7, 129.5, 129.3, 128.1, 128.1, 126.2, 116.1, 67.9, 59.7, 55.8, 52.1, 51.9, 29.6, 29.5, 27.0; HRMS (ESI/[M+H]$^+$) calcd. for C$_{21}$H$_{27}$ClNO$_3$S$^+$: 408.1395, found [M+H]$^+$: 408.1392; FTIR (neat) v$_{max}$ 2925, 2852, 1492, 1304, 1242, 1147, 1085 cm$^{-1}$.

1-(1-(4-Chlorophenoxy)-3-(phenylsulfonyl)propan-2-yl)-4-phenylpiperidine (compound 89)

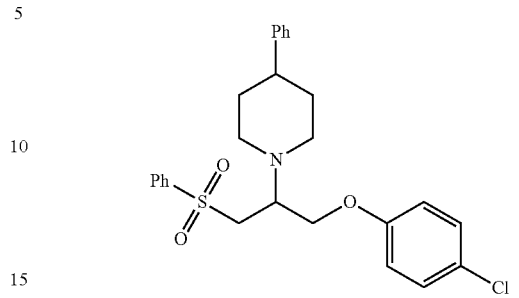

Compound 89 was prepared following the general procedure A (see Example 7 supra) (39.5 mg, 84% yield). $^1$H NMR (500 MHz, CDCl$_3$) δ 8.04-7.90 (m, 2H), 7.71-7.61 (m, 1H), 7.62-7.52 (m, 2H), 7.33-7.22 (m, 5H), 7.21-7.16 (m, 1H), 7.15-7.03 (m, 2H), 6.92-6.72 (m, 2H), 4.27-3.96 (m, 2H), 3.69-3.52 (m, 2H), 3.43 (dd, J=14.3, 4.9 Hz, 1H), 2.88 (ddt, J=11.2, 4.3, 2.3 Hz, 1H), 2.82-2.67 (m, 1H), 2.58 (td, J=11.4, 2.6 Hz, 1H), 2.40-2.18 (m, 2H), 1.68 (ddd, J=12.6, 3.8, 2.3 Hz, 1H), 1.67-1.55 (m, 1H), 1.47 (td, J=12.3, 4.1 Hz, 1H), 1.07 (dd, J=12.3, 4.0 Hz, 1H); $^{13}$C NMR (126 MHz, CDCl$_3$) δ 156.9, 146.2, 140.7, 133.6, 129.6, 129.3, 128.5, 128.2, 128.1, 126.9, 126.3, 116.0, 66.6, 59.1, 54.8, 52.3, 48.0, 42.7, 42.6, 33.7, 33.2; HRMS (ESI/[M+H]$^+$) calcd. for C$_{26}$H$_{29}$ClNO$_3$S$^+$: 470.1551, found [M+H]$^+$: 470.1549; FTIR (neat) v$_{max}$ 3060, 2935, 1491, 1302, 1242, 1146, 1084 cm$^{-1}$.

2-(4-(3-(Phenylsulfonyl)-2-(piperidin-1-yl)propoxy) phenyl)ethan-1-ol (compound 90)

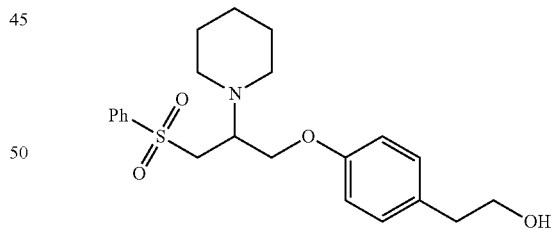

Compound 90 was prepared following the general procedure A (see Example 7 supra) (31.8 mg, 79% yield). $^1$H NMR (500 MHz, CDCl$_3$) δ 8.02-7.85 (m, 2H), 7.66-7.58 (m, 1H), 7.56-7.48 (m, 2H), 7.20-7.07 (m, 2H), 6.85-6.75 (m, 2H), 4.08-3.99 (m, 2H), 3.82 (t, J=6.5 Hz, 2H), 3.59-3.47 (m, 2H), 3.42 (d, J=8.9 Hz, 1H), 2.80 (t, J=6.6 Hz, 2H), 2.50 (ddd, J=10.8, 6.7, 3.3 Hz, 2H), 2.42 (td, J=7.8, 7.4, 3.6 Hz, 2H), 1.35-1.23 (m, 4H), 1.18 (s, 2H); $^{13}$C NMR (126 MHz, CDCl$_3$) δ 157.1, 140.7, 133.5, 131.2, 130.1, 129.2, 128.2, 114.9, 66.3, 64.0, 59.5, 54.7, 50.4, 38.4, 26.0, 24.5; HRMS (ESI/[M+H]$^+$) calcd. for C$_{22}$H$_{30}$NO$_4$S$^+$: 404.1890, found [M+H]$^+$: 404.1888; FTIR (neat) v$_{max}$ 3421, 2932, 2855, 1511, 1447, 1299, 1241, 1143, 1084, 1047 cm$^{-1}$.

7-(3-(Phenylsulfonyl)-2-(piperidin-1-yl)propoxy)-2H-chromen-2-one (compound 91)

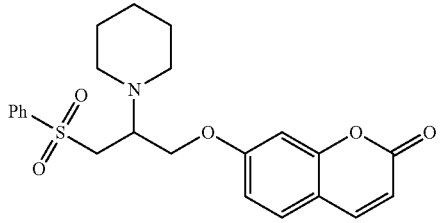 [SMILES: O=c1ccc2ccc(OCC(CS(=O)(=O)c3ccccc3)N3CCCCC3)cc2o1]

Compound 91 was prepared following the general procedure A (see Example 7 supra) (38.9 mg, 91% yield). $^1$H NMR (500 MHz, CDCl$_3$) δ 8.04-7.82 (m, 2H), 7.73-7.57 (m, 2H), 7.57-7.45 (m, 2H), 7.36 (d, J=8.6 Hz, 1H), 6.81 (dd, J=8.6, 2.4 Hz, 1H), 6.75 (d, J=2.4 Hz, 1H), 6.25 (d, J=9.5 Hz, 1H), 4.14 (qd, J=9.8, 4.8 Hz, 2H), 3.56-3.46 (m, 2H), 3.40 (dd, J=13.8, 5.2 Hz, 1H), 2.45 (dddd, J=33.9, 11.0, 6.9, 3.2 Hz, 4H), 1.45-1.12 (m, 6H); $^{13}$C NMR (126 MHz, CDCl$_3$) δ 161.5, 161.2, 155.9, 143.5, 140.4, 133.6, 129.3, 129.0, 128.2, 113.6, 113.1, 112.9, 101.8, 67.0, 59.2, 54.5, 50.4, 26.0, 24.4; HRMS (ESI/[M+H]$^+$) calcd. for C$_{23}$H$_{26}$NO$_5$S$^+$: 428.1526, found [M+H]$^+$: 428.1526; FTIR (neat) ν$_{max}$ 2934, 1731, 1613, 1295, 1142, 1123, 836 cm$^{-1}$.

(8R,9S,13S,14S)-13-Methyl-3-(3-(phenylsulfonyl)-2-(piperidin-1-yl)propoxy)-6,7,8,9,11,12,13,14,15,16-decahydro-17H-cyclopenta[a]phenanthren-17-one (compound 92)

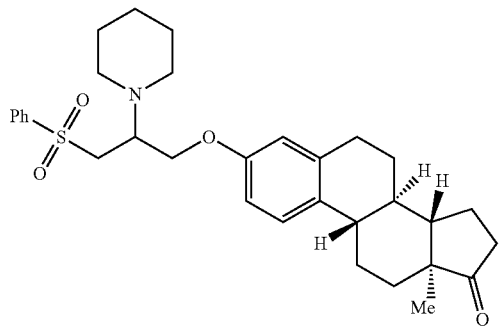 [SMILES: C[C@]12CC[C@@H]3c4ccc(OCC(CS(=O)(=O)c5ccccc5)N5CCCCC5)cc4CC[C@H]3[C@@H]1CCC2=O]

Compound 92 was prepared following the general procedure A (see Example 7 supra) (39.7 mg, 74% yield). $^1$H NMR (500 MHz, CDCl$_3$) δ 8.02-7.88 (m, 2H), 7.69-7.59 (m, 1H), 7.58-7.48 (m, 2H), 7.18 (dd, J=8.7, 1.0 Hz, 1H), 6.66 (dd, J=8.6, 2.7 Hz, 1H), 6.59 (dd, J=2.7, 1.2 Hz, 1H), 4.15-3.93 (m, 2H), 3.61-3.47 (m, 2H), 3.45-3.34 (m, 1H), 2.98-2.81 (m, 2H), 2.61-2.46 (m, 3H), 2.46-2.33 (m, 3H), 2.24 (td, J=10.8, 4.2 Hz, 1H), 2.14 (dt, J=18.9, 8.9 Hz, 1H), 2.14-1.81 (m, 3H), 1.69-1.57 (m, 2H), 1.57-1.37 (m, 5H), 1.36-1.20 (m, 5H), 1.16 (tdd, J=11.8, 6.4, 3.1 Hz, 2H), 0.90 (s, 3H); $^{13}$C NMR (126 MHz, CDCl$_3$) δ 221.0, 156.4, 140.7, 138.0, 133.4, 132.7, 129.1, 128.2, 128.2, 126.5, 114.8, 114.7, 112.3, 112.3, 66.1, 59.5, 54.8, 50.6, 50.4, 48.2, 44.1, 38.5, 36.0, 31.7, 29.8, 26.7, 26.1, 26.0, 24.5, 21.8, 14.0; HRMS (ESI/[M+H]$^+$) calcd. for C$_{32}$H$_{42}$NO$_4$S$^+$: 536.2828, found [M+H]$^+$: 536.2826; FTIR (neat) ν$_{max}$ 2931, 1736, 1499, 1303, 1253, 1143, 752 cm$^{-1}$.

1-(1-(4-Chlorophenoxy)-3-((3-(trifluoromethyl)phenyl)sulfonyl)propan-2-yl)piperidine (compound 93)

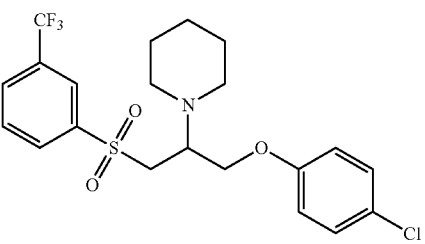 [SMILES: O=S(=O)(CC(COc1ccc(Cl)cc1)N1CCCCC1)c1cccc(C(F)(F)F)c1]

Compound 93 was prepared following the general procedure A (see Example 7 supra) (39.7 mg, 74% yield). $^1$H NMR (500 MHz, CDCl$_3$) δ 8.22 (s, 1H), 8.13 (d, J=8.0 Hz, 1H), 7.88 (d, J=7.9 Hz, 1H), 7.69 (t, J=7.8 Hz, 1H), 7.25-7.17 (m, 2H), 6.85-6.71 (m, 2H), 4.11-3.91 (m, 2H), 3.66-3.51 (m, 2H), 3.43 (dd, J=14.3, 4.0 Hz, 1H), 2.50 (dt, J=14.7, 4.6 Hz, 2H), 2.37 (t, J=9.6 Hz, 2H), 1.25 (d, J=6.5 Hz, 4H), 1.14-1.01 (m, 2H); $^{13}$C NMR (126 MHz, CDCl$_3$) δ 156.8, 142.1, 131.9 (q, J=33.8 Hz), 131.5, 130.1, 130.0, 129.6, 126.4, 125.5, 123.4 (q, J=273.1 Hz), 115.9, 65.9, 59.7, 55.0, 50.3, 25.9, 24.3; HRMS (ESI/[M+H]$^+$) calcd. for C$_{21}$H$_{24}$ClF$_3$NO$_3$S$^+$: 462.1107, found [M+H]$^+$: 462.1108; FTIR (neat) ν$_{max}$ 2934, 1492, 1325, 1302, 1141, 1100, 1071 cm$^{-1}$.

1-(1-(4-Chlorophenoxy)-3-(thiophen-2-ylsulfonyl)propan-2-yl)piperidine (compound 94)

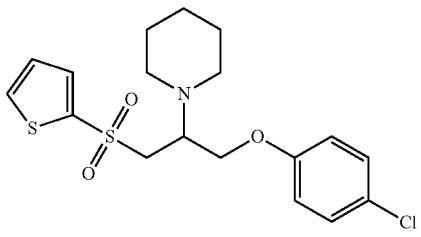 [SMILES: O=S(=O)(CC(COc1ccc(Cl)cc1)N1CCCCC1)c1cccs1]

Compound 94 was prepared following the general procedure A (see Example 7 supra) (30.8 mg, 77% yield). $^1$H NMR (500 MHz, CDCl$_3$) δ 7.69 (t, J=5.5 Hz, 2H), 7.22 (d, J=8.5 Hz, 2H), 7.12 (t, J=4.4 Hz, 1H), 6.79 (d, J=8.4 Hz, 2H), 4.06 (qd, J=9.8, 4.1 Hz, 2H), 3.65-3.43 (m, 3H), 2.67-2.36 (m, 4H), 1.47-1.29 (m, 6H); $^{13}$C NMR (126 MHz, CDCl$_3$) δ 157.0, 141.5, 134.1, 133.8, 129.5, 127.9, 126.3, 116.1, 66.8, 59.6, 56.1, 50.6, 26.3, 24.5; HRMS (ESI/[M+H]$^+$) calcd. for C$_{18}$H$_{23}$ClNO$_3$S$_2$$^+$: 400.0799, found [M+H]$^+$: 400.0797; FTIR (neat) ν$_{max}$ 2929, 1491, 1403, 1308, 1239, 1137, 1090, 1015 cm$^{-1}$.

1-(1-(Benzylsulfonyl)-3-(4-chlorophenoxy)propan-2-yl)piperidine (compound 95)

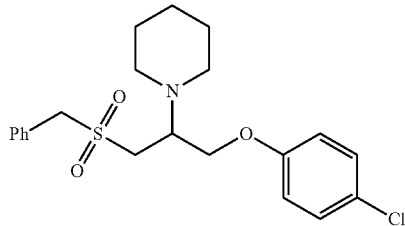 [SMILES: O=S(=O)(Cc1ccccc1)CC(COc1ccc(Cl)cc1)N1CCCCC1]

Compound 95 was prepared following the general procedure A (see Example 7 supra) (32.2 mg, 79% yield). $^1$H NMR (500 MHz, CDCl$_3$) δ 7.48-7.38 (m, 5H), 7.24-7.20 (m, 2H), 6.85-6.78 (m, 2H), 4.60 (d, J=13.6 Hz, 1H), 4.38 (d, J=13.6 Hz, 1H), 4.16-3.99 (m, 2H), 3.65 (dd, J=8.6, 4.5 Hz, 1H), 3.43-3.32 (m, 1H), 3.06 (dd, J=14.8, 4.2 Hz, 1H), 2.80-2.72 (m, 2H), 2.61 (s, 2H), 1.62 (dd, J=16.2, 7.9 Hz, 4H), 1.47 (t, J=6.1 Hz, 2H); $^{13}$C NMR (126 MHz, CDCl$_3$) δ 156.9, 131.2, 129.6, 129.1, 127.9, 126.4, 116.0, 66.3, 61.0, 59.7, 51.4, 50.8, 26.7, 24.6; HRMS (ESI/[M+H]$^+$) calcd. for C$_{21}$H$_{27}$ClNO$_3$S$^+$: 408.1395, found [M+H]$^+$: 408.1391; FTIR (neat) ν$_{max}$ 2933, 1491, 1297, 1240, 1117, 1030, 824 cm$^{-1}$.

1-(1-((4-Bromophenyl)thio)-3-(phenylsulfonyl)propan-2-yl)piperidine (compound 96)

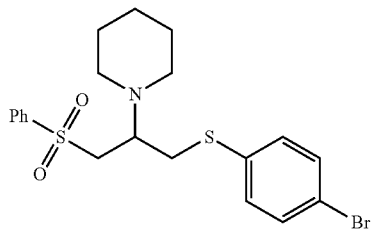 [SMILES: O=S(=O)(CC(CSc1ccc(Br)cc1)N1CCCCC1)c1ccccc1]

Compound 96 was prepared following the general procedure B (see Example 7 supra) (22.2 mg, 49% yield). $^1$H NMR (500 MHz, CDCl$_3$) δ 7.88-7.83 (m, 2H), 7.65-7.60 (m, 1H), 7.53 (t, J=7.8 Hz, 2H), 7.44-7.38 (m, 2H), 7.24-7.19 (m, 2H), 3.42 (dd, J=14.3, 6.0 Hz, 1H), 3.33-3.24 (m, 1H), 3.24-3.14 (m, 2H), 2.92 (dd, J=12.1, 6.5 Hz, 1H), 2.34-2.20 (m, 4H), 1.28 (ddt, J=22.0, 16.3, 10.1 Hz, 6H). $^{13}$C NMR (126 MHz, CDCl$_3$) δ 140.2, 135.3, 133.6, 132.2, 131.8, 129.2, 128.2, 120.5, 59.6, 55.2, 49.2, 34.8, 25.8, 24.6; HRMS (ESI/[M+H]$^+$) calcd. for C$_{20}$H$_{25}$BrNO$_2$S$_2$$^+$: 454.0510/456.0490, found [M+H]$^+$: 454.0500/456.0480; FTIR (neat) ν$_{max}$ 2934, 1492, 1474, 1326, 1303, 1143, 1087, 1007 cm$^{-1}$.

1-(1-((4-Chlorophenyl)sulfonyl)-3-(naphthalen-2-ylthio)propan-2-yl)piperidine (compound 97)

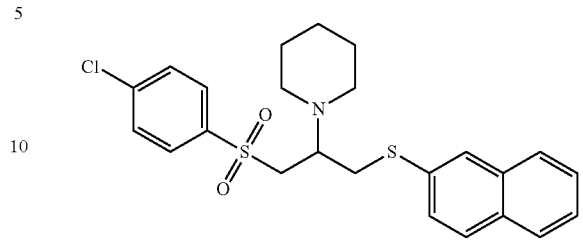

Compound 97 was prepared following the general procedure B (29.9 mg, 65% yield). $^1$H NMR (500 MHz, CDCl$_3$) δ 7.83-7.80 (m, 2H), 7.78-7.75 (m, 2H), 7.73 (d, J=8.6 Hz, 2H), 7.54-7.44 (m, 2H), 7.41 (dd, J=8.5, 1.9 Hz, 1H), 7.38-7.32 (m, 2H), 3.46-3.38 (m, 2H), 3.31 (dd, J=13.1, 6.0 Hz, 2H), 3.24-3.14 (m, 1H), 2.90 (dd, J=13.1, 8.2 Hz, 1H), 2.35 (td, J=7.0, 3.3 Hz, 2H), 2.26 (ddd, J=10.6, 6.9, 2.7 Hz, 2H), 1.32 (ddt, J=15.6, 10.7, 5.6 Hz, 4H), 1.29-1.19 (m, 2H); $^{13}$C NMR (126 MHz, CDCl$_3$) δ 140.1, 138.7, 133.9, 132.9, 132.2, 129.8, 129.3, 128.8, 128.5, 128.0, 127.9, 127.4, 126.9, 126.2, 59.8, 55.6, 49.2, 33.7, 25.8, 24.5; HRMS (ESI/[M+H]$^+$) calcd. for C$_{24}$H$_{27}$ClNO$_2$S$_2$$^+$: 460.1166/462.1143, found [M+H]$^+$: 460.1167/462.1143; FTIR (neat) ν$_{max}$ 2933, 1583, 1475, 1394, 1308, 1149, 1088, 814 cm$^{-1}$.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

While certain embodiments of the present disclosure have been shown and described herein, it will be apparent to those skilled in the art that such embodiments are provided by way of example only. It is not intended that the claimed invention be limited by the specific examples provided within the specification.

While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein, which depend upon a variety of conditions and variables. It should be understood that various alternatives to the embodiments of the invention described herein may be employed in practicing the invention. It is, therefore, contemplated that the invention shall also cover any such alternatives, modifications, variations or equivalents. It is intended that the following claims define the scope of the invention and that methods and structures within the scope of these claims and their equivalents be covered thereby.

Those skilled in the art will recognize that numerous modifications can be made to the specific implementations described above. The implementations should not be limited to the particular limitations described. Other implementations may be possible.

Certain Additional Definitions

As used herein and in the appended claims, the singular forms "a," "and," and "the" include plural referents unless the context clearly dictates otherwise. Thus, for example, reference to "a compound" includes a plurality of such compounds. When ranges are used herein for physical properties, such as molecular weight, or chemical properties, such as chemical formulae, all combinations and sub-combinations of ranges and specific embodiments therein are intended to be included. The term "about," when referring to a number or a numerical range, means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude in certain embodiments of any compound, composition, method, process, or the like that may "consist of" or "consist essentially of" the described features.

"Alkyl" refers to a straight or branched or cyclic hydrocarbon chain radical consisting solely of carbon and hydrogen atoms, containing no unsaturation, and having from one to fifteen carbon atoms (e.g., $C_1$-$C_{15}$ alkyl). In various embodiments, an alkyl comprises three to six carbon atoms (e.g., $C_3$-$C_6$ alkyl), one to thirteen carbon atoms (e.g., $C_1$-$C_{13}$ alkyl), one to eight carbon atoms (e.g., $C_1$-$C_5$ alkyl), one to five carbon atoms (e.g., $C_1$-$C_5$ alkyl), one to four carbon atoms (e.g., $C_1$-$C_4$ alkyl), one to three carbon atoms (e.g., $C_1$-$C_3$ alkyl), one to two carbon atoms (e.g., $C_1$-$C_2$ alkyl), one carbon atom (e.g., $C_1$ alkyl), five to fifteen carbon atoms (e.g., $C_5$-$C_{15}$ alkyl), five to eight carbon atoms (e.g., $C_5$-$C_8$ alkyl), two to five carbon atoms (e.g., $C_2$-$C_5$ alkyl), or three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Cyano" refers to the group —CN.

"Oxo" refers to the group =O.

The term "substituted" means a functional group in which one or more hydrogen atoms contained therein are replaced by one or more non-hydrogen atoms. The term "functional group" or "substituent" means a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Non-limiting examples of substituents that can be bonded to a substituted carbon atom (or other functional groups such as nitrogen) can include, without limitation, F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, (CH$_2$)$_{0-2}$P(O)OR$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R, wherein R can be hydrogen or a carbon-based moiety, and wherein the carbon-based moiety can itself be further substituted; for example, wherein R can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R can be independently mono- or multi-substituted; or wherein two R groups bonded to a nitrogen atom or to adjacent nitrogen atoms can together with the nitrogen atom or atoms form a heterocyclyl, which can be mono- or independently multi-substituted.

The terms "halo," "halogen," or "halide" group, as used herein, by themselves or as part of another substituent, mean, unless otherwise stated, a fluorine, chlorine, bromine, or iodine atom.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless specifically stated otherwise, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

The term "aryl" means a substituted or unsubstituted cyclic aromatic hydrocarbon that does not contain heteroatoms in the ring. Accordingly, aryl groups can include, without limitation, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons (C$_6$-C$_{14}$) or from 6 to 10 carbon atoms (C$_6$-C$_{10}$) in the ring portions of the groups. Aryl groups can be unsubstituted or substituted, as defined herein.

Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

A heteroaryl ring is an embodiment of a heterocyclyl group. The phrase "heterocyclyl group" includes fused ring species including those that comprise fused aromatic and non-aromatic groups. Representative heterocyclyl groups include, but are not limited to, pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "stable", as used herein, refers to compounds that are not substantially altered when subjected to conditions to allow for their production, detection, and, in certain embodiments, their recovery, purification, and use for one or more of the purposes disclosed herein.

The phrase "pharmaceutically acceptable salt" refers to pharmaceutically acceptable organic or inorganic salts of a compound of the referenced formula. For use in medicine, the salts of a compound of a formula can be pharmaceutically acceptable salts. Other salts can, however, be useful in the preparation of a compound of an identified formula or of their pharmaceutically acceptable salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure.

Pharmaceutically acceptable salts of the compounds of a formula described herein can include those derived from suitable inorganic or organic acids or bases. In some embodiments, the salts can be prepared in situ during the final isolation and purification of the compounds. In other embodiments the salts can be prepared from the free form of the compound in a separate synthetic step.

Salts derived from inorganic bases include, for example and without limitation, aluminum, ammonium, calcium, copper, ferric, ferrous, lithium, magnesium, manganic salts, manganous, potassium, sodium, and zinc. Particular embodiments include ammonium, calcium, magnesium, potassium and sodium salts. Salts derived from pharmaceutically acceptable organic non-toxic bases can include salts of primary, secondary and tertiary amines, substituted amines including naturally occurring substituted amines, cyclic amines and basic ion exchange resins, such as arginine, betaine, caffeine, choline, N, N1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, and tromethamine.

Salts can be prepared from pharmaceutically acceptable non-toxic acids, including inorganic and organic acids. Such acids include, without limitation, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acid. In certain embodiments, the salt can include citric, hydrobromic, hydrochloric, maleic, phosphoric, sulfuric and tartaric acids. Other exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and/or pamoate salts.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

The invention claimed is:

1. A method of synthesizing amines from activated allene compounds or derivatives thereof in a one-pot reaction comprising:

providing a solution comprising an electrophilic amine or an allene and an amine halogenating reagent and adding a first compound to the solution to carry out a first animation reaction, wherein the first compound comprises an electron-withdrawing group (EWG);

adding a nucleophilic reagent and a base to a reaction mixture of the animation reaction to carry out a second nucleophilic reaction; and adding a reducing reagent to a reaction mixture of the nucleophilic reaction to carry out a third enamine reduction reaction and synthesize an amine product from an activated allene compound or derivative thereof;

wherein the amine product has a structure of Formula (III) or is a pharmaceutically acceptable salt thereof:

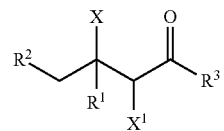

Formula (III)

wherein:
X is an N containing cyclic group;
$R^1$ is D or absent;
$R^2$ is

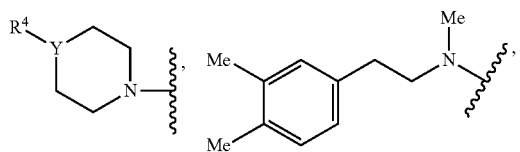

-continued

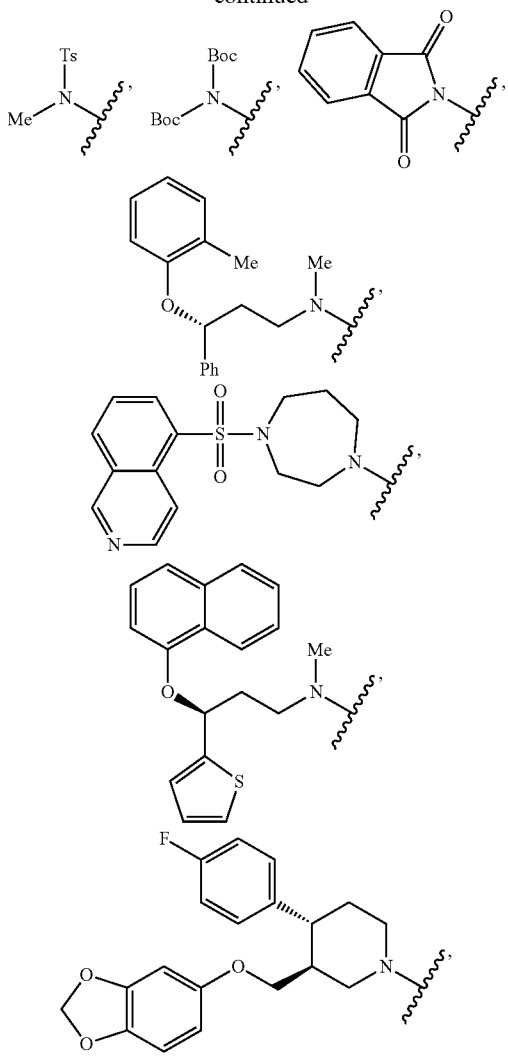

wherein Y is N, S, C, or O, and

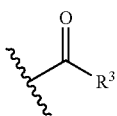

comprises the EWG, wherein R³ is OBn, OEt,

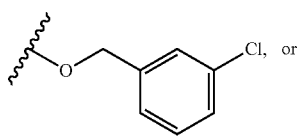

-continued

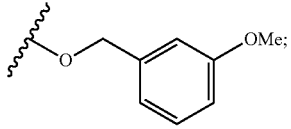

Xa is an N-containing cyclic group; and
$X^1$ is absent or F.

2. The method of claim 1, wherein the amine halogenating reagent comprises one or more of t-BuOCl, tetra-n-butylammonium iodide (TBAI), N-bromosuccinimide (NBS), N-Iodosuccinimide (NIS), N-Chlorosuccinimide (NCS), KI, and NaI.

3. The method of claim 2, wherein the amine halogenating reagent comprises a mixture of t-BuOCl and TBAI.

4. The method of claim 1, wherein the electrophilic amine is a cyclic aliphatic amine.

5. The method of claim 1, wherein the electrophilic amine has a structure of the formula $R^3R^4NH$, wherein $R^3$ and $R^4$ are each independently an optionally substituted $C_3$-$C_{10}$ cycloalkyl, $C_3$-$C_{10}$ hetero cyclic ring, $C_5$-$C_{12}$ aryl, or $C_5$-$C_{12}$ heteroaryl.

6. The method of claim 5, wherein the first compound has a structure of Formula I:

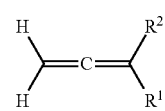

wherein:
$R^1$ is H or F; and
$R^2$ is the EWG.

7. The method of claim 1, wherein the nucleophilic reagent is a cyclic amine, an acyclic amine, an imide, or a sulfonamide.

8. The method of claim 7, wherein the nucleophilic reagent has a structure of the formula $HNR^6R^7$ or $HXR^8$, wherein:
X is O or S; and
$R^6$, $R^7$ and $R^8$ are each independently an optionally substituted $C_1$-$C_{12}$ straight or branched alkyl, $C_2$-$C_{12}$ straight or branched alkenyl, $C_2$-$C_{12}$ straight or branched alkynyl, $C_3$-$C_{10}$ cycloalkyl, $C_3$-$C_{10}$ hetero cyclic ring, $C_5$-$C_{12}$ aryl, or $C_5$-$C_{12}$ heteroaryl.

9. The method of claim 8, wherein $R^6$ and $R^7$ are joined together to form an optionally substituted heterocyclic ring.

10. The method of claim 1, wherein the base is ceasium carbonate ($Cs_2CO_3$), potassium carbonate ($K_2CO_3$) or tetrahydrofuran (THF).

11. The method of claim 1, wherein the reducing agent comprises $NaBH_3CN$.

12. The method of claim 11, further comprising adding a co-solvent of MeOH/AcOH to a reaction mixture of the reduction reaction.

13. The method of claim 1, further comprising drying and purifying the activated allene compound or derivative thereof.

* * * * *